(12) United States Patent
Sanders et al.

(10) Patent No.: US 7,718,814 B2
(45) Date of Patent: May 18, 2010

(54) TOCOPHEROLS, TOCOTRIENOLS, OTHER CHROMAN AND SIDE CHAIN DERIVATIVES AND USES THEREOF

(75) Inventors: Bob G. Sanders, Austin, TX (US); Kimberly Kline, Austin, TX (US); Weiping Yu, Austin, TX (US)

(73) Assignee: Research Development Foundation, Carson City, NV (US)

( * ) Notice: Subject to any disclaimer, the term of this patent is extended or adjusted under 35 U.S.C. 154(b) by 71 days.

(21) Appl. No.: 11/928,991

(22) Filed: Oct. 30, 2007

(65) Prior Publication Data

US 2008/0161349 A1  Jul. 3, 2008

Related U.S. Application Data

(60) Division of application No. 10/695,275, filed on Oct. 28, 2003, now Pat. No. 7,300,954, which is a division of application No. 10/008,066, filed on Nov. 5, 2001, now Pat. No. 6,703,384, which is a continuation-in-part of application No. 09/502,592, filed on Feb. 11, 2000, now Pat. No. 6,770,672, which is a continuation-in-part of application No. 09/404,001, filed on Sep. 23, 1999, now Pat. No. 6,417,223.

(60) Provisional application No. 60/101,542, filed on Sep. 23, 1998.

(51) Int. Cl.
    C07D 311/00  (2006.01)
    C07D 315/00  (2006.01)

(52) U.S. Cl. ............................ 549/408; 549/416
(58) Field of Classification Search ............ None
    See application file for complete search history.

(56) References Cited

U.S. PATENT DOCUMENTS

| | | | |
|---|---|---|---|
| 3,869,477 A | 3/1975 | Shindo et al. | 260/345.5 |
| 4,181,725 A | 1/1980 | Voorhees et al. | 424/258 |
| 4,320,141 A | 3/1982 | Komatsu et al. | 424/284 |
| 4,457,918 A | 7/1984 | Holick et al. | 424/180 |
| 4,617,317 A | 10/1986 | Bennet | 514/458 |
| 4,645,845 A | 2/1987 | Gehrken et al. | 549/407 |
| 4,665,204 A | 5/1987 | Wirth | 549/410 |
| 4,873,088 A | 10/1989 | Mayhew et al. | 424/450 |
| 4,895,719 A | 1/1990 | Radhakrishnan et al. | 424/45 |
| 5,114,957 A | 5/1992 | Hendler et al. | 514/356 |
| 5,135,945 A | 8/1992 | Robinson et al. | 514/456 |
| 5,260,294 A | 11/1993 | Walser | 514/230 |
| 5,315,017 A | 5/1994 | Le Baut et al. | 549/408 |
| 5,336,485 A | 8/1994 | Fariss | 514/182 |
| 5,393,775 A | 2/1995 | Le Baut et al. | 514/456 |
| 5,403,834 A | 4/1995 | Malfroy-Camine et al. | 514/185 |
| 5,480,645 A | 1/1996 | Della Valle et al. | 424/439 |
| 5,545,660 A | 8/1996 | Grisar et al. | 514/458 |
| 5,610,180 A | 3/1997 | Fariss | 514/458 |
| 5,650,404 A | 7/1997 | Ogata et al. | 514/100 |
| 5,747,162 A | 5/1998 | Temple et al. | 428/395 |
| 5,780,445 A | 7/1998 | Schneider et al. | 514/27 |
| 5,827,878 A | 10/1998 | Makishima et al. | 514/458 |
| 5,915,818 A | 6/1999 | Tawaza et al. | 353/95 |
| 5,917,060 A | 6/1999 | Rosenau et al. | 549/408 |
| 5,919,818 A | 7/1999 | Lane et al. | 514/458 |
| 5,990,322 A | 11/1999 | Lee et al. | 549/410 |
| 6,022,560 A | 2/2000 | Yazdi et al. | 424/450 |
| 6,127,382 A | 10/2000 | Beard et al. | 514/311 |
| 6,133,312 A | 10/2000 | Elson | 514/458 |
| 6,417,223 B1 | 7/2002 | Sanders et al. | 514/456 |
| 6,645,998 B2 * | 11/2003 | Sanders et al. | 514/456 |
| 6,770,672 B1 | 8/2004 | Sanders et al. | 514/458 |
| 7,045,324 B2 | 5/2006 | Sanders et al. | 435/189 |
| 7,300,954 B2 * | 11/2007 | Sanders et al. | 514/456 |
| 7,312,232 B2 | 12/2007 | Sanders et al. | 514/311 |
| 2003/0236301 A1 | 12/2003 | Sanders et al. | 514/458 |

(Continued)

FOREIGN PATENT DOCUMENTS

CS    172015    12/1976

(Continued)

OTHER PUBLICATIONS

Arya et al., "Design and synthesis of analogs of vitamin E: antiproliferative activity against human breast adenocarcinoma cells," *Bioorg. Med. Chem. Lett.*, 8:2433-2438, 1998.

(Continued)

*Primary Examiner*—Elli Peselev
(74) *Attorney, Agent, or Firm*—Fulbright & Jaworski L.L.P.

(57) ABSTRACT

The present invention provides an antiproliferative compound having a structural formula

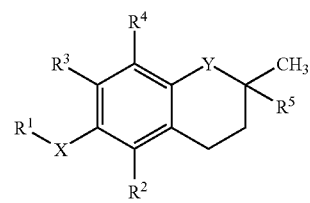

where X and Y independently are oxygen, nitrogen or sulfur; $R^1$ is alkyl, alkenyl, alkynyl, aryl, heteroaryl, carboxylic acid, carboxylate, carboxamide, ester, thioamide, thiolacid, thiolester, saccharide, alkoxy-linked saccharide, amine, sulfonate, sulfate, phosphate, alcohol, ethers or nitriles; $R^2$ and $R^3$ are hydrogen or $R^4$; $R^4$ is methyl, benzyl carboxylic acid, benzyl carboxylate, benzyl carboxamide, benzylester, saccharide or amine; and $R^1$ is alkenyl; where when Y is nitrogen, said nitrogen is substituted with $R^6$, wherein $R^6$ is hydrogen or methyl. Also provided are methods for treating a cell proliferative disease and for inducing apoptosis in a cell comprising administering this compound is also provided.

8 Claims, 11 Drawing Sheets

U.S. PATENT DOCUMENTS

2004/0235938 A1   11/2004   Sanders et al. .............. 514/448

FOREIGN PATENT DOCUMENTS

| | | |
|---|---|---|
| DE | 4304303 | 8/2004 |
| EP | 0436911 | 7/1990 |
| EP | 0506048 | 9/1992 |
| EP | 0636618 | 2/1995 |
| EP | 0751125 | 1/1997 |
| EP | 0754458 | 2/1997 |
| EP | 0768314 | 4/1997 |
| FR | 2672601 | 2/1991 |
| JP | 55076871 | 6/1980 |
| JP | 63303049 | 12/1988 |
| JP | 01041727 | 2/1989 |
| JP | 04229269 | 8/1992 |
| JP | 1997301969 A | 11/1997 |
| WO | WO 97/41852 | 11/1997 |
| WO | WO 98/17246 | 4/1998 |
| WO | WO 99/24417 | 5/1999 |
| WO | WO 00/16772 | 3/2000 |
| WO | WO 01/58889 | 8/2001 |
| WO | WO 03/039461 | 5/2003 |

OTHER PUBLICATIONS

Brown et al., "Novel heteroarotinoids as potential antagonists of mycobacterium bovis BCG," *J. Med. Chem.*, 47:1008-1017, 2004.

Burke et al., "Effects of topical and oral vitamin E on pigmentation and skin cancer induced by ultraviolet irradiation in Skh:2 hairless mice," *Nutrition and Cancer*, 38(1):87-97, 2000.

Djuric et al., "Growth inhibition of MCF-7 and MCF-10A human breast cells by alpha-tocopheryl hemisuccinate, cholesteryl hemisuccinate and their ether analogs," *Cancer Lett.*, 111:133-139, 1997.

Dominguez, "Hydroxyacetophenone derivatives from B. glutinosa," *J. Nat. Prod.*, 49:143-144, 1986.

Fabiani et al., "Antioxidants prevent the lymphocyte DNA damage induced by PMA-stimulated monocytes," Nutrition and Cancer, 39(2):284-291, 2001.

Fariss et al., "The selective antiproliferative effects of alpha-tocopheryl hemisuccinate and cholesteryl hemisuccinate on murine leukemia cells result from the action of the intact compounds," *Cancer Res.*, 54:3346-3351, 1994.

Fatope et al., "Design, synthesis, and testing of potential antisickling agents," *J. Med. Chem.*, 30:1973-1977, 1987.

Gura, "Systems for identifying new drugs are often faulty," *Science, New Series*, 278:1041-1042, 1997.

Helzlsouer et al., "Association between α-tocopherol, γ-tocopherol, selenium, and subsequent prostate cancer," *J Nat Cancer Inst*, 92(24):2018-2023, 2000.

Jiang et al., "γ-tocopherol, the major form of vitamin E in the US diet, deserves more attention," *Am J Clin Nutr*, 74:714-722, 2001.

Kakizaki et al., "Effect of a α-tocopherol on hepatocarcinogenesis in transforming growth factor-α (TGF-α) transgenic mice treated with diethylnitrosamine," *Int J Vitam Nutr Res*, 71(5):261-267, 2001.

Koyama et al., "Synthesis of fluorine analogues of vitamin E. II. Synthesis of 2-(3-chloropropyl)-2,5,7,8-tetramethyl-6-chromanol and its application for stereocontrolled Wittig reaction with trifluoromethyl ketones," *Chem. Pharm. Bull.*, 36:2950-2954, 1988.

Malvy et al., "Effect of two years' supplementation with natural antioxidants on vitamin and trace elements status biomarkers: preliminary data of the SU.VI.MAX study," Cancer Detection and Prevention, 25(5):479-485, 2001.

Neuzil et al., "Vitamin E analogues as inducers of apoptosis: implications for their potential antineoplastic role," *Redox Report*, 6(3):143-151, 2001.

Prasad et al., "Effects of tocopherol (vitamin E) acid succinate on morphological alterations and growth inhibition in melanoma cells in culture," *Cancer Res.*, 42:550-555, 1982.

Schwartz, "Directed lysis of experimental cancer by β-carotene in liposomes," *Nutrition and Cancer*, 16:107-124, 1991.

Schwartz, "The administration of beta carotene to prevent and regress oral carcinoma in the hamster cheek pouch and the associated enhancement of the immune response," *Adv Exp Med Biol*, 262:77-93, 1990.

Schwartz, "The effect of cartenoids on the antitumor immune response tin vivo and invitro with hamster and mouse immune effectors," *Annals New York Academy of Sciences*, 587:92-109, 1990.

Urano et al., "Synthesis of dl-α-tocopherol and dl-α-tocotrienol," *Chem. Pharm. Bull.*, 31:4341-4345, 1983.

Welch et al., "Syntheses and activities of antioxidant derivatives of retinoic acids," *J. Med. Chem.*, 25:81-84, 1981.

Werninghaus et al., "Protective effect of alpha-tocopherol in carrier liposomes on ultraviolet-mediated human epidermal cell damage in vitro," *Photodermatol Photoimmunol Photomed*, 8(6):236-242, 1991.

Will et al., "Attachment of vitamin E derivatives to oligonucleotides during solid-phase synthesis," *Tetrahedron Lett.* 33:2729-2732, 1992.

Balis, "Evolution of anticancer drug discovery and the role of cell-based screening," *J. Natl. Cancer Inst.*, 94:78-79, 2002.

Kerbel, "What is the optimal rodent model for anti-tumor drug testing?" *Cancer and Metastasis*, 17:301-304, 1999.

Monks et al., "The NCI anti-cancer drug screen: a smart screen to identify effectors of novel targets," *Anti-Cancer Drug Design*, 12:553-541, 1997.

"The Merck Manual of Diagnosis and Therapy," *Merck Research Laboratories*, edited by Beers and Berkow, pp. 397, 398, 948, 949, 1127-1135; 1999.

Bidzilya et al., "Solubilization of α-tocopherol and its analogs in aqueous solutions of nonionic surfactant," *Colloid Journal*, 57(2):157-159, 1995.

Koga and Terao, "Antioxidant behaviors of vitamin E analogues in unilamellar vesicles," *Biosci. Biotech. Biochem.*, 60(6):1043-1045, 1996.

Office Action issued in U.S. Appl. No. 11/876,612, mailed Aug. 1, 2008.

Bidzila et al., "Solubilization of alpha-Tocopherol and its analogs in aqueous solutions of nonionic surfactant," *Colloid Journal*, 57(2):173-175, 1995.

Koga et al., "Antioxidant behaviors of vitamin E analogues in unilamellar vscicles," *Biosci. Biotech. Biochem.*, 60(6):1043-1045, 1996.

Office Communication, issued in U.S. Appl. No. 11/876,612, dated Apr. 10, 2009.

Response to Office Communication, issued in U.S. Appl. No. 11/876,612, submitted Dec. 21, 2008.

\* cited by examiner

R⁵ = alkyl, alkenyl, akynyl, aryl, and heteroaryl.

1) MeOH
2) DiBAL-H
3) PPh₃, n-BuLi
various alkyl-, alkenyl-, alkynyl-, aryl- and heteroaryl halides R⁵ = alkyl, alkenyl, akynyl, aryl, and heteroaryl amides and esters.

1) DCC, HOSu
2) various alkyl-, alkenyl-, alkynyl-, aryl- and heteroaryl amines or alcohols

TOCOPHEROLS, TOCOTRIENOLS, OTHER CHROMAN AND SIDE CHAIN DERIVATIVES AND USES THEREOF

CROSS-REFERENCE TO RELATED APPLICATIONS

The present application is a divisional of application Ser. No. 10/695,275, filed Oct. 28, 2003, now issued as U.S. Pat. No. 7,300,954 on Nov. 27, 2007, which is a divisional of U.S. Ser. No. 10/008,066, filed Nov. 5, 2001, now issued as U.S. Pat. No. 6,703,384 on Mar. 9, 2004, which is a continuation-in-part of U.S. Ser. No. 09/502,592, filed Feb. 11, 2000, now issued as U.S. Pat. No. 6,770,672 on Aug. 3, 2004, which is a continuation-in-part of U.S. Ser. No. 09/404,001, filed Sep. 23, 1999, now issued as U.S. Pat. No. 6,417,223 on Jul. 9, 2002, which claims benefit of priority to provisional application U.S. Ser. No. 60/101,542, filed Sep. 23, 1998.

BACKGROUND OF THE INVENTION

1. Field of the Invention

The present invention relates generally to the fields of organic chemistry and antiproliferative and pro-apoptotic compounds. More specifically, the present invention relates to chroman-based compounds and derivatives and analogs thereof, and their uses as cell anti-proliferative, proapoptotic, immunomodulating, and anti-cancer agents.

2. Description of the Related Art

The regulatory controls of pro-life (cell proliferation) and pro-death (apoptosis) are extremely complex and involve multiple intracellular signaling pathways and multiple interacting gene products. Cancer cells may exhibit multiple defects in normal regulatory controls of cell proliferation, such as enhanced expression of genes, which allow them to increase in number. In addition to enhanced expression of pro-life genes, cancer cells down-regulate genes and their products that control pro-death signals, resulting in the accumulation and potential metastasis of life threatening cancer cells. Thus, combinations of unregulated cell proliferation and suppression of death inducing signaling pathways give cancer cells both growth and survival advantages.

Whether a cell increases in numbers or not depends on a balance of expression of negatively-acting and positively-acting growth regulatory gene products, and the presence or absence of functional cell death signaling pathways. Negative-acting growth regulatory genes contribute to blockage of cells in the cell cycle. Positive-acting growth regulatory genes stimulate cells to progress through the cell cycle. Genes involved in apoptosis can be either proapoptotic or antiapoptotic, and the dynamic balance between them determines whether a cell lives or dies. Cancer cells, in order to survive and increase their numbers, undergo a series of mutational events over time that remove regulatory controls that give them the ability to grow unchecked and survive even in the presence of proapoptotic signals, and develop attributes that permit them to escape detection and removal by the immune response defense system. Cancers may cause death of individuals unless removed by surgery or effectively treated with drugs.

A wide variety of pathological cell proliferative conditions exist for which novel therapeutic strategies and agents are needed to provide therapeutic benefits. These pathological conditions may occur in almost all cell types capable of abnormal cell proliferation or abnormal responsiveness to cell death signals. Among the cell types that exhibit pathological or abnormal growth and death characteristics are (1) fibroblasts, (2) vascular endothelial cells, and (3) epithelial cells. Thus, novel methods are needed to treat local or disseminated pathological conditions in all or almost all organ and tissue systems of individuals.

Most cancers, whether they are male specific, such as prostate or testicular, or female specific, such as breast, ovarian or cervical, or, whether they affect males and females equally, such as liver, skin or lung, with time undergo increased genetic lesions and epigenetic events, and eventually become highly metastatic and difficult to treat. Surgical removal of localized cancers has proven effective only when the cancer has not spread beyond the primary lesion. Once the cancer has spread to other tissues and organs, the surgical procedures must be supplemented with other more specific procedures to eradicate the diseased or malignant cells. Most of the commonly utilized supplementary procedures for treating diseased or malignant cells such as chemotherapy or bioradiation are not localized to the tumor cells and, although they have a proportionally greater destructive effect on malignant cells, often affect normal cells to some extent.

Some natural vitamin E compounds, and some derivatives of vitamin E have been used as proapoptotic and DNA synthesis inhibiting agents. Structurally, vitamin E is composed of a chromanol head and an alkyl side chain. There are eight major naturally occurring forms of vitamin E: alpha ($\alpha$), beta ($\beta$), gamma ($\gamma$), and delta ($\delta$) tocopherols and $\alpha$, $\beta$, $\gamma$, and $\delta$ tocotrienols. Tocopherols differ from tocotrienols in that they have a saturated phytyl side chain rather than an unsaturated isoprenyl side chain. The four forms of tocopherols and tocotrienols differ in the number of methyl groups on the chromanol head ($\alpha$ has three, $\beta$ and $\gamma$ have two and $\delta$ has one).

RRR-$\alpha$-tocopheryl succinate is a derivative of RRR-$\alpha$-tocopherol that has been structurally modified via an ester linkage to contain a succinyl moiety instead of a hydroxyl moiety at the 6-position of the chroman head. This ester linked succinate moiety of RRR-$\alpha$-tocopherol has been the most potent form of vitamin E affecting the biological actions of triggering apoptosis and inhibiting DNA synthesis. This form of vitamin E induces tumor cells to undergo apoptosis, while having no apoptotic inducing effects on normal cells. The succinated form of vitamin E is effective as an anticancer agent as an intact agent; however, cellular and tissue esterases that can cleave the succinate moiety, thereby converting the succinate form of RRR-$\alpha$-tocopherol to the free RRR-$\alpha$-tocopherol, render this compound ineffective as an anticancer agent. RRR-$\alpha$-tocopherol exhibits neither antiproliferative nor proapoptotic biological activity in cells of epithelial or immune origin.

The prior art is deficient in the lack of effective means of inhibiting undesirable or uncontrollable cell proliferation in a wide variety of pathophysiological conditions while having no to little effect on normal cells. The present invention fulfills this long-standing need and desire in the art.

SUMMARY OF THE INVENTION

In one embodiment of the present invention, there is provided a compound having a structural formula

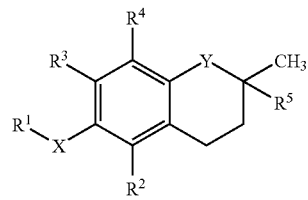

where X and Y independently are oxygen, nitrogen or sulfur; $R^1$ is alkyl, alkenyl, alkynyl, aryl, heteroaryl, carboxylic acid, carboxylate, carboxamide, ester, thioamide, thiolacid, thiolester, saccharide, alkoxy-linked saccharide, amine, sulfonate, sulfate, phosphate, alcohol, ethers or nitriles; $R^2$ and $R^3$ are hydrogen or $R^4$; $R^4$ is methyl, benzyl carboxylic acid, benzyl carboxylate, benzyl carboxamide, benzylester, saccharide or amine; and $R^5$ is alkenyl; where when Y is nitrogen, said nitrogen is substituted with $R^6$, wherein $R^6$ is hydrogen or methyl.

In another embodiment of the present invention there is provided a method for the treatment of a cell proliferative disease comprising administering to an individual a pharmacologically effective dose of a compound having a structural formula

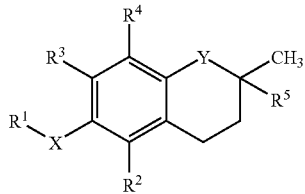

where $R^2$ and $R^3$ are hydrogen or $R^4$; $R^4$ is methyl, benzyl carboxylic acid, benzyl carboxylate, benzyl carboxamide, benzylester, saccharide or amine; and $R^5$ is alkenyl; $R^7$ is hydroxyl or $-XR^1$; wherein $R^1$ is alkyl, alkenyl, alkynyl, aryl, heteroaryl, carboxylic acid, carboxylate, carboxamide, ester, thioamide, thiolacid, thiolester, saccharide, alkoxy-linked saccharide, amine, sulfonate, sulfate, phosphate, alcohol, ethers or nitriles; and X and Y independently are oxygen, nitrogen or sulfur with the proviso that when Y is nitrogen, said nitrogen is substituted with $R^6$, wherein $R^6$ is hydrogen or methyl.

In yet another embodiment of the present invention there is provided a method of inducing apoptosis of a cell using the compounds disclosed supra.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized above may be had by reference to certain embodiments thereof which are illustrated in the appended drawings. These drawings form a part of the specification. It is to be noted; however, that the appended drawings illustrate preferred embodiments of the invention and therefore are not to be considered limiting in their scope.

FIG. 6A shows the synthetic scheme for compounds 31-38 and FIG. 6B shows the synthetic scheme for compounds 39-43.

DETAILED DESCRIPTION OF THE INVENTION

Figure 1:
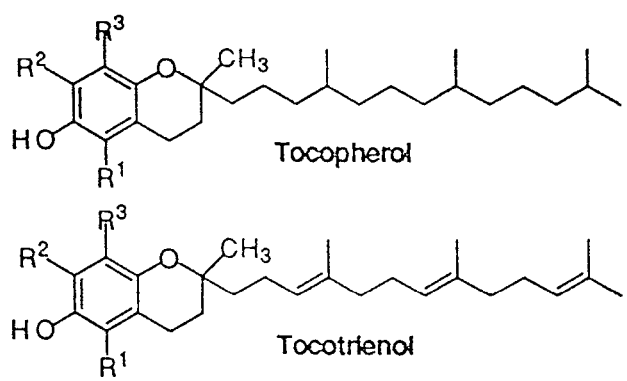
FIG. 1 shows general structure of tocopherol, tocotrienol and other chroman-based compounds.
Figure 2A:
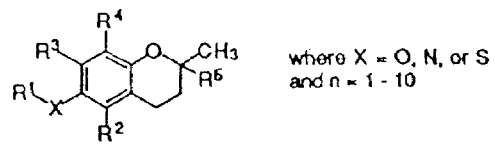
FIGS. 2A, 2B and 2C shows general synthetic organic approaches for the chemical variation of chromanol compounds at position $R^1$.
Figure 2A:
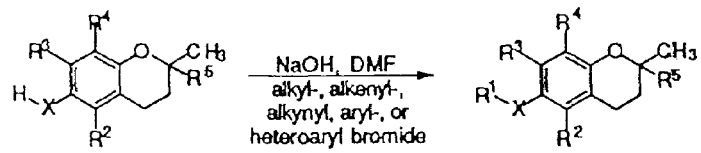
Figure 2A:
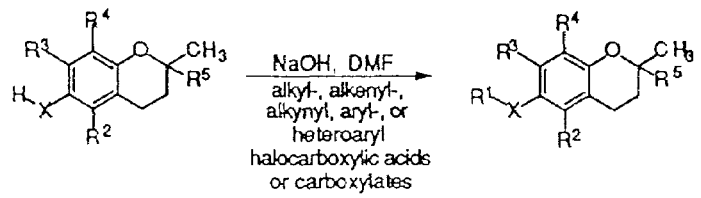
Figure 2A:
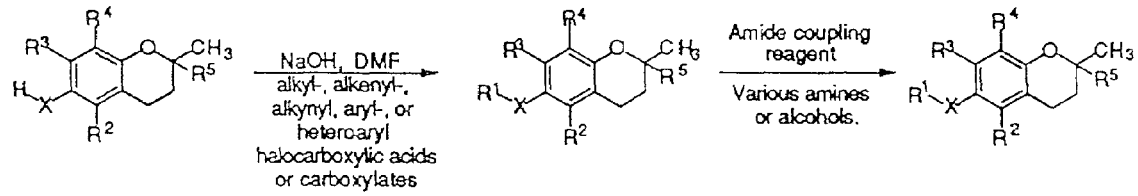
Figure 2A:
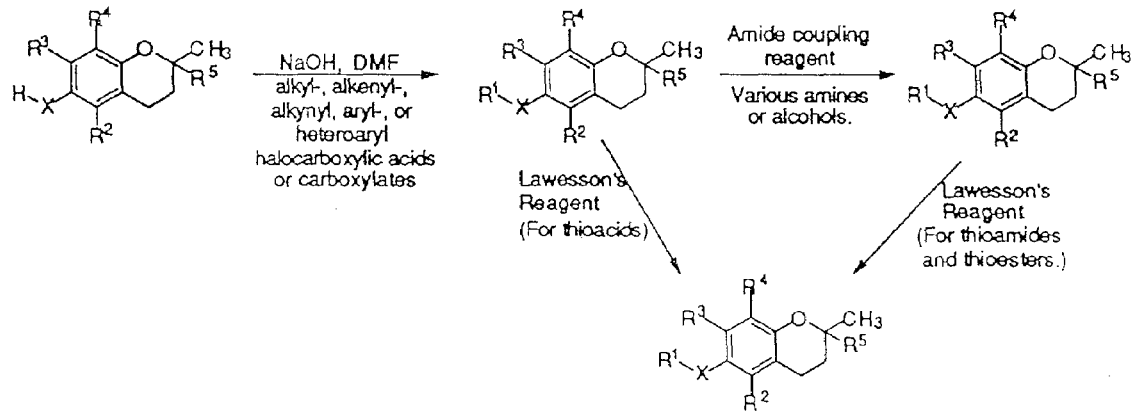
Figure 2B:
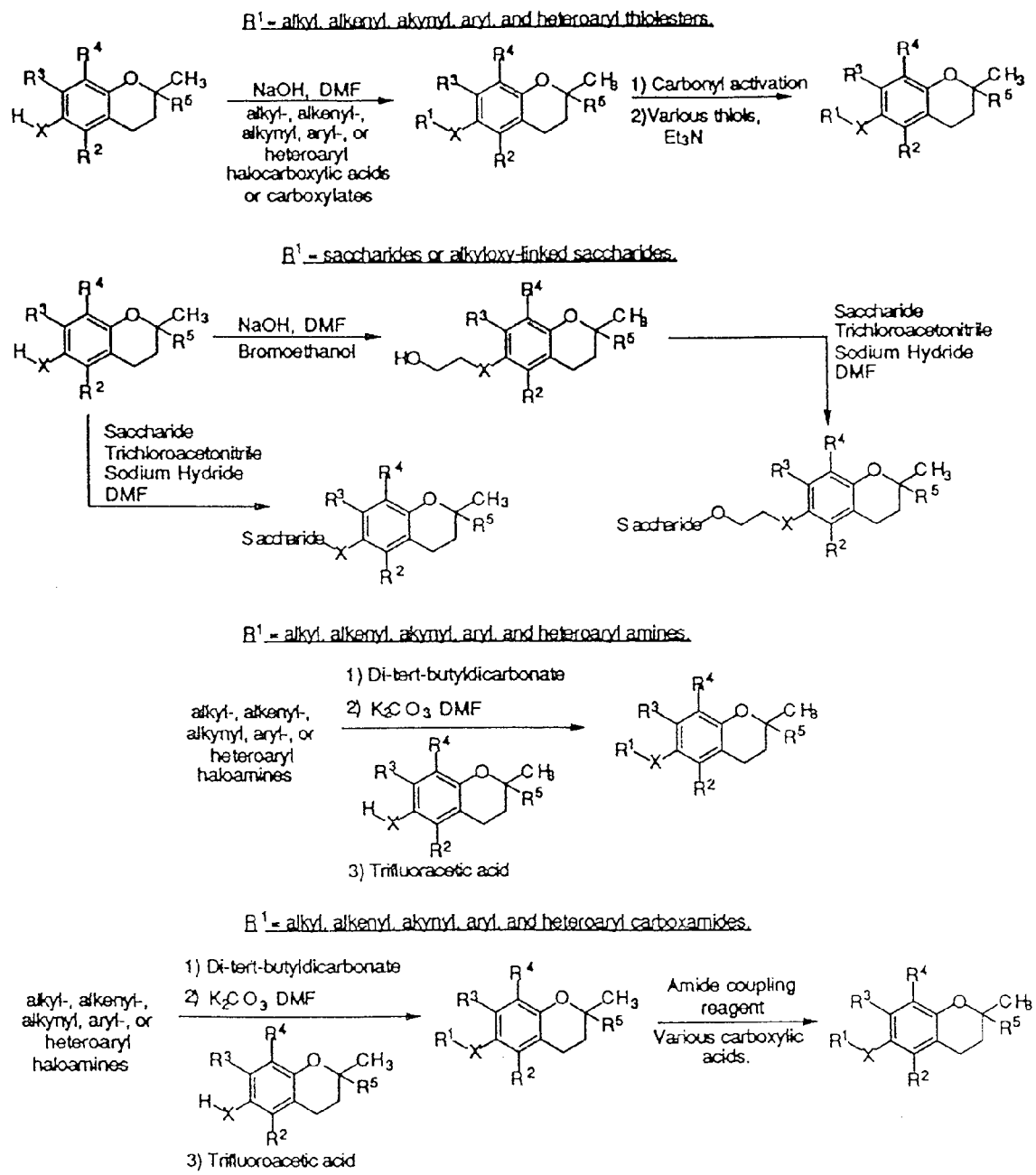
Figure 2C:
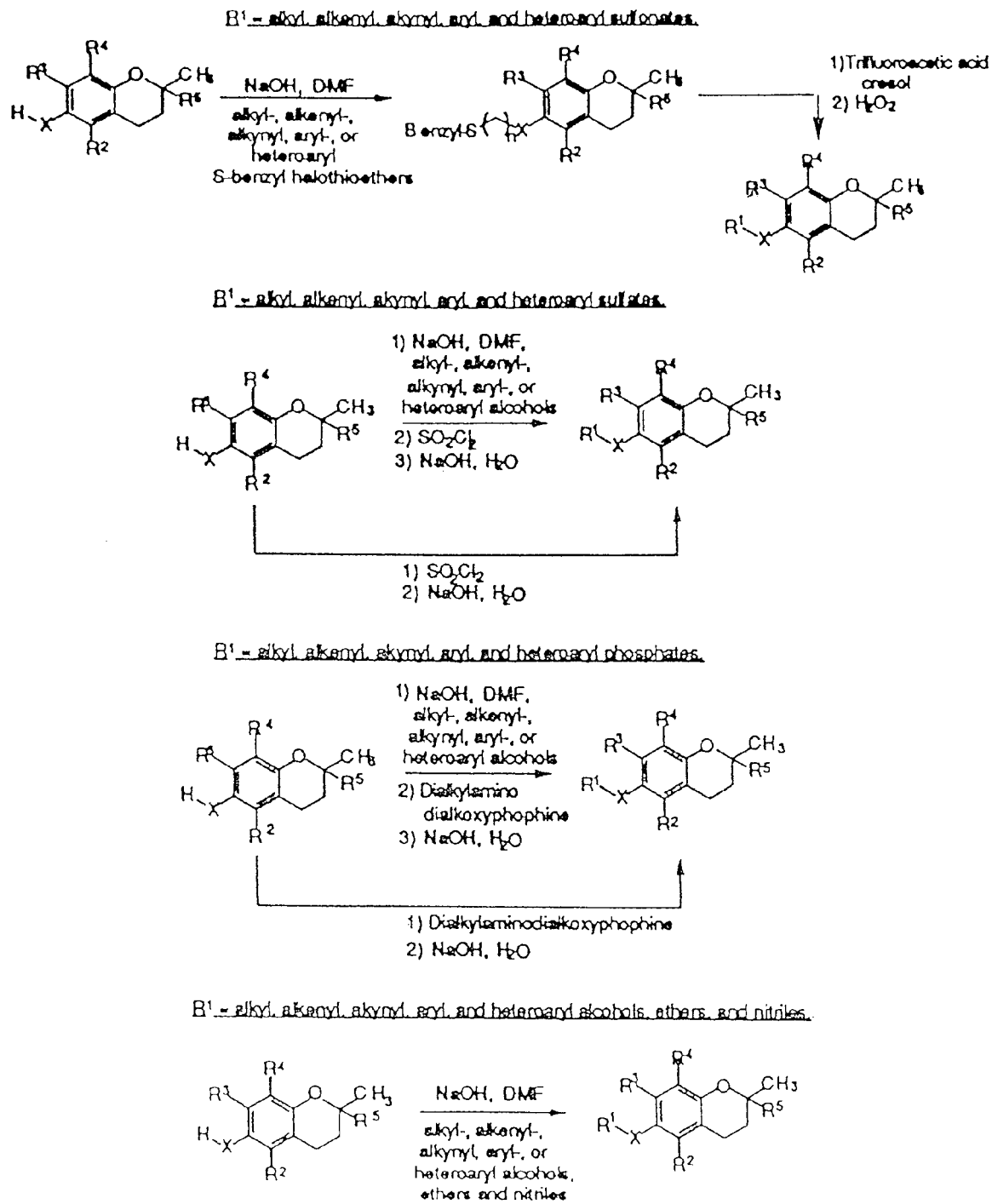
Figure 3:
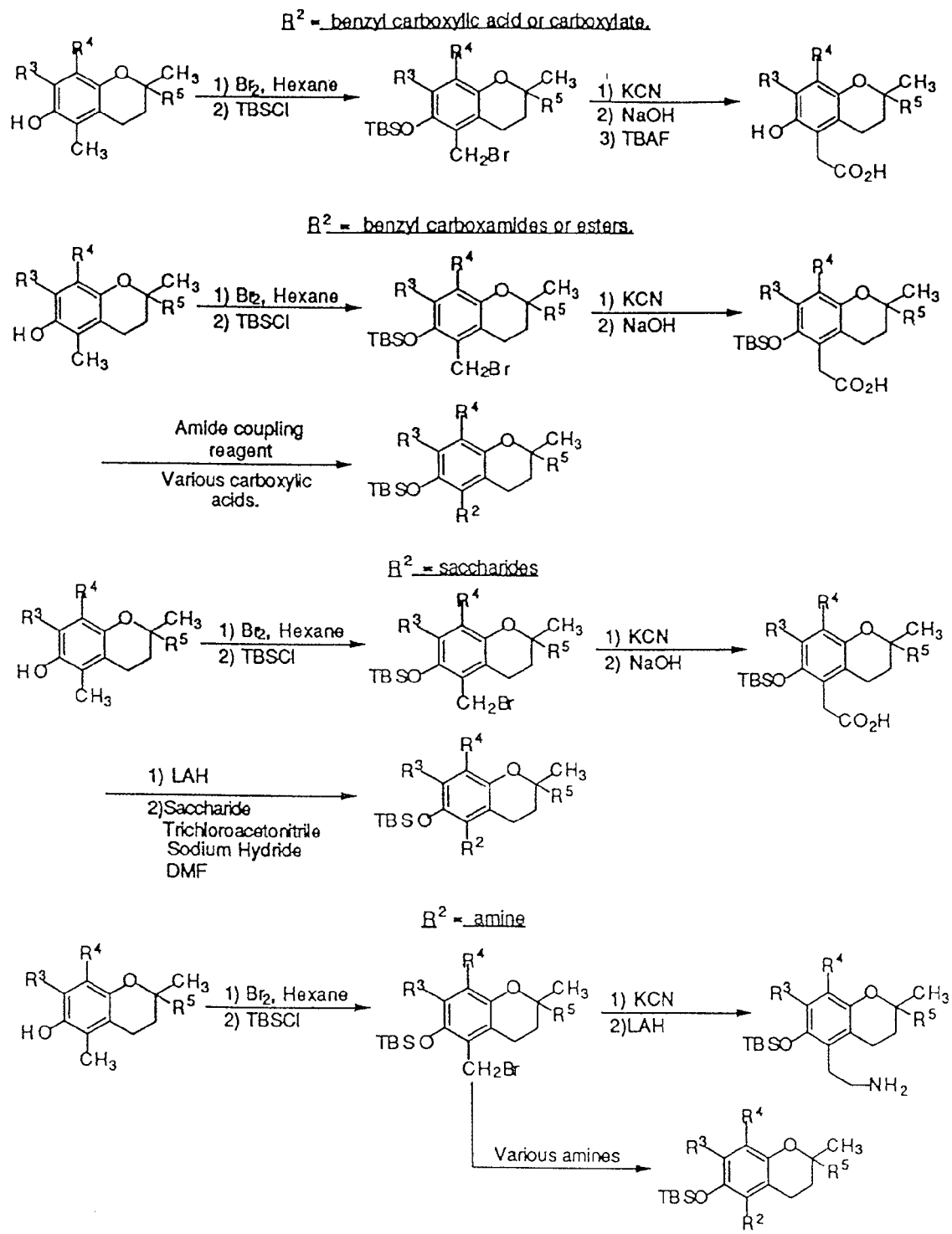
FIG. 3 shows general synthetic organic approaches for the chemical variation of chromanol compounds at position $R^2$.
Figure 4:
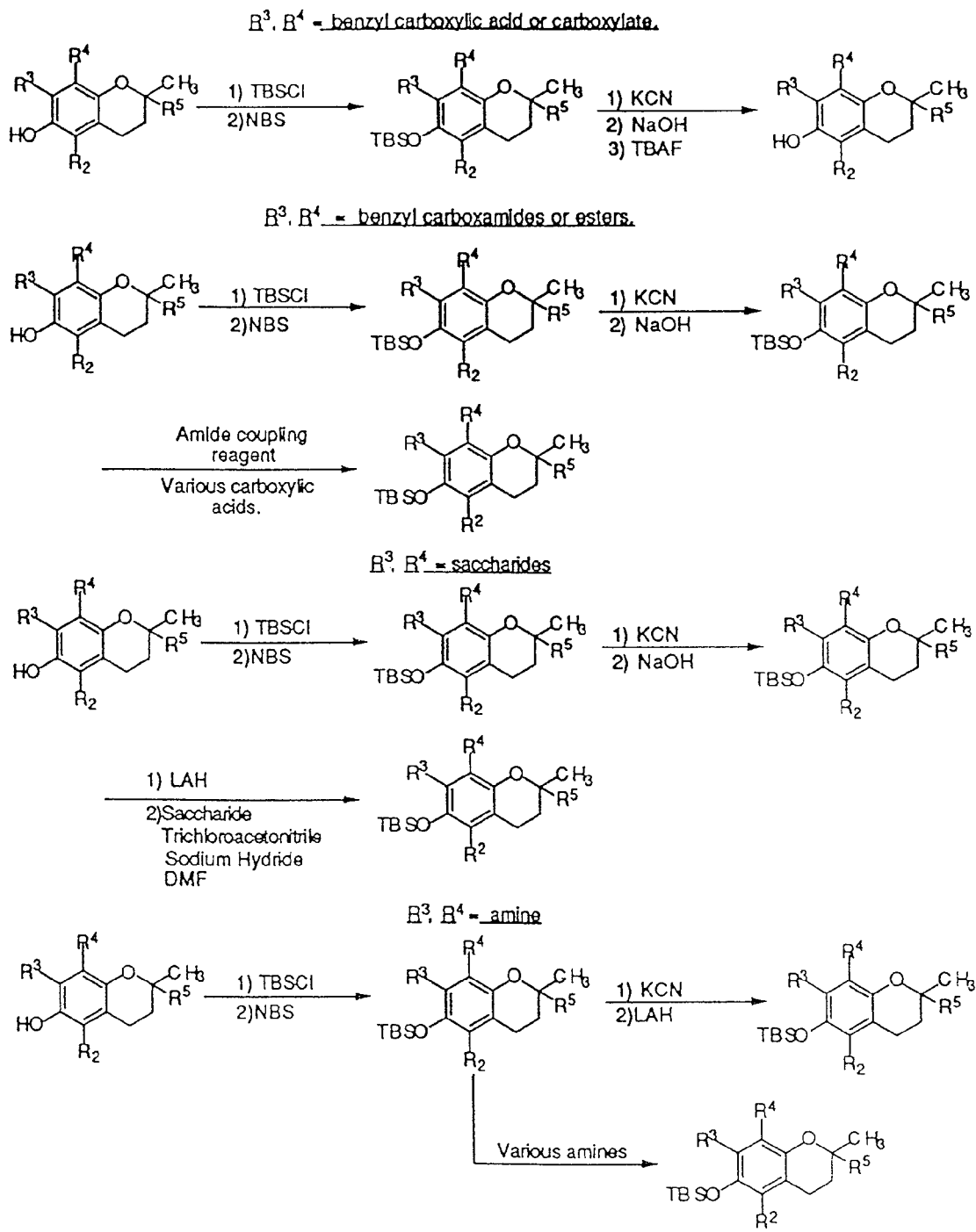
FIG. 4 shows general synthetic organic approaches for the chemical variation of chromanol compounds at position $R^3$ and $R^4$.
Figure 5:
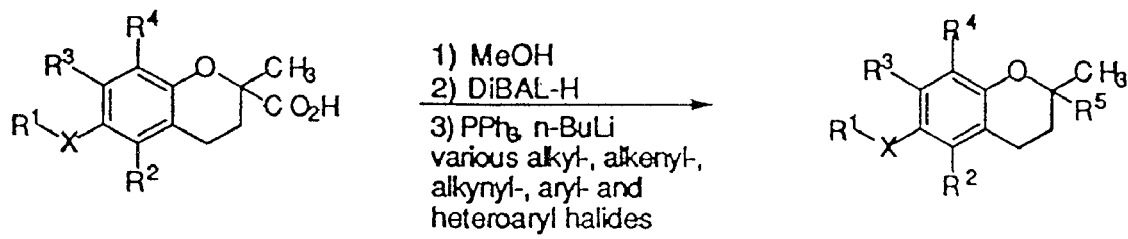
FIG. 5 shows general synthetic organic approaches for the chemical variation of chromanol compounds at position $R^5$.
Figure 5:
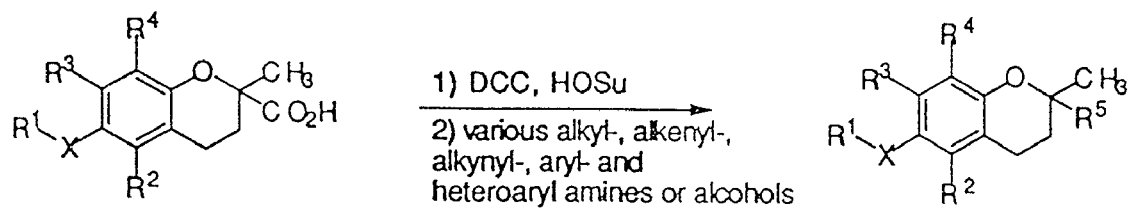

In one embodiment of the present invention, there is provided a compound having a structural formula

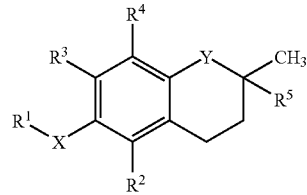

where X and Y independently are oxygen, nitrogen or sulfur; $R^1$ is alkyl, alkenyl, alkynyl, aryl, heteroaryl, carboxylic acid, carboxylate, carboxamide, ester, thioamide, thiolacid, thiolester, saccharide, alkoxy-linked saccharide, amine, sulfonate, sulfate, phosphate, alcohol, ethers or nitrites; $R^2$ and $R^3$ are hydrogen or $R^4$; $R^4$ is methyl, benzyl carboxylic acid, benzyl carboxylate, benzyl carboxamide, benzylester, saccharide or amine; and $R^1$ is alkenyl; where when Y is nitrogen, said nitrogen is substituted with $R^6$, wherein $R^6$ is hydrogen or methyl.

In an aspect of this embodiment the compound has a formula where X and Y are oxygen and $R^1$ is a $C_{7-16}$ olefinic group containing 3 to 5 ethylenic bonds. A representative example of this compound is 6-O-carboxymethyl alpha-tocotrienol. Pharmaceutical compounds comprising the instant compounds and an acceptable pharmaceutical carrier are also provided.

In another embodiment of the present invention there is provided a method for the treatment of a cell proliferative disease comprising administering to an individual a pharmacologically effective dose of a compound having a structural formula

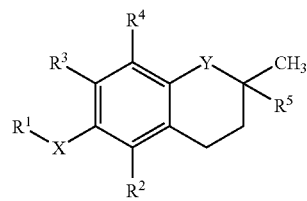

where $R^2$ and $R^3$ are hydrogen or $R^4$; $R^4$ is methyl, benzyl carboxylic acid, benzyl carboxylate, benzyl carboxamide, benzylester, saccharide or amine; and $R^1$ is alkenyl; $R^7$ is hydroxyl or —XR$^1$; wherein R$^1$ is alkyl, alkenyl, alkynyl, aryl, heteroaryl, carboxylic acid, carboxylate, carboxamide, ester, thioamide, thiolacid, thiolester, saccharide, alkoxy-linked saccharide, amine, sulfonate, sulfate, phosphate, alcohol, ethers or nitriles; and X and Y independently are oxygen, nitrogen or sulfur with the proviso that when Y is nitrogen, said nitrogen is substituted with R$^6$, wherein R$^6$ is hydrogen or methyl.

In an aspect of this embodiment, the compound has a formula where Y is oxygen, R$^7$ is hydroxyl or —OR$^1$, and R$^1$ is a C$_{7-16}$ olefinic group containing 3 to 5 ethylenic bonds. Representative examples of these compounds are is α-tocotrienol, γ-tocotrienol, δ-tocotrienol, or 6-O-carboxymethyl α-tocotrienol.

The method of this embodiment may be used to treat an animal. Most preferably, the methods of the present invention are useful in humans. Treatment may be effected by administering a pharmacologically effective dose of the instant compounds of about 1 mg/kg to about 60 mg/kg. Administration of such a dose may be by oral, topical, liposomal/aerosol, intraocular, intranasal, parenteral, intravenous, intramuscular, or subcutaneous delivery. The instant compounds exhibit an anti-proliferative effect; representative examples of these anti-roliferative effects are apoptosis, DNA synthesis arrest, cell cycle arrest, or cellular differentiation.

The compounds and methods of the present invention may be used to treat neoplastic diseases and non-neoplastic diseases. Representative examples of neoplastic diseases are ovarian cancer, cervical cancer, endometrial cancer, bladder cancer, lung cancer, cervical cancer, breast cancer, prostate cancer, testicular cancer, gliomas, fibrosarcomas, retinoblastomas, melanomas, soft tissue sarcomas, osteosarcomas, colon cancer, carcinoma of the kidney, pancreatic cancer, basal cell carcinoma, and squamous cell carcinoma. Representative examples of non-neoplastic diseases are selected from the group consisting of psoriasis, benign proliferative skin diseases, ichthyosis, papilloma, restinosis, scleroderma hemangioma, and leukoplakia.

The compounds and methods of the present invention may be used to treat non-neoplastic diseases that develop due to failure of selected cells to undergo normal programmed cell death or apoptosis. Representative examples of diseases and disorders that occur due to the failure of cells to die are autoimmune diseases. Autoimmune diseases are characterized by immune cell destruction of self cells, tissues and organs. A representative group of autoimmune diseases includes autoimmune thyroiditis, multiple sclerosis, myasthenia gravis, systemic lupus erythematosus, dermatitis herpetiformis, celiac disease, and rheumatoid arthritis. This invention is not limited to autoimmunity, but includes all disorders having an immune component, such as the inflammatory process involved in cardiovascular plaque formation, or ultra violet radiation induced skin damage.

The compounds and methods of the present invention may be used to treat disorders and diseases that develop due to viral infections. Representative examples of diseases and disorders that occur due to viral infections are human immunodeficiency viruses (HIV). Since these compounds are working on intracellular signaling networks, they have the capacity to impact signal transduction of any type of external cellular signal such as cytokines, viruses, bacteria, toxins, heavy metals, etc.

In yet another embodiment of the present invention there is provided a method of inducing apoptosis of a cell using the compounds disclosed supra. In an aspect of this embodiment the method may be used to treat a cell proliferative disease.

The following definitions are given for the purpose of facilitating understanding of the inventions disclosed herein. Any terms not specifically defined should be interpreted according to the common meaning of the term in the art.

As used herein, the term "individual" shall refer to animals and humans.

As used herein, the term "biologically inhibiting" or "inhibition" of the growth of proliferating cells shall include partial or total growth inhibition and also is meant to include decreases in the rate of proliferation or growth of the cells. The biologically inhibitory dose of the composition of the present invention may be determined by assessing the effects of the test element on target malignant or abnormally proliferating cell growth in tissue culture, tumor growth in animals and cell culture or any other method known to those of ordinary skill in the art.

As used herein, the term "induction of programmed cell death or apoptosis" shall include partial or total cell death with cells exhibiting established morphological and biochemical apoptotic characteristics. The dose of the composition of the present invention that induces apoptosis may be determined by assessing the effects of the test element on target malignant or abnormally proliferating cell growth in tissue culture, tumor growth in animals and cell culture or any other method known to those of ordinary skill in the art.

As used herein, the term "induction of cell cycle arrest" shall include growth arrest due to treated cells being blocked in G0/G1 or G2/M cell cycle phase. The dose of the composition of the present invention that induces cell cycle arrest may be determined by assessing the effects of the test element on target malignant or abnormally proliferating cell growth in tissue culture, tumor growth in animals and cell culture or any other method known to those of ordinary skill in the art.

As used herein, the term "induction of cellular differentiation" shall include growth arrest due to treated cells being induced to undergo cellular differentiation as defined by established morphological and biochemical differentiation characterization, a stage in which cellular proliferation does not occur. The dose of the composition of the present invention that induces cellular differentiation may be determined by assessing the effects of the test element on target malignant or abnormally proliferating cell growth in tissue culture, tumor growth in animals and cell culture or any other method known to those of ordinary skill in the art.

As used herein, the term "growth inhibitory concentration (IC$_{50}$)" or "effective concentration (EC$_{50}$)" shall include the effective therapeutic dose of a compound or composition for controlling cancer growth, i.e., by blocking 50% cancer growth via DNA synthesis inhibition, cellular differentiation, cell cycle blockage and/or cell death.

Naturally occurring alpha-, gamma-, and delta tocotrienols, as well as gamma- and delta-tocopherols exhibit anticancer activity. Alpha-tocopherol does not exhibit anticancer activity. The present invention provides tocopherols, tocotrienols, and other chroman derivatives with or without derivatives of saturated phytyl or unsaturated isoprenyl side chains and analogs; e.g., azo- and thiol-analogs, thereof. Construction of RRR-alpha-tocopherol or RRR-alpha-tocotrienol based compounds with a succinate or modified succinate moiety attached to the C6 position of the first ring of the chromonal head of alpha-tocopherol or alpha-tocotrienol via an ether linkage provides novel compounds with potent anticancer properties, for in vivo use, are produced. The lack of cellular etherases in mammals insures the efficacy of these compounds. The general structures of the natural tocopherols and tocotrienols of the present invention are shown in FIG. 1, and possible routes for their syntheses are provided in FIGS. 2-5.

Figure 6A:
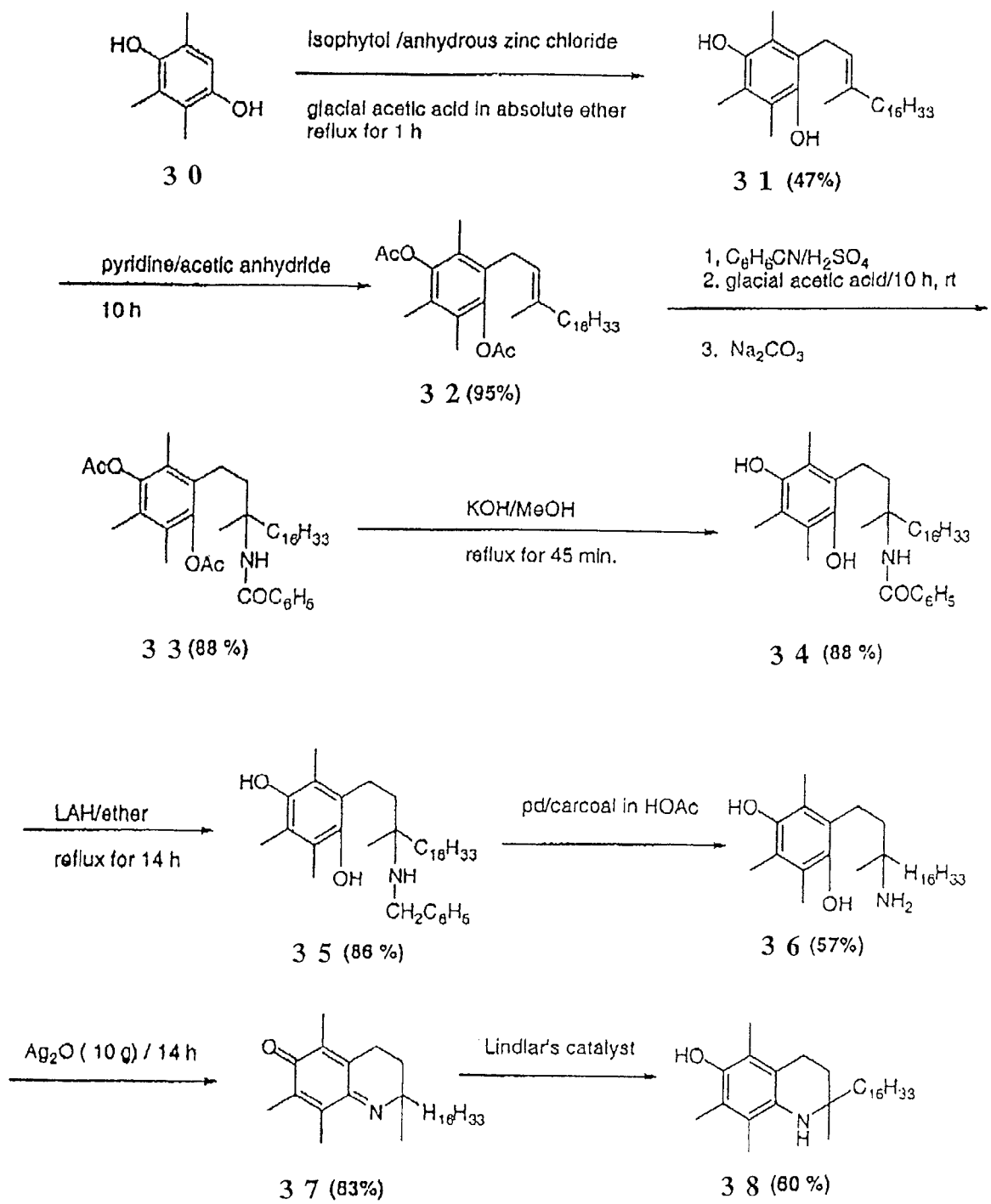
FIGS. 6A-6B shows general synthetic organic approaches for the all-racemic 1-aza-α-tocopherol analogs.
Figure 6B:
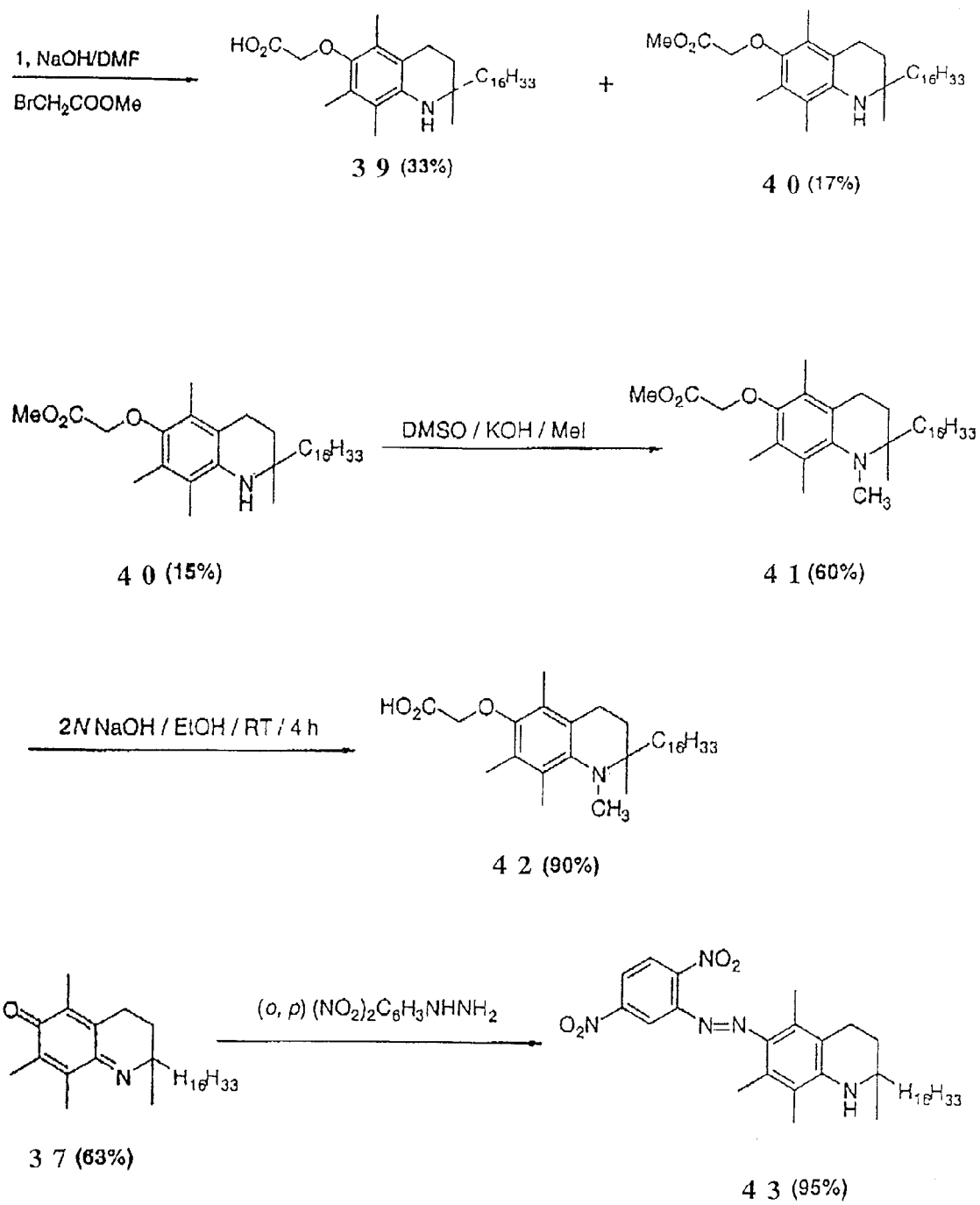

These molecules include chemical funtionalization of positions $R^1$—$R^1$ of the chroman structure, and chemical functionalization of the phytyl and isoprenyl side chains, particularly compounds based on tocopherols and tocotrienols. Additionally, compounds with heteroatom substitutions (N or S) for the chroman ring oxygen are presented (FIG. 6A-6B).

The pharmacodynamically designed compounds of the present invention have an improved therapeutic index and are potent inhibitors of cancer cell growth; i.e., they demonstrate high antitumor activity with minimal side effects. These compounds, which can not be readily degraded since there are no known etherases in mammals, may be used in the treatment of cancers and disorders involving excess cell proliferation, as well as for cells that accumulate in numbers due to suppressed cell killing mechanisms, with minimal side effects. The compounds of the present invention inhibit cancer cell growth by induction of cell differentiation, induction of apoptosis and DNA synthesis arrest. Induction of apoptosis and, by extension, inhibition of tumor growth, by these compounds is via modulation of the transforming growth factor-beta (TGF-β), Fas/Fas ligand, and certain mitogen-activated protein kinases (MAPK) signaling pathways, or, in the case of some tocotrienols, is expected to involve these pathways. Induction of apoptosis via other pathways, such as ceramide production, is not excluded. These growth inhibitory properties allow these compounds to be used in the treatment of proliferative diseases, including cancers of different cell types and lineages, non-neoplastic hyperproliferative diseases, and disorders with defects in apoptotic signaling pathways. Several of the compounds of the present invention are both strong inducers of apoptosis and strong inhibitors of DNA synthesis arrest of tumor cells representing different cellular lineages.

The therapeutic use of the compounds of the present invention in treatment of cancers and other diseases and disorders involving excess cell proliferation or failure of cells to die is illustrated. The novel derivatives (Tables 2-1/2-2 and 3-1/3-2) are shown at $EC_{50}$ concentrations to induce apoptosis of human breast cancer cells (MDA MB 435, MDA MB 231, and MCF-7 breast cancer cells), human prostate cancer cells (PC-3, DU-145 and LnCaP), human ovarian tumor cells (C-170), human cervical tumor cells (ME-180), human endometrial cells (RL-95-2), human lymphoid cells (myeloma, Raji, Ramos, Jurkat, and HL-60), colon cancer cells (HT-29 and DLD-1) and lung cancer cells (A-549). The novel derivatives were shown to not induce apoptosis of normal human mammary epithelial cells (HMECs) and immortalized but non-tumorigenic MCF-10A mammary cells.

Generally, to achieve pharmacologically efficacious cell killing and anti-proliferative effects, these compounds and analogs thereof may be administered in any therapeutically effective dose. Preferably, the structurally modified tocopherols and tocotrienols and analogs are administered in a dose of from about 0.1 mg/kg to about 100 mg/kg. More preferably, the structurally modified tocopherols and tocotrienols and analogs are administered in a dose of from about 1 mg/kg to about 10 mg/kg.

Administration of the compounds and compositions of the present invention may be by liposome/aerosol, topical, intraocular, parenteral, oral, intranasal, intravenous, intramuscular, subcutaneous, or any other suitable means. The dosage administered is dependent upon the age, clinical stage and extent of the disease or genetic predisposition of the individual, location, weight, kind of concurrent treatment, if any, and nature of the pathological or malignant condition. The effective delivery system useful in the method of the present invention may be employed in such forms as liposomal aerosol, capsules, tablets, liquid solutions, suspensions, or elixirs, for oral administration, or sterile liquid forms such as solutions, suspensions or emulsions. For topical use it may be employed in such forms as ointments, creams or sprays. Any inert carrier is preferably used in combination with suitable solubilizing agents, such as saline, or phosphate-buffered saline, or any such carrier in which the compounds used in the method, such as ethanol, acetone, or DMSO, of the present invention have suitable solubility properties.

There are a wide variety of pathological cancerous and noncancerous cell proliferative conditions and cell accumulations due to absence of normal cellular death for which the compositions and methods of the present invention will provide therapeutic benefits. These pathological conditions may occur in almost all cell types capable of abnormal cell proliferation or defective in programmed cell death mechanisms. Among the cell types which exhibit pathological or abnormal growth or abnormal death are (1) fibroblasts, (2) vascular endothelial cells and (3) epithelial cells. It can be seen from the above that the methods of the present invention is useful in treating local or disseminated pathological conditions in all or almost all organ and tissue systems of individuals.

It is specifically contemplated that pharmaceutical compositions may be prepared using the novel chroman-based compounds and derivatives and analogs thereof of the present invention. In such a case, the pharmaceutical composition comprises the novel compounds of the present invention and a pharmaceutically acceptable carrier. A person having ordinary skill in this art would readily be able to determine, without undue experimentation, the appropriate dosages and routes of administration of the compounds and analogs of the present invention.

Thus the present invention is directed toward the design and effective use of novel agents that can specifically target cancer cells and either down-regulate growth stimulatory signals, up-regulate growth inhibitory signals, down-regulate survival signals and/or up-regulate death signals. More specifically, this invention creates and characterizes novel agents that activate growth inhibitory factors, trigger death signaling pathways, and inhibit DNA synthesis.

The following examples are given for the purpose of illustrating various embodiments of the invention and are not meant to limit the present invention in any fashion.

EXAMPLE 1

Synthetic Organic Methodology

The synthesis of a variety of tocopherol, tocotrienol, and other chroman derivatives with or without derivatives of saturated phytyl or unsaturated isoprenyl side chains or analogs thereof is possible via structural modification of the chroman ring system (FIGS. 2-5) and heteroatom substitutions (N or S) for the chroman ring oxygen (FIG. 6A-6B). The structural variables $R^1$, $R^2$, $R^3$, $R^4$, $R^5$, $R^7$ and X illustrate the groups on the chroman group that are modified and Y represents either oxygen, or heteroatom substitutions (N or S) for the chroman ring oxygen. In naturally occurring α-, β-, γ-, δ-tocopherols and α-, β-, γ-, δ-tocotrienols, the X—$R^1$ substituent at the six position of the chroman ring is hydroxyl; in a general structure this is represented by $R^7$. When Y is nitrogen, it may be substituted with a structural variable $R^6$, e.g., hydrogen or methyl.

Using alkylation chemistry, a large number of compounds containing different $R^1$ groups can be synthesized, particularly when X is oxygen. After alkylation, further chemical modification of the $R^1$ groups permits the synthesis of a wide range of novel compounds. R1 substituents can be alkyl, alkenyl, alkynyl, aryl, heteroaryl, carboxylic acid, carboxylate, carboxamide, ester, thioamide, thiolacid, thiolester, saccharide, alkoxy-linked saccharide, amine, sulfonate, sulfate, phosphate, alcohol, ethers and nitrites.

Bromination of the benzylic methyl groups of the chroman group provide intermediates that permit variation of the $R^2$, $R^3$ and $R^4$ groups. Substituents for $R^2$ and $R^3$ may be hydrogen or those substituents for $R^4$, e.g., methyl, benzyl carboxylic acid, benzyl carboxylate, benzyl carboxamide, benzylester, saccharide and amine. Variation of group $R^5$, such as alkyl, alkenyl, alkynyl, aryl, heteroaryl, carboxyl, amide and ester, is also possible, particularly when starting from the commercially available 6-hydroxy-2,5,7,8-tetramethylchroman-2-carboxylic acid.

When a heteroatom substitution of nitrogen for the chroman ring oxygen occurs, the nitrogen may be substituted with $R^6$ which is hydrogen or methyl. Variation of X to groups other than oxygen, which is the identity of X in tocopherols and tocotrienols, can be accomplished using palladium chemistry (for X=$CH_2$) and nucleophilic aromatic substitution (for X=N or S). Other possible modifications to the chroman structure include unsaturation at the 3-4 positions and ring contraction to produce a five-membered furanyl ring.

Reagents employed were either commercially available or prepared according to a known procedure. Anhydrous $CH_2Cl_2$ and THF were obtained by distillation. All other solvents used were reagent. Anhydrous reaction conditions were maintained under a slightly positive argon atmosphere in oven-dried glassware. Silica gel chromatography was performed using 230-400 mesh silica for tocopherol compounds and 70-200 mesh silica for tocotrienol compounds purchased from EM Science. Routine $^1$H- and $^{13}$C-NMR spectra were obtained on a Varian Unity spectrometer at 300.132 MHz and 75.033 MHz frequencies, respectively. NMR spectra were referenced to TMS (0 ppm) or to the isotopic impurity peak of $CDCl_3$ (7.26 and 77.0 ppm for $^1$H and $^{13}$C, respectively). High resolution electron impact ionization mass spectroscopy was performed by the Mass Spectrometry Center at The University of Texas at Austin.

EXAMPLE 2

Synthesis and characterization of tocopherol compounds 2,5,7,8-tetramethyl-(2R-(4R,8R,12-trimethyltridecyl)chroman-6-yloxy)acetic acid (1)

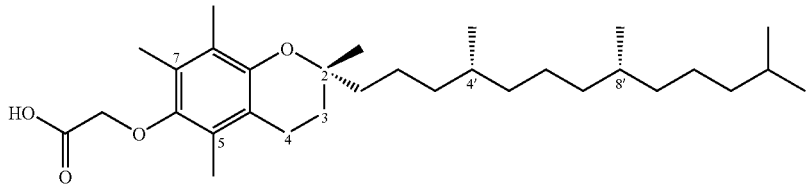

A solution of R,R,R-α-tocopherol (0.5 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with $H_2O$ (3×30 ml) and brine (1×30 ml), and then dried with $Na_2SO_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with $H_2O$ (3×20 mL) and brine (1×20 mL), and then dried with $Na_2SO_4$. The resulting solution was concentrated to a light yellow oil and dried in vacuo for 48 h. This yielded 1 as a waxy, off-white solid (0.50 g, 88%). $^1$H-NMR ($CDCl_3$/TMS, ppm): 0.87 (m, 12H, 4a'-, 8a'-, 12a'-, 13'-$CH_3$), 1.0-1.6 (m, 24H, 4'-, 8'-, 12'-CH, 1'-, 2'-, 3'-, 5'-, 6'-, 7'-, 9'-, 10'-, 1'-$CH_2$, 2a-$CH_3$), 1.81 (m, 2H, 3-$CH_2$), 2.07, 2.14, 2.16 (3×s, 9H, 5a-, 7a-, 8a-$CH_3$), 2.59 (t, J=6.6 Hz, 2H, 4-$CH_2$), 4.34 (s, 2H, $OCH_2$); $^{13}$C-NMR ($CDCl_3$, ppm): 11.7, 11.8, 12.7 (5a-, 7a-, 8a-$CH_3$), 19.6, 19.7 ($CH_3$), 20.6, 21.0 ($CH_2$), 22.6, 22.7 ($CH_3$), 23.8 (2a-$CH_3$), 24.4, 24.8 ($CH_2$), 28.0 (CH), 31.2 (3-$CH_2$), 32.7, 32.8 (CH), 37.3, 37.4, 37.5, 39.4, 40.0 ($CH_2$), 69.2 ($OCH_2$), 75.0 (2-C), 117.8, 123.2, 125.4, 127.3 (aryl C), 147.0, 148.5 (aryl C—O), 173.7 (COOH); HRMS (CI, m/z): 489.394374 (M+H$^+$, Calc. for $C_{31}H_{53}O_4$ 489.394386). All assignments were confirmed using HMQC, DEPT-135, and $^1$H-NOSEY.

2,5,7,8-tetramethyl-(2R-(4R,8R,12-trimethyltridecyl) chroman-6-yloxy) propionic acid (2)

The compounds 2-6 are synthesized in a manner identical to the synthesis of 1 using the appropriate bromoalkanoic acids.

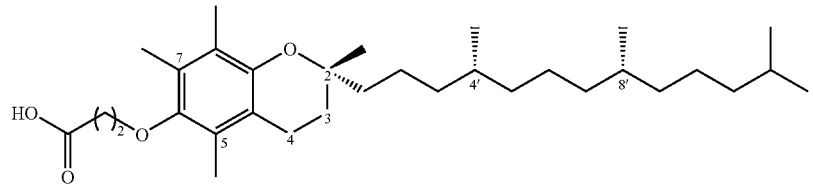

(89% yield). $^1$H-NMR (CDCl$_3$/TMS, ppm): 0.87 (m, 12H, 4a'-, 8a'-, 12a'-, 13'-CH$_3$), 1.0-1.6 (m, 24H, 4'-, 8'-, 12'-CH, 1'-, 2'-, 3'-, 5'-, 6'-, 7'-, 9'-, 10'-, 11'-CH$_2$, 2a-CH$_3$), 1.81 (m, 2H, 3-CH$_2$), 2.09, 2.14, 2.19 (3×s, 9H, 5a-, 7a-, 8a-CH$_3$), 2.59 (t, J=6.6 Hz, 2H, 4-CH$_2$), 2.85 (t, J=6.4 Hz, 2H, CH$_2$COOH), 3.96 (t, J=6.4 Hz, 2H, OCH$_2$); $^{13}$C-NMR (CDCl$_3$, ppm): 11.7, 11.8, 12.7 (5a-, 7a-, 8a-CH$_3$), 19.6, 19.7 (CH$_3$), 20.6, 21.0 (CH$_2$), 22.6, 22.7 (CH$_3$), 23.8 (2a-CH$_3$), 24.4, 24.8 (CH$_2$), 28.0 (CH), 31.2 (3-CH$_2$), 32.7, 32.8 (CH), 35.1, 37.3, 37.4, 37.5, 39.4, 40.0 (CH$_2$), 67.5 (OCH$_2$), 74.8 (2-C), 117.5, 122.9, 125.8, 127.8 (aryl C), 147.6, 148.0 (aryl C—O), 177.1 (COOH); HRMS (CI, m/z): 503.408610 (M+H$^+$, Calc. for C$_{32}$H$_{55}$O$_4$ 503.410036).

2,5,7,8-tetramethyl-(2R-(4R,8R,12-trimethyltridecyl) chroman-6-yloxy) butyric acid (3)

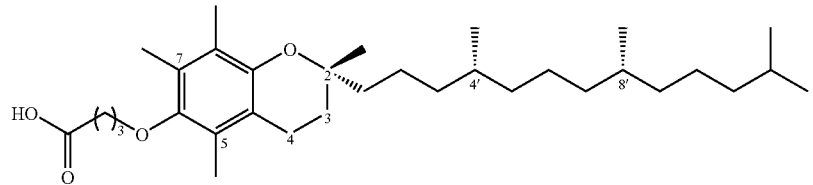

(85% yield). $^1$H-NMR (CDCl$_3$/TMS, ppm): 0.87 (m, 12H, 4a'-, 8a'-, 12a'-, 13'-CH$_3$), 1.0-1.6 (m, 26H, 4'-, 8'-, 12'-CH, 1'-,2'-,3'-,5'-,6'-,7'-,9'-,10'-,11'-CH$_2$, 2a-CH$_3$), 1.81 (m, 2H, 3-CH$_2$), 2.14, 2.17, 2.21 (3×s, 9H, 5a-, 7a-, 8a-CH$_3$), 2.62 (t, J=6.6 Hz, 2H, 4-CH$_2$), 2.72 (t, J=7.2 Hz, 2H, CH$_2$COOH), 3.74 (t, J=6.1 Hz, 2H, OCH$_2$); $^{13}$C-NMR (CDCl$_3$, ppm): 11.7, 11.8, 12.7 (5a-, 7a-, 8a-CH$_3$), 19.6, 19.7 (CH$_3$), 20.6, 21.0 (CH$_2$), 22.6, 22.7 (CH$_3$), 23.9 (2a-CH$_3$), 24.4, 24.8, 25.3 (CH$_2$), 28.0 (CH), 30.9, 31.2 (3-CH$_2$), 32.7, 32.8 (CH), 37.3, 37.4, 37.5, 39.4, 40.0 (CH$_2$), 71.3 (OCH$_2$), 74.8 (2-C), 117.5, 122.9, 125.7, 127.7 (aryl C), 147.8, 147.9 (aryl C—O), 178.9 (COOH); HRMS (CI, m/z): 516.424374 (M+H$^+$, Calc. for C$_{33}$H$_{57}$O$_4$ 516.424386).

2,5,7,8-tetramethyl-2R-(4R,5R,2-trimethyltridecyl) chroman-6-yloxy) valeric acid (4)

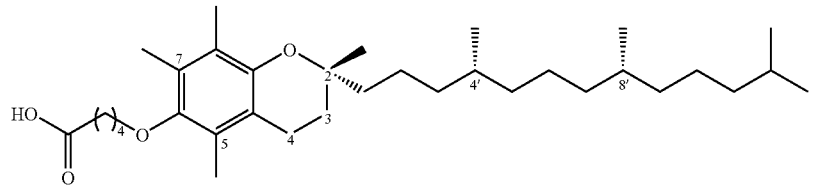

(90% yield). $^1$H-NMR (CDCl$_3$/TMS, ppm): 0.87 (m, 12H, 4a'-, 8a'-, 12a'-, 13'-CH$_3$), 1.0-1.6 (m, 28H, 4'-, 8'-, 12'-CH, 1'-, 2'-, 3'-, 5'-, 6'-, 7'-, 9'-, 10'-, 11'-CH$_2$, 2a-CH$_3$), 1.81 (m, 2H, 3-CH$_2$), 2.09, 2.14, 2.18 (3×s, 9H, 5a-, 7a-, 8a-CH$_3$), 2.49 (t, J=6.8 Hz, 2H, CH$_2$COOH), 2.59 (t, J=6.6 Hz, 2H, 4-CH$_2$), 3.68 (t, J=5.5 Hz, 2H, OCH$_2$); $^{13}$C-NMR (CDCl$_3$, ppm): 11.7, 11.8, 12.7 (5a-, 7a-, 8a-CH$_3$), 19.6, 19.7 (CH$_3$), 20.6, 21.0, 21.4 (CH$_2$), 22.6, 22.7 (CH$_3$), 23.8 (2a-CH$_3$), 24.4, 24.8 (CH$_2$), 28.0 (CH), 30.0 (CH$_2$), 31.2 (3-CH$_2$), 32.7, 32.8 (CH), 35.8, 37.3, 37.4, 37.5, 39.4, 40.0 (CH$_2$), 72.2 (OCH$_2$), 74.9 (2-C), 117.8, 123.2, 125.4, 127.3 (aryl C), 147.6, 148.3 (aryl C—O), 178.7 (COOH); HRMS (CI, m/z): 530.433514 (M+H$^+$, Calc. for C$_{34}$H$_{59}$O$_4$ 530.433516).

2,5,7,8-tetramethyl-2R-(4R,8R,12-trimethyl tridecyl) chroman-6-yloxy) hexanoic acid (5)

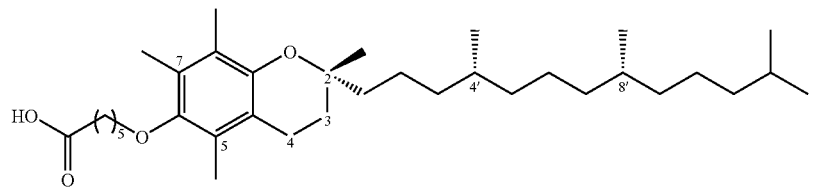

(77% yield). $^1$H-NMR (CDCl$_3$/TMS, ppm): 0.87 (m, 12H, 4a'-, 8a'-, 12a'-, 13'-CH$_3$), 1.0-1.6 (m, 30H, 4'-, 8'-, 12'-CH, 1'-, 2'-, 3'-, 5'-, 6'-, 7'-, 9'-, 10'-, 11'-CH$_2$, 2a-CH$_3$), 1.81 (m, 2H, 3-CH$_2$), 2.08, 2.12, 2.16 (3×s, 9H, 5a-, 7a-, 8a-CH$_3$), 2.32 (t, J=6.5 Hz, 2H, CH$_2$COOH), 2.57 (t, J=6.6 Hz, 2H, 4-CH$_2$), 3.64 (t, J=5.5 Hz, 2H, OCH$_2$); $^{13}$C-NMR (CDCl$_3$, ppm): 11.8, 11.9, 12.7 (5a-, 7a-, 8a-CH$_3$), 19.6, 19.7 (CH$_3$), 20.6, 21.0 (CH$_2$), 22.6, 22.7 (CH$_3$), 23.8 (2a-CH$_3$), 24.4, 24.6, 24.8, 25.7 (CH$_2$), 28.0 (CH), 30.0 (CH$_2$), 31.3 (3-CH$_2$), 32.7, 32.8 (CH), 34.0, 37.3, 37.3, 37.4, 39.3, 40.0 (CH$_2$), 72.6 (OCH$_2$), 74.7 (2-C), 117.4, 122.7, 125.4, 127.8 (aryl C), 147.6, 148.2 (aryl C—O), 179.6 (COOH); HRMS (CI, m/z): 545.457026 (M+H$^+$, Calc. for C$_{35}$H$_{61}$O$_4$ 545.456986).

2,5,7,8-tetramethyl-2R-(4R,8R,12-trimethyltridecyl) chroman-6-yloxy) octanoic acid (6)

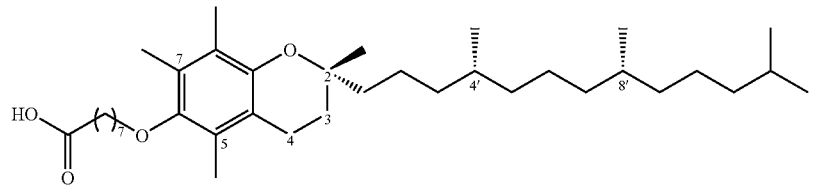

(91% yield). $^1$H-NMR (CDCl$_3$/TMS, ppm): 0.87 (m, 12H, 4a'-, 8a'-, 12a'-, 13'-CH$_3$), 1.0-1.6 (m, 34H, 4'-, 8'-, 12'-CH, 1'-, 2'-, 3'-, 5'-, 6'-, 7'-, 9'-, 10'-, 11'-CH$_2$, 2a-CH$_3$), 1.81 (m, 2H, 3-CH$_2$), 2.08, 2.11, 2.16 (3×s, 9H, 5a-, 7a-, 8a-CH$_3$), 2.36 (m, 2H, CH$_2$COOH), 2.58 (t, J=6.6 Hz, 2H, 4-CH$_2$), 3.62 (t, J=5.5 Hz, 2H, OCH$_2$); $^{13}$C-NMR (CDCl$_3$, ppm): 11.7, 11.8, 12.7 (5a-, 7a-, 8a-CH$_3$), 19.6, 19.7 (CH$_3$), 20.6, 21.0 (CH$_2$), 22.6, 22.7 (CH$_3$), 23.8 (2a-CH$_3$), 24.4, 24.6, 24.8, 25.1, 25.7, 26.6 (CH$_2$), 28.0 (CH), 30.0 (CH$_2$), 31.3 (3-CH$_2$), 32.7, 32.8 (CH), 34.0, 37.3, 37.3, 37.4, 39.3, 40.0 (CH$_2$), 72.7 (OCH$_2$), 74.6 (2-C), 117.6, 122.8, 125.5, 127.6 (aryl C), 147.5, 148.3 (aryl C—O), 179.4, (COOH); HRMS (CI, m/z): 573.484396 (M+H$^+$, Calc. for C$_{37}$H$_{65}$O$_4$ 573.488286).

2,5,8-trimethyl-(2R-(4R,8R,12-trimethyltridecyl)
chroman-6-yloxy)acetic acid (7)

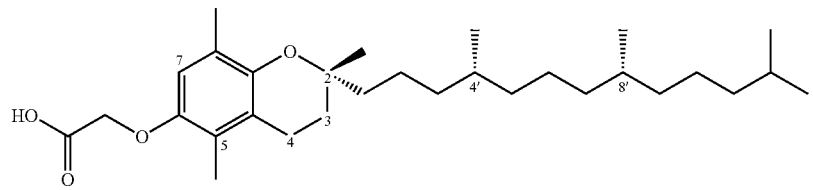

A solution of R,R,R-α-tocopherol (75 mg, 0.18 mmol) in N,N-dimethylformamide (2 mL) was treated with methyl bromoacetate (0.4 g, 2.8 mmol) and an excess of powdered NaOH (0.5 g, 12.5 mmol). The resulting yellow slurry was stirred vigorously for 24 h at room temperature. The reaction was acidified with 5 N HCl and extracted with diethyl ether (3×10 ml). The combined ether layers were washed with $H_2O$ (3×10 ml) and brine (1×10 ml), and then dried with $Na_2SO_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with $H_2O$ (3×10 mL) and brine (1×10 mL), and then dried with $Na_2SO_4$. The resulting solution was concentrated to a light yellow oil and dried in vacuo for 48 h. This yielded 7 as a waxy, off-white solid (80 mg, 97%). $^1$H-NMR ($CDCl_3$/TMS, ppm): 0.87 (m, 12H, 4a'-, 8a'-, 12a'-, 13'-$CH_3$), 1.0-1.6 (m, 24H, 4'-, 8'-, 12'-CH, 1'-, 2'-, 3'-, 5'-, 6'-, 7'-, 9'-, 10'-, 11'-$CH_2$, 2a-$CH_3$), 1.81 (m, 2H, 3-$CH_2$), 2.12, 2.14 (2×s, 6H, 5a-, 8a-$CH_3$), 2.61 (t, J=6.6 Hz, 2H, 4-$CH_2$), 4.59 (s, 2H, $OCH_2$), 6.53 (s, 1H, aryl CH); $^{13}$C-NMR ($CDCl_3$, ppm): 11.2, 16.1 (5a-, 8a-$CH_3$), 19.6, 19.7 ($CH_3$), 20.7, 21.0 ($CH_2$), 22.6, 22.7 ($CH_3$), 23.8 (2a-$CH_3$), 24.4, 24.8 ($CH_2$), 27.9 (CH), 31.2 (3-$CH_2$), 32.7, 32.8 (CH), 37.2, 37.4, 37.5, 39.4, 40.0 ($CH_2$), 66.8 ($OCH_2$), 74.8 (2-C), 113.8, 120.7, 123.1, 127.3 (aryl C), 147.1, 148.2 (aryl C—O), 175.3 (COOH); HRMS (CI, m/z): 475.377840 (M+H$^+$, Calc. for $C_{30}H_{51}O_4$ 475.378736).

2,7,8-trimethyl-(2R-(4R,8R,12-trimethyltridecyl)
chroman-6-yloxy)acetic acid (8)

A solution of R,R,R-α-tocopherol (100 mg, 0.24 mmol) in N,N-dimethylformamide (5 mL) was treated with methyl bromoacetate (1.1 g, 7.4 mmol) and an excess of powdered NaOH (1.0 g, 25 mmol). The resulting yellow slurry was stirred vigorously for 24 h at room temperature. The reaction was acidified with 5 N HCl and extracted with diethyl ether (3×10 ml). The combined ether layers were washed with $H_2O$ (3×10 ml) and brine (1×10 ml), and then dried with $Na_2SO_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with $H_2O$ (3×10 mL) and brine (1×10 mL), and then dried with $Na_2SO_4$. The resulting solution was concentrated to a light yellow oil and dried in vacuo for 48 h. This yielded 8 as a waxy, off-white solid (110 mg, 97%). $^1$H-NMR ($CDCl_3$/TMS, ppm): 0.87 (m, 12H, 4a'-, 8a'-, 12a'-, 13'-$CH_3$), 1.0-1.6 (m, 24H, 4'-, 8'-, 12'-CH, 1'-, 2'-, 3'-, 5'-, 6'-, 7'-, 9'-, 10'-, 11'-$CH_2$, 2a-$CH_3$), 1.81 (m, 2H, 3-$CH_2$), 2.12, 2.19 (2×s, 6H, 7a-, 8a-$CH_3$), 2.61 (t, J=6.6 Hz, 2H, 4-$CH_2$), 4.59 (s, 2H, $OCH_2$), 6.39 (s, 1H, aryl CH); $^{13}$C-NMR ($CDCl_3$, ppm): 11.9, 12.0 (7a-, 8a-$CH_3$), 19.6, 19.7 ($CH_3$), 20.7, 21.0 ($CH_2$), 22.6, 22.7 ($CH_3$), 23.8 (2a-$CH_3$), 24.4, 24.8 ($CH_2$), 27.9 (CH), 31.2 (3-$CH_2$), 32.7, 32.8 (CH), 37.2, 37.4, 37.5, 39.4, 40.0 ($CH_2$), 66.6 ($OCH_2$), 75.7 (2-C), 110.6, 117.7, 125.0, 126.3 (aryl C), 146.9, 148.7 (aryl C—O), 175.0 (COOH); HRMS (CI, m/z): 475.377962 (M+H$^+$, Calc. for $C_{30}H_{51}O_4$ 475.378736).

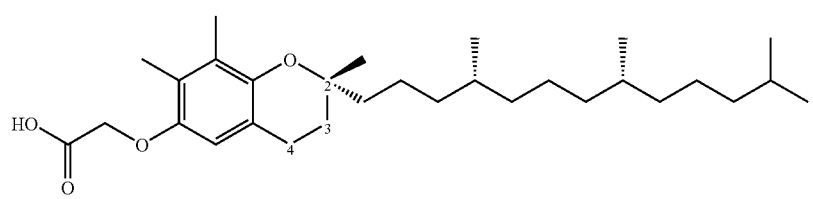

2,8-dimethyl-(2R-(4R,8R,12-trimethyltridecyl)chroman-6-yloxy)acetic acid (9)

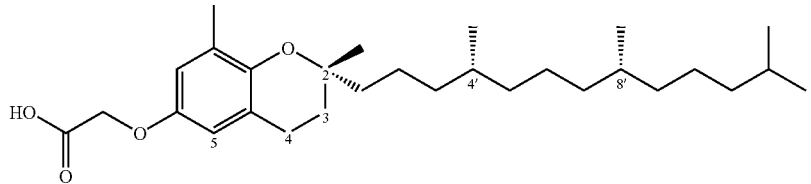

A solution of R,R,R-α-tocopherol (100 mg, 0.25 mmol) in N,N-dimethylformamide (5 mL) was treated with methyl bromoacetate (1.1 g, 7.4 mmol) and an excess of powdered NaOH (1.0 g, 25 mmol). The resulting yellow slurry was stirred vigorously for 24 h at room temperature. The reaction was acidified with 5 N HCl and extracted with diethyl ether (3×10 ml). The combined ether layers were washed with $H_2O$ (3×10 ml) and brine (1×10 ml), and then dried with $Na_2SO_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with $H_2O$ (3×10 mL) and brine (1×10 mL), and then dried with $Na_2SO_4$. The resulting solution was concentrated to a light yellow oil and dried in vacuo for 48 h. This yielded 9 as a waxy, off-white solid (111 mg, 98%). $^1$H-NMR ($CDCl_3$/TMS, ppm): 0.87 (m, 12H, 4a'-, 8a'-, 12a'-, 13'-$CH_3$), 1.0-1.6 (m, 24H, 4'-, 8'-, 12'-CH, 1'-, 2'-, 3'-, 5'-, 6'-, 7'-, 9'-, 10'-, 11'-$CH_2$, 2a-$CH_3$), 1.81 (m, 2H, 3-$CH_2$), 2.15 (s, 3H, 8a-$CH_3$), 2.71 (t, J=6.6 Hz, 2H, 4-$CH_2$), 4.59 (s, 2H, $OCH_2$), 6.48 (d, J=3.0 Hz, 1H, aryl CH), 6.61 (d, J=3.0 Hz, 1H, aryl CH); $^{13}$C-NMR ($CDCl_3$, ppm): 16.2 (8a-$CH_3$), 19.6, 19.7 ($CH_3$), 21.0 ($CH_2$), 22.6, 22.7 ($CH_3$), 24.0 (2a-$CH_3$), 24.4, 24.8 ($CH_2$), 27.9 (CH), 31.2 (3-$CH_2$), 32.7, 32.8 (CH), 37.2, 37.4, 37.5, 39.4, 40.0 ($CH_2$), 65.7 ($OCH_2$), 75.8 (2-C), 112.3, 115.6, 121.1, 127.5 (aryl C), 147.2, 149.9 (aryl C—O), 174.8 (COOH); HRMS (CI, m/z): 460.3552022 (M+H$^+$, Calc. for $C_{30}H_{51}O_4$ 460.355262).

2,5,7,8-tetramethyl-(2R-(4R,8R,12-trimethyltridecyl)chroman-6-yloxy)acetamide (10)

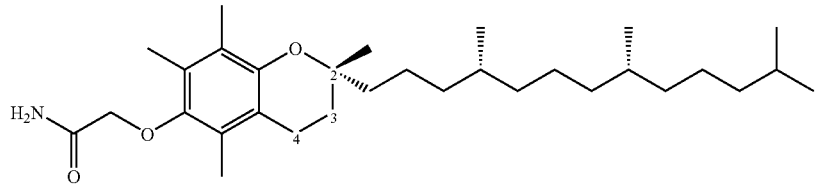

A solution of 1 (0.1 g, 0.2 mmol) in $CH_2Cl_2$ (5 mL) was treated with N-hydroxysuccinimide (26 mg, 0.23 mmol) and dicyclohexylcarbodiimide (46 mg, 0.23 mmol). After 2 min, a white precipitate formed. The resulting suspension was stirred for 2 h. The reaction stirred for an additional 6 h. The reaction mixture was cooled to −30° C. and filtered. The filtrate was concentrated and the resulting colorless oil was purified by silica gel chromatography eluting with EtOAc (35%, v/v) in hexanes. This yielded a white solid (75 mg, 76%). $^1$H-NMR ($CDCl_3$/TMS, ppm): 0.87 (m, 12H, 4a'-, 8a'-, 12a'-, 13'-$CH_3$), 1.0-1.6 (m, 24H, 4'-, 8'-, 12'-CH, 1'-, 2'-, 3'-, 5'-, 6'-, 7'-, 9'-, 10'-, 11'-$CH_2$, 2a-$CH_3$), 1.81 (m, 2H, 3-$CH_2$), 2.10, 2.12, 2.16 (3×s, 9H, 5a-, 7a-, 8a-$CH_3$), 2.59 (t, J=6.6 Hz, 2H, 4-$CH_2$), 4.19 (s, 2H, $OCH_2$), 6.36, 6.92 (2×broad, 2H, NH); $^{13}$C-NMR ($CDCl_3$, ppm): 11.7, 11.8, 121.7 (5a-, 7a-, 8a-$CH_3$), 19.6, 19.7 ($CH_3$), 20.6, 21.0 ($CH_2$), 22.6, 22.7 ($CH_3$), 23.8 (2a-$CH_3$), 24.4, 24.8 ($CH_2$), 28.0 (CH), 31.2 (3-$CH_2$), 32.7, 32.8 (CH), 37.3, 37.4, 37.5, 39.4, 40.0 ($CH_2$), 70.9 ($OCH_2$), 74.9 (2-C), 117.8, 123.3. 125.4, 127.3 (aryl C), 146.5, 148.4 (aryl C—O), 172.1 (COOH); HRMS (CI, m/z): 488.409341 (M+H$^+$, Calc. for $C_{31}H_{54}NO_3$ 488.410370).

Methyl 2,5,7,8-tetramethyl-(2R-(4R,9R,12-trimethyltridecyl)chroman-6-yloxy)acetate (11)

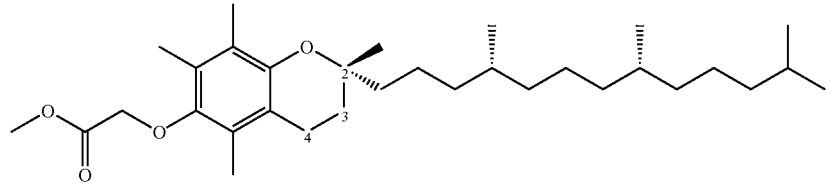

A solution of 1 (0.1 g, 0.2 mmol) in CH$_2$Cl$_2$ (5 mL) was treated with N,N-dimethylaminopyridine (26 mg, 0.23 mmol), methanol (1 ml) and dicyclohexylcarbodiimide (46 mg, 0.23 mmol) After 2 min, a white precipitate formed. The resulting suspension was stirred for 6 h. The reaction mixture was cooled to −30° C. and filtered. The filtrate was concentrated and the resulting colorless oil was purified by silica gel chromatography eluting with EtOAc (40%, v/v) in hexanes. This yielded a white solid (82 mg, 80%). $^1$H-NMR (CDCl$_3$/TMS, ppm): 0.87 (m, 12H, 4a'-, 8a'-, 12a'-, 13'-CH$_3$), 1.0-1.6 (m, 24H, 4'-, 8'-, 12'-CH, 1'-, 2'-, 3'-, 5'-, 6'-, 7'-, 9'-, 10'-, 11'-CH$_2$, 2a-CH$_3$), 1.81 (m, 2H, 3-CH$_2$), 2.10, 2.16, 2.20 (3×s, 9H, 5a-, 7a-, 8a-CH$_3$), 2.59 (t, J=6.6 Hz, 2H, 4-CH$_2$), 3.85 (s, 3H, OCH$_3$), 4.32 (s, 2H, OCH$_2$); $^{13}$C-NMR (CDCl$_3$, ppm): 11.7, 11.8, 12.7 (5a-, 7a-, 8a-CH$_3$), 19.6, 19.7 (C$_1$H$_3$), 20.6, 21.0 (CH$_2$), 22.6, 22.7 (CH$_3$), 23.8 (2a-CH$_3$), 24.4, 24.8 (CH$_2$), 28.0 (CH), 31.2 (3-CH$_2$), 32.7, 32.8 (CH), 37.3, 37.4, 37.5, 39.4, 40.0 (CH$_2$), 50.2 (OCH$_3$), 69.8 (OCH$_2$), 74.9 (2-C), 117.6, 123.0, 125.6, 127.5 (aryl C), 147.6, 148.2 (aryl C—O), 169.8 (COOH); HRMS (CI, m/z): 503.408411 (M+H$^+$, Calc. for C$_{32}$H$_{55}$O$_4$ 503.410036).

2-(N,N-(carboxymethyl)-2(2,5,7,8-tetramethyl-(2R-(4R,8R,12-trimethyl tridecyl)chroman-6-yloxy)acetic acid (12)

$^1$H-NMR (CDCl$_3$/TMS, ppm): 0.87 (m, 12H, 4a'-, 8a'-, 12a'-, 13'-CH$_3$), 1.0-1.6 (m, 30H, 4'-, 8'-, 12'-CH, 1'-, 2'-, 3'-, 5'-, 6'-, 7'-, 9'-, 10'-, 11'-CH$_2$, 2a-CH$_3$), 1.78 (m, 2H, 3-CH$_2$), 2.08, 2.13, 2.17 (3×s, 9H, 5a-, 7a-, 8a-CH$_3$), 2.58 (t, J=6.8 Hz, 2H, 4-CH$_2$), 4.19, 4.22 (q, J=7.4 Hz, 4H, OCH$_2$), 4.30, 4.33, 4.42 (3×s, 6H, 2×NCH$_2$, OCH$_2$); $^{13}$C-NMR (CDCl$_3$, ppm): 11.7, 11.8, 12.7 (5a-, 7a-, 8a-CH$_3$), 14.0 (CH$_3$), 19.6, 19.7 (CH$_3$), 20.6, 21.0 (CH$_2$), 22.6, 22.7 (CH$_3$), 23.8 (2a-CH$_3$), 24.4, 24.8 (CH$_2$), 28.0 (CH), 31.2 (3-CH$_2$), 32.7, 32.8 (CH), 37.3, 37.4, 37.5, 39.4, 40.0 (CH$_2$), 48.1, 49.4 (NCH$_2$), 61.2, 61.5 OCH$_2$), 71.8 (OCH$_2$), 74.8 (2-C), 117.5, 122.9, 125.6, 127.4 (aryl C), 148.0, 148.1 (aryl C—O), 168.8, 169.0 (CO); MS (CI, m/z): 660 (M+H$^+$, Calc. for C$_{39}$H$_{65}$NO$_7$ 659.47610).

A solution of the diester intermediate (0.15 g, 0.23 mmol) in ethanol (4 ml) was treated with 1 N NaOH (1 ml). The resulting cloudy mixture was stirred at 70° C. for 15 h. The reaction mixture was acidified with 1 N HCl and the ethanol was removed in vacuo. The resulting aqueous solution was extracted with CHCl$_3$ (5×20 ml) and the combined organic layers dried with Na$_2$SO$_4$. This yielded 12 (0.13 g, 52%) as a white solid. $^1$H-NMR (CDCl$_3$/TMS, ppm): 0.87 (m, 12H, 4a'-, 8a'-, 12a'-, 13'-CH$_3$), 1.0-1.6 (m, 24H, 4'-, 8'-, 12'-CH, 1'-, 2'-, 3'-, 5'-, 6'-, 7'-, 9'-, 10'-, 11'-CH$_2$, 2a-CH$_3$), 1.70 (m, 2H, 3-CH$_2$), 2.01, 2.05, 2.08 (3×s, 9H, 5a-, 7a-, 8a-CH$_3$), 2.47 (m, 2H, 4-CH$_2$), 4.18 (m, 4H, 2×NCH$_2$), 4.31 (m, 2H, OCH$_2$);

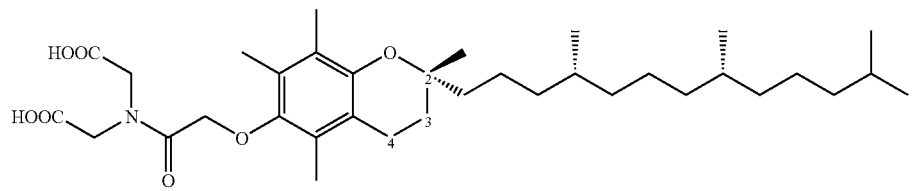

A solution of 1 (0.2 g, 0.4 mmol) in CH$_2$Cl$_2$ (5 mL) was treated with diethyl iminodiacetate (77 mg, 0.4 mmol) and O-7-azabenzotriazol-1-yl-N,N,N',N'-tetramethyluronium hexafluoro phosphate (HATU) (46 mg, 0.23 mmol). After 12 h, the reaction mixture was concentrated to a paste and then purified by silica gel chromatography eluting with EtOAc (30%, v/v) in hexanes. This yielded the desired diester intermediate as colorless oil (150 mg, 55%).

$^{13}$C-NMR (CDCl$_3$, ppm): 11.5, 11.6, 12.4 (5a-, 7a-, 8a-CH$_3$), 19.4, 19.5 (CH$_3$), 20.6, 21.0 (CH$_2$), 22.6, 22.7 (CH$_3$), 23.8 (2a-CH$_3$), 24.4, 24.8 (CH$_2$), 28.0 (CH), 31.2 (3-CH$_2$), 32.4, 32.5 (CH), 37.0, 37.2, 37.5, 39.1, 40.0 (CH$_2$), 48.1, 49.4 (NCH$_2$), 71.1 (OCH$_2$), 74.8 (2-C), 117.5, 122.9, 125.4, 127.2 (aryl C), 147.8, 148.1 (aryl C—O), 168.8, 169.0 (CO); HRMS (CI, m/z): 604.420882 (M+H$^+$, Calc. for C$_{35}$H$_{58}$NO$_7$ 604.421329).

2-(2,5,7,8-tetramethyl-(2R-(4R,8R,12-trimethyltride-cyl)chroman-6-yloxy))ethan-1-ol (13)

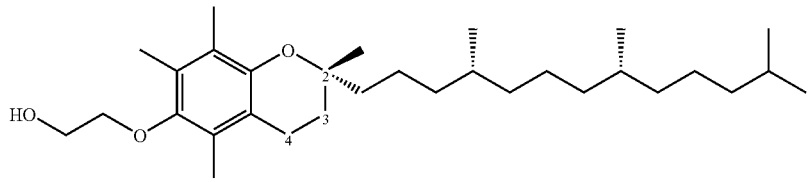

A solution of R,R,R-α-tocopherol (0.5 g, 1.16 mmol) in N,N-dimethylformamide (20 mL) was treated with iodoethanol (1.7 g, 10 mmol) and an excess of powdered NaOH (2.5 g, 63 mmol). The resulting yellow slurry was stirred vigorously for 24 h at room temperature. The reaction was acidified with 5 N HCl and extracted with diethyl ether (3×30 ml). The combined ether layers were washed with $H_2O$ (3×30 ml) and brine (1×30 ml), and then dried with $Na_2SO_4$. The ether solution was concentrated to a yellow oil that was purified by silica gel chromatography eluting with 30% (v/v) EtOAc and 2% acetic acid in hexanes. The resulting yellow liquid was dissolved in diethyl ether (30 ml), washed with $H_2O$ (3×20 mL) and brine (1×20 mL), and then dried with $Na_2SO_4$. The resulting solution was concentrated to a light yellow oil and dried in vacuo for 48 h. This yielded 13 as yellow oil (0.40 g, 73%). $^1$H-NMR (CDCl$_3$/TMS, ppm): 0.87 (m, 12H, 4a'-, 8a'-, 12a'-, 13'-CH$_3$), 1.0-1.6 (m, 24H, 4'-, 8'-, 12'-CH, 1'-, 2'-, 3'-, 5'-, 6'-, 7'-, 9'-, 10'-, 11'-CH$_2$, 2a-CH$_3$), 1.81 (m, 2H, 3-CH$_2$), 2.07, 2.14, 2.16 (3×s, 9H, 5a-, 7a-, 8a-CH$_3$), 2.59 (t, J=6.6 Hz, 2H, 4-CH$_2$), 3.79 (m, 2H, OCH$_2$), 3.94 (m, 2H, OCH$_2$); $^{13}$C-NMR (CDCl$_3$, ppm): 11.7, 11.8, 12.7 (5a-, 7a-, 8a-CH$_3$), 19.6, 19.7 (CH$_3$), 20.6, 21.0 (CH$_2$), 22.6, 22.7 (CH$_3$), 23.8 (2a-CH$_3$), 24.4, 24.8 (CH$_2$), 28.0 (CH), 31.2 (3-CH$_2$), 32.7, 32.8 (CH), 37.3, 37.4, 37.5, 39.4, 40.0 (CH$_2$), 63.1, 69.2 (OCH$_2$), 75.0 (2-C), 117.8, 123.4, 126.4, 128.3 (aryl C), 149.2, 149.5 (aryl C—O); MS (CI, m/z): 475 (M+H$^+$, Calc. for C$_{31}$H$_{54}$O$_3$ 474.40729).

2-(2,5,7,9-pentamethylchroman-6-yloxy)acetic acid (14)

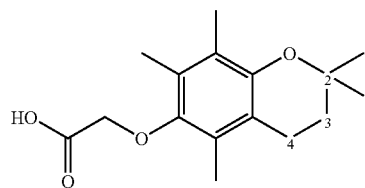

A solution of 2,2,5,7,8-pentamethyl-6-chromanol (0.3 g, 1.36 mmol) in N,N-dimethylformamide (20 mL) was treated with methyl bromoacetate (0.8 g, 5.3 mmol) and an excess of powdered NaOH (0.7 g, 18 mmol). The resulting yellow slurry was stirred vigorously for 24 h at room temperature. The reaction was acidified with 5 N HCl and extracted with diethyl ether (3×30 ml). The combined ether layers were washed with $H_2O$ (3×30 ml) and brine (1 ×30 ml), and then dried with $Na_2SO_4$. The ether solution was concentrated to a yellow oil that was purified by silica gel chromatography eluting with 30% (v/v) EtOAc and 2% acetic acid in hexanes. The resulting yellow liquid was dissolved in diethyl ether (30 ml), washed with $H_2O$ (3×20 mL) and brine (1×20 mL), and then dried with $Na_2SO_4$. The resulting solution was concentrated to a light yellow oil and dried in vacuo for 48 h. This yielded 14 as a white solid (0.31 g, 82%). $^1$H-NMR (CDCl$_3$/TMS, ppm): 1.31 (s, 6H, CH$_3$), 1.81 (t, J=7.8 Hz, 3-CH$_2$), 2.10, 2.16, 2.19 (3×s, 9H, 5a-, 7a-, 8a-CH$_3$), 2.61 (t, J=7.8 Hz, 2H, 4-CH$_2$), 4.39 (s, 2H, OCH$_2$); $^{13}$C-NMR (CDCl$_3$, ppm): 11.7, 11.8, 12.7 (5a-, 7a-, 8a-CH$_3$), 20.9, 26.8, 32.7 (alkyl), 69.1, (OCH$_2$), 72.9 (2-C), 117.5, 123.2, 125.5, 127.3 (aryl), 147.0, 148.6 (O-aryl), 173.8 (COOH); HRMS (CI, m/z): 279.159238 (M+H$^+$, Calc. for C$_{16}$H$_{23}$O$_4$ 279.159634).

2,5,7,8-tetramethyl-(2RS-(4RS,8R,12-trimethyltride-cyl)chroman-6-yloxy)acetic acid (15)

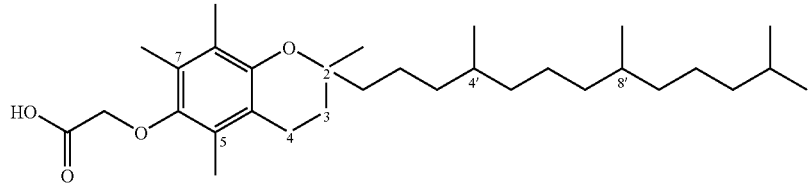

A solution of all racemic-α-tocopherol (0.5 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 NHCl and extracted with diethyl ether (3×30 ml). The combined ether layers were washed with H₂O (3×30 ml) and brine (1×30 ml), and then dried with Na₂SO₄. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with H₂O (3×20 mL) and brine (1×20 mL), and then dried with Na₂SO₄. The resulting solution was concentrated to a light yellow oil and dried in vacuo for 48 h. This yielded 15 as a waxy, off-white solid (80%). $^1$H-NMR (CDCl₃/TMS, ppm): 0.88 (m, 12H, 4a'-, 8a'-, 12a'-, 13'-CH₃), 1.0-1.6 (m, 24H, 4'-, 8'-, 12'-CH, 1'-, 2'-, 3'-, 5'-, 6'-, 7'-, 9'-, 10'-, 11'-CH₂, 2a-CH₃), 1.84 (m, 2H, 3-CH₂), 2.07, 2.14, 2.16 (3×s, 9H, 5a-, 7a-, 8a-CH₃), 2.61 (t, J=6.6 Hz, 2H, 4-CH₂), 4.34 (s, 2H, OCH₂); $^{13}$C-NMR (CDCl₃, ppm): 11.5, 11.7, 12.6 (5a-, 7a-, 8a-CH₃), 19.6, 19.7 (CH₃), 20.6, 21.3 (CH₂), 22.6, 22.8 (CH₃), 23.8 (2a-CH₃), 24.5, 24.9 (CH₂), 29.0 (CH), 31.6 (3-CH₂), 32.6, 32.8 (CH), 37.5, 37.8, 37.9, 39.5, 41.0 (CH₂), 69.3 (OCH₂), 75.1 (2-C), 117.9, 123.3, 125.5, 127.3 (aryl C), 147.0, 148.0 (aryl C—O), 173.9 (COOH); HRMS (CI, m/z): 489.394375 (M+H⁺, Calc. for C₃₁H₅₃O₄ 489.394383).

2,5,7,8-tetramethyl-(2R-(carboxy)chroman-6-yloxy)) acetic acid (16)

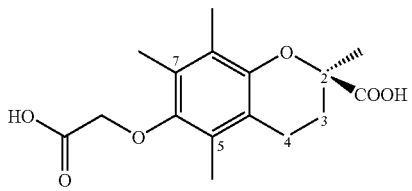

A solution of (−)-(R)-6-hydroxy-2,5,7,8-tetramethylchroman-2-carboxylic acid (0.34 g, 1.36 mmol) in N,N-dimethylformamide (20 mL) was treated with methyl bromoacetate (0.8 g, 5.3 mmol) and an excess of powdered NaOH (0.7 g, 18 mmol). The resulting yellow slurry was stirred vigorously for 24 h at room temperature. The reaction was acidified with 5 N HCl and extracted with diethyl ether (3×30 ml). The combined ether layers were washed with H₂O (3×30 ml) and brine (1×30 ml), and then dried with Na₂SO₄. The ether solution was concentrated to a yellow oil that was purified by silica gel chromatography eluting with 30% (v/v) EtOAc and 2% acetic acid in hexanes. The resulting yellow liquid was dissolved in diethyl ether (30 ml), washed with H₂O (3×20 mL) and brine (1×20 mL), and then dried with Na₂SO₄. The resulting solution was concentrated to light yellow oil and dried in vacuo for 48 h. This yielded 16 as a white solid (0.33 g, 80%). $^1$H-NMR (CDCl₃/TMS, ppm): 1.52 (s, 3H, 2a-CH₃), 2.10 (m, 2H, 3-CH₂), 2.12, 2.16, 2.19 (3×s, 9H, 5a-, 7a-, 8a-CH₃), 2.56 (t, J=6.5 Hz, 2H, 4-CH₂), 4.36 (s, 2H, OCH₂).

2,5,7,8-tetramethyl-2R-(2RS,6RS,10-trimethylundecyl)chroman-66 yloxy)acetic acid (17)

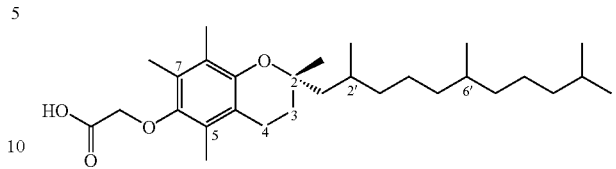

A solution of 10 g (40 mmol) of (−)-(S)-6-hydroxy-2,5,7, 8-tetramethylchroman-2-carboxylic acid and 0.5 g of p-toluenesulfonic acid monohydrate in 200 ml of methanol was stirred and refluxed for 4 hr. After cooling, the solution was diluted with water and extracted with diethyl ether. The combined ether layers were washed with saturated aqueous sodium bicarbonate solution, H₂O, and brine (1×30 ml), and then dried with Na₂SO₄. The resulting solution was concentrated and dried in vacuo for 48 h. This yielded 10 g (95%) of methyl(−)-(S)-6-hydroxy-2,5,7,8-tetramethylchroman-2-carboxylate as a colorless solid which was used without further purification. $^1$H-NMR (CDCl₃/TMS, ppm): 1.52 (s, 3H, 2a-CH₃), 2.10 (m, 2H, 3-CH₂), 2.12, 2.16, 2.19 (3×s, 9H, 5a-, 7a-, 8a-CH₃), 2.56 (t, J=6.5 Hz, 2H, 4-CH₂), 3.55 (s, 3H, OCH₃); MS (CI, m/z): 264.422 M+H⁺, Calc. for C₁₅H₂₀O₄ 265.3224.

To a solution of 2 g (7.58 mmol) of this ester in 7.5 ml of N, N-dimethylformamide (DMF) was added 2.6 g (18.8 mmol) of anhydrous granular potassium carbonate followed by 2.3 ml (20 mmol) of benzylchloride. The resulting slurry was stirred at RT for 41 h then poured into 50 ml of water and worked up with ether in the usual way. The product was freed of excess benzyl chloride at 50° under high vacuum. There was obtained 2.69 g (100%) of pure (TLC) (−)-(S)-6-benzyloxy-2,5,7,8-tetramethyl-chroman-2-carboxylic acid methyl ester as a yellow solid, m.p. 102-106°. The analytical specimen of this compound was prepared as a colorless solid m.p. 108-109° (from ether/methanol). $^1$H-NMR (CDCl₃/TMS, ppm): 1.54 (s, 3H, 2a-CH₃), 2.01 (m, 2H, 3-CH₂), 2.14, 2.17, 2.19 (3×s, 9H, 5a-, 7a-, 8a-CH₃), 2.51 (t, J=6.7 Hz, 2H, 4-CH₂), 3.64 (s, 3H, OCH₃), 5.12 (s, 2H, 6-OCH₂), 7.15 (m, 5H, ArH); MS (CI, m/z): 355.232 M+H⁺, Calc. for C₂₂H₂₅O₄ 354.448.

A solution of 3.54 g (10 mmol) of the above ether ester, in 20 ml of toluene and 10 ml of CH₂Cl₂ was stirred with cooling from dry ice/acetone bath while 12 ml (18 mmol) of 25% disobutylaluminum hydride in toluene (Texas Alkyls) was added dropwise, over 10 min. After stirring at ca. −70° for 30 min, the reaction mixture was cautiously decomposed (−70°) with 10 ml of MeOH. Following the addition of 50 ml of water and 50 ml of 1N aqueous H₂SO₄ solution, the mixture was warmed to RT, and worked up with ether in the usual way giving 3.2 g (100%) of crude aldehyde [(+) S-6-Benzyloxy-2,5,7,8-tetramethylchroman-2-carbaldhyde] as a viscous oil which was purified by silica gel chromatography eluting with 19% (v/v) EtOAc in hexane.

$^1$H-NMR (CDCl₃/TMS, ppm): 1.53 (s, 3H, 2a-CH₃), 2.11 (m, 2H, 3-CH₂), 2.24, 2.27, 2.29 (3×s, 9H, 5a-, 7a-, 8a-CH₃), 2.481 (t, J=6.7 Hz, 2H, 4-CH₂), 5.19 (s, 2H, 6-OCH₂), 7.20 (m, 5H, ArH), 9.6 (s, 1H', CHO); MS (CI, m/z): 325.332 M+H⁺, Calc. for C₂₁H₂₄O₃ 324.422.

A solution of 9.6 g of pseudoionone was dissolved in 100 ml of 95% ethanol; after 0.68 g of sodium borohydride in ethanol had been added at room temperature, the mixture was stirred for 2 hr and then left standing overnight. The mixture was added to a solution of 2 g of sodium hydroxide in 500 ml of water. The mixture was extracted with ether, and the ether extract was washed with water, dried, and concentrated. The distillation of the residual oil in vacuo gave a colorless oil (pseudoionol); bp 112-120° C./5 mmHG. 7.7 g (80%).

To a solution of 2.97 g of pseudoionol in 10 ml of acetonitrile, there were added, under stirring and while the temperature was kept below 30° C., 4.53 g of triphenylphospine hydrochloride which had been obtained by passing dry hydrogen chloride into a solution of triphenylphosphine in dry ether. After the mixture had been left standing overnight at room temperature, the acetonitrile was removed under reduced pressure below 50° C. To the residue there were added 4.47 gm of (+) S-6-Benzyloxy-2,5,7,8-tetramethyl-chroman-2-carbaldehyde in 15 ml of dimethylformamide, and the mixture was stirred. When a clear solution was obtained, sodium methoxide prepared from 0.352 g of sodium and 7 ml of anhydrous methanol was stirred in, drop by drop below 15° C. The reaction mixture was turned red by the ylid formed. After the addition was complete, stirring was continued for 30 min at 10° C.; then the mixture was gradually heated to 80° C., when the red color disappeared. The product was poured into 200 ml of 50% aqueous methanol, dried, and concentrated in vacuo. The residual oil was dissolved in 20 ml of ether, and an ethereal solution of mercuric chloride was added until no more precipitate formed. When the precipitate was filtered and the filtrate was washed with water, dried and concentrated, to give 4.7 g of yellow oil were obtained. The crude mixture of cis and trans alkene (MS (CI, m/z): 485.22, M+H+, Calc. for $C_{34}H_{44}O_2$ 484.7255) was dissolved in 30 ml of ethyl acetate and 0.80 g of 5% palladium o n carbon was added, and the mixture was shaken under 40 psi of $H_2$ for 30 hrs and then filtered through Celilte and rinsed well with ethyl acetate. The filtrate was concentrated and purified by silica gel chromatography eluting with EtOAc in hexane (1:9) to give 2,5,7,8-tetramethyl-(2R-(2RS,6RS, 10-trimethylundecyl))-6-chromanol (60% yield) $^1$H-NMR (CDCl$_3$/TMS, ppm): 0.97 (m, 12H, 2a'-, 6a'-, 10a'-, 11'-CH$_3$), 1.1-1.7 (m, 20H, 2'-, 6'-, 10'-CH, 1'-, 3'-4'-, 5'-, 7'-, 8'-, 9'-CH$_2$, 2a-CH$_3$), 1.88 (m, 2H, 3-CH$_2$), 2.17, 2.19, 2.20 (3×s, 9H, 5a-, 7a-, 8a-CH$_3$), 2.63 (t, J=6.7 Hz, 2H, 4-CH$_2$); (MS (CI, m/z): 403.27, M+H+, Calc. for $C_{27}H_{46}O_2$ 402.6632.

A solution of 2,5,7,8-tetramethyl-(2R-(2RS,6RS,10-trimethylundecyl))-6-chromanol (0.466 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with $H_2O$ (3×30 ml) and brine (1×30 ml), and then dried with $Na_2SO_4$. The ether solution was concentrated to a yellow oil that was purified by silica gel chromatography eluting with 19% (v/v) EtOAc and 2% acetic acid in hexanes. This yielded compound 17 in 76% yield. $^1$H-NMR (CDCl$_3$/TMS, ppm): 0.97 (m, 12H, 2a'-, 6a'-, 10a'-, 11'-CH$_3$), 1.2-1.7 (m, 20H, 2'-, 6'-,10'-CH, 1'-, 3'-, 4'-, 5'-, 7'-, 8'-, 9'-CH$_2$, 2a-CH$_3$), 1.92 (m, 2H, 3-CH$_2$), 2.18, 2.20, 2.23 (3×s, 9H, 5a-, 7a-, 8a-CH$_3$), 2.68 (t, J=6.8 Hz, 2H, 4-CH$_2$), 4.48 (s, 2H, OCH$_2$); MS (CI, m/z): 461.44, M+H+, Calc. for $C_{29}H_{48}O_4$ 460.700.

2,5,7,8-tetramethyl-2R-(2,6,10-trimethyl-1,3,5,9 E:Z decatetraen) chroman-6-yloxy)acetic acid (18)

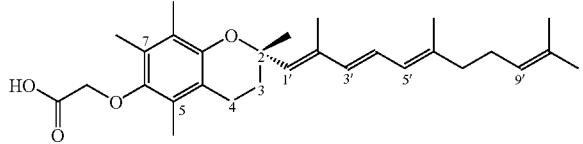

To a solution of methyl(−)-(S)-6-hydroxy-2,5,7,8-tetramethylchroman-2-carboxylate (20 gms 0.075 mole) in 50 ml of dry DMF, imidazole (13 gm, 0.1911 mole), and tert-butyldimethyl-silyl chloride (14 gm, 0.0933 mole) were added. The mixture was stirred at 23° C. for 24 hr and then treated with ether and poured into 1N HCl. The organic extracts were dried (brine, $Na_2SO_4$) and concentrated in vacuo. The crude product was purified by flash chromatography (9:1 hexane: ethyl acetate) to yield 6-[dimethyl (1,1-dimethylethyl)silyl]-2,5,7,8-tetramethyl-chroman-2-carboxylate (TBS protected methyl ester). $^1$H-NMR (CDCl$_3$/TMS, ppm): 0.12 (s, 6H). 1.102 (s, 9H), 1.18 (s, 3H), 1.48 (s, 3H), 1.645 (s, 3H), 2.07 (s, 3H), 2.2 (t, J=6.5 hz 2H), 2.48-2.7 (m, 2H) and 3.72 (s, 3H, OCH$_3$) (MS (CI, m/z): 379.32, M+H+, Calc. for $C_{21}H_{34}O_4$ 378.586.

A solution of 3.78 g (10 mmol) of the above ether ester, in 20 ml of toluene and 10 ml of $CH_2Cl_2$ was stirred with cooling from dry ice/acetone bath while 12 ml (18 mmol) of 25% disobutylaluminum hydride in toluene (Texas Alkyls) was added dropwise, over 10 min. After stirring at ca. −70° for 30 min, the reaction mixture was cautiously decomposed (−70°) with 10 ml of MeOH. Following the addition of 50 ml of water and 50 ml of 1N aqueous $H_2SO_4$ solution, the mixture was warmed to RT, and worked up with ether in the usual way giving 3.2 g (90%) of crude aldehyde [(+)S-6-[dimethyl(1,1-dimethylethyl)silyl]-2,5,7,8-tetramethyl-chroman-2-carbaldhyde] as a viscous oil which was purified by silica gel chromatography eluting with 19% (v/v) EtOAc in hexane. Concentration of the solution followed by drying under vacuo for 48 h yielded TBDS aldehyde (78%) as a solid of mp 66-68° C. $^1$H-NMR (CDCl$_3$/TMS, ppm): 0.12 (s, 6H). 1.1 (s, 9H), 1.38 (s, 3H), 1.64 (s, 3H), 2.12 (s, 3H), 2.16 (s, 3H), 2.3-2.2 (m, 2H), 2.53 (m, 2H) and 9.82 (d, J=1.4 Hz, 1H); MS (CI, m/z): 349.40 M+H+, Calc. for $C_{20}H_{32}SiO_3$ 348.560.

To a solution of 2.97 g of psedoionol in 10 ml of acetonitrile, there were added, under stirring and while the temperature was kept below 30° C., 4.53 g of triphenylphosphine hydrochloride which had been obtained by passing dry hydrogen chloride into a solution of triphenylphosphine in dry ether. After the mixture had then been left standing overnight at room temperature, the acetonitrile was removed under reduced pressure below 50° C. To the residue there were added 4.80 gm of [(+)S-6-[dimethyl(1,1-dimethylethyl)silyl]-2,5,7,8-tetramethylchroman-2-carbaldhyde] in 15 ml of dimethylformamide, and the mixture was stirred. When a clear solution was obtained, sodium methoxide prepared from 0.352 g of sodium and 7 ml of anhydrous methanol was stirred in, drop by drop below 15° C. The reaction mixture was turned red by the ylid formed. After the addition was complete, stirring was continued for 30 min at 10° C.; then the mixture was gradually heated to 80° C., when the red color disappeared. The product was poured into 200 ml of 50% aqueous methanol, dried, and concentrated in vacuo. The residual oil was dissolved in 20 ml of ether, and an ethereal solution of mercuric chloride was added until no more precipitate formed. When the precipitate was filtered and the filtrate was washed with water, dried and concentrated, to give 4.7 g of yellow oil were obtained. The crude silyl ether mixture of cis and trans alkene was dissolved in THF and tetra-n-butylammonium fluoride (0.031 mole) was added. After being stirred at 23° C. for 40 minutes, the mixture was poured into water and extracted into ether. The ether extract was dried concentrated and purified by silica gel chromatography eluting with EtOAc in hexane (1:9) to give 2,5,7,8-tetramethyl-2R-(2,6,10-trimethyl-1,3,5,9 EZ decatetraen)-6-chromanol (68% yield). $^1$H-NMR (CDCl$_3$/TMS, ppm): 1.28 (s, 3H, 2aCH$_3$), 1.65 (s, 3H), 1.70 (s, 6H) 1.72 (s, 3H), 1.9 (m, 6H), 2.18 (s, 3H), 2.35 (S, 6H), 2.53 (t, J=6.6 Hz, 2H, 4-CH$_2$), 5.13-5.27 (m, 3H) and 6.44 (m, 2H); MS (CI, m/z): 395.17 M+H$^+$, Calc. for C$_{27}$H$_{38}$O$_2$ 394.60.

A solution of 2,5,7,8-tetramethyl-2R-(2,6,10-trimethyl-1, 3,5,9 E:Z decatetraen)-6-chromanol (0.457 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 NHCl and extracted with diethyl ether (3×30 ml). The combined ether layers were washed with H$_2$O (3×30 ml) and brine (1×30 ml), and then dried with Na$_2$SO$_4$. The ether solution was concentrated to a yellow oil that was purified by silica gel chromatography eluting with 19% (v/v) EtOAc and 2% acetic acid in hexanes. The resulting liquid was dissolved in diethyl ether (30 ml), washed with H$_2$O (3×20 mL) and brine (1×20 mL), and then dried with Na$_2$SO$_4$. The resulting solution was concentrated and dried in vacuo for 48 h. This yielded compound 18 in 67% yield. $^1$H-NMR (CDCl$_3$/TMS, ppm):1.24 (s, 3H, 2aCH$_3$), 1.63 (s, 3H), 1.72 (s, 6H) 1.74 (s, 3H), 1.92 (m, 6H), 2.18 (s, 3H), 2.29 (S, 6H), 2.43 (t, J=6.6 Hz, 2H, 4-CH$_2$), 4.68 (s, 2H, OCH$_2$), 5.10-5.27 (m, 3H) and 6.34 (m, 2H) MS (CI, m/z): 452.24 M–H$^+$, Calc. for C$_{27}$H$_{38}$O$_2$ 452.63.

3-(2,5,7,8-tetramethyl-(2R-(4R,8,12-trimethyltride-cyl)chroman-6-yloxy)propyl-1-ammonium chloride (19)

A solution of 3-bromopropylamine hydrobromide (1.0 g, 4.6 mmol) in a 2:1 dioxane/H$_2$O (45 mL) was cooled to 0° C. and treated with K$_2$CO$_3$ (6.22 g, 45 mmol) and di-tert-butyl dicarbonate (1.5 g, 6.9 mmol). The reaction was stirred for 15 h while warming to room temperature. The dioxane was removed in vacuo and the remaining aqueous mixture was acidified with 5 N HCl and extracted with ethyl acetate (5×25 mL). The combined organic layers were dried with MgSO$_4$ and yielded 3-bromo-N-(tert-butoxycarbonyl)propylamine as a colorless oil (0.93 g, 93%). $^1$H-NMR (CDCl$_3$/TMS, ppm): 1.41 (s 9H, CH$_3$), 2.02 (quintet, J=6.4 Hz, 2H, CH$_2$), 3.23 (m, 2H, NCH$_2$), 3.41 (t, J=6.6 Hz, CH$_2$Br), 4.8 (broad, 1H, NH); $^{13}$C-NMR (CDCl$_3$, ppm): 28.3 (CH$_3$), 30.7, 32.6, 38.9 (CH$_2$), 79.3 (quaternary C), 155.9 (CO); MS (CI, m/z): 239, 241 (M+H$^+$ Calc. for C$_8$H$_{16}$BrNO$_2$ 237.03644).

A solution of R,R,R-α-tocopherol (0.5 g, 1.16 mmol) in N,N-dimethylformamide (15 mL) was treated with 3-bromo-N-(tert-butoxycarbonyl)propylamine (0.9 g, 3.8 mmol) and an excess of powdered NaOH (0.32 g, 8 mmol). The resulting yellow slurry was stirred vigorously for 24 h at room temperature. The reaction was acidified with 5 NHCl and extracted with diethyl ether (3×30 ml). The combined ether layers were washed with H$_2$O (3×30 ml) and brine (1×30 ml), and then dried with Na$_2$SO$_4$. The ether solution was concentrated to a yellow oil that was purified by silica gel chromatography eluting with EtOAc (10% v/v) in hexanes. This yielded desired ether as a colorless oil (0.45 g, 66%). $^1$H-NMR (CDCl$_3$/TMS, ppm): 0.87 (m, 12H, 4a'-, 8a'-, 12a'-, 13'-CH$_3$), 1.0-1.6 (m, 33H, 4'-, 8'-, 12'-CH, 1'-, 2'-, 3'-, 5'-, 6'-, 7'-, 9'-, 10'-, 11'-CH$_2$, 2a-CH$_3$), 1.81 (m, 2H, 3-CH$_2$), 1.99 (quintet, J=6.2 Hz, 2H, CH$_2$), 2.07, 2.14, 2.16 (3×s, 9H, 5a-, 7a-, 8a-CH$_3$), 2.59 (t, J=6.6 Hz, 2H, 4-CH$_2$), 3.43 (m, 2H. NCH$_2$), 3.73 (t, J=5.7 Hz, 2H, OCH$_2$), 4.34 (s, 2H, OCH$_2$); $^{13}$C-NMR (CDCl$_3$, ppm): 11.7, 12.0, 12.9 (5a-, 7a-, 8a-CH$_3$), 19.6, 19.7 (CH$_3$), 20.6, 21.0 (CH$_2$), 22.6, 22.7 (CH$_3$), 23.7 (2a-CH$_3$), 24.4, 24.8 (CH$_2$), 27.9 (CH), 31.2 (3-CH$_2$), 32.7, 32.8 (CH), 37.2, 37.4, 37.5, 39.3, 40.1 (CH$_2$), 70.2 (OCH$_2$), 74.8 (2-C), 117.5, 122.9, 125.5, 127.5 (aryl C), 147.5, 148.0 (aryl C—O), 156.0 (CO); MS (CI, m/z): 589 M+H$^+$, Calc. for C$_{37}$H$_{65}$NO$_4$ 587.49136.

The above N-protected ether (0.1 g, 0.17 mmol) was dissolved 4 N HCl in dioxane (1 mL, 4 mmol) and stirred for 4 h. The dioxane was removed by blowing a stream of argon over the reaction mixture. The resulting material was dried in vacuo for 8 h yielding 19 as a white solid (82 mg, 99%). $^1$H-NMR (CDCl$_3$/TMS, ppm): 0.87 (m, 12H, 4a'-, 8a'-, 12a'-, 13'-CH$_3$), 1.0-1.6 (m, 33H, 4'-, 8'-, 12'-CH, 1'-, 2'-, 3'-, 5'-, 6'-, 7'-, 9'-, 10'-, 11'-CH$_2$, 2a-CH$_3$), 1.81 (m, 2H, 3-CH$_2$), 1.99 (quintet, J=6.2 Hz, 2H, CH$_2$), 2.07, 2.11, 2.15 (3×s, 9H, 5a-, 7a-, 8a-CH$_3$), 2.29 (m, 2H, CH$_2$), 2.59 (t, J=6.6 Hz, 2H, 4-CH$_2$), 3.43 (m, 2H. NCH$_2$), 3.79 (m, 2H, OCH$_2$) $^{13}$C-NMR (CDCl$_3$, ppm): 11.8, 11.9, 12.7 (5a-, 7a-, 8a-CH$_3$), 19.6, 19.7 (CH$_3$), 20.6, 21.0 (CH$_2$), 22.6, 22.7 (CH$_3$), 23.9 (2a-CH$_3$), 24.4, 24.8 (CH$_2$), 28.0 (CH), 28.4 (CH$_3$), 31.2 (3-CH$_2$), 32.7, 32.8 (CH), 37.3, 37.4, 37.5, 39.4, 40.0 (CH$_2$), 74.8 (OCH$_2$), 75.0 (2-C), 117.5, 122.9, 126.0, 127.3 (aryl C), 147.8, 148.0 (aryl C—O); HRMS (CI, m/z): 487.438887 (M+H$^+$, Calc. for C$_{32}$H$_{57}$NO$_2$ 487.438935).

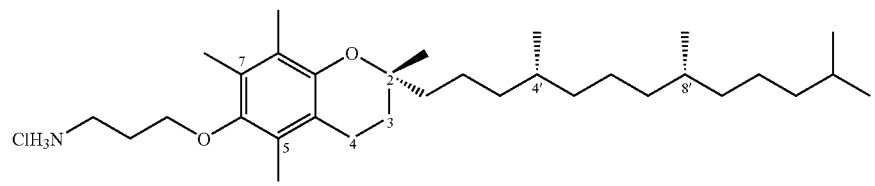

2,5,7,8-tetramethyl-(2R-(4R,8R,12-trimethyltridecyl) chroman-3-ene-6-yloxy)acetic acid (20)

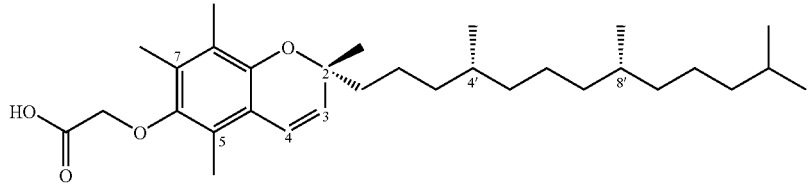

A solution of R,R,R,-α-tocopherol acetate (2 g, 4.2 mmol) in anhydrous toluene (150 mL) was heated to reflux and then treated with 2,3-dichloro-5,6-dicyano-1,4-benzoquinone (0.96 g, 4.2 mmol) in 4 portions at 1 h intervals. The reaction was refluxed for 24 h. During this time the reaction mixture became a dark red color and then it precipitated a light colored solid. The reaction was cooled to room temperature, filtered, and the filtrate was concentrated. The resulting dark colored oil was purified by silica gel chromatography eluting with ethyl acetate (10%, v/v) in hexanes. This yielded the desired chromene acetate as a colorless oil (1.74 g, 88%). $^1$H-NMR (CDCl$_3$/TMS, ppm): 0.87 (m, 12H, 4a'-, 8a'-, 12a'-, 13'-CH$_3$), 1.0-1.6 (m, 24H, 4'-, 8'-, 12'-CH, 1'-, 2'-, 3'-, 5'-, 6'-, 7'-, 9'-, 10'-, 11'-CH$_2$, 2a-CH$_3$), 2.07, 2.13, 2.18 (3×s, 9H, 5a-, 7a-, 8a-CH$_3$), 2.35 (s, 3H, CH$_3$CO—), 5.61, 6.52 (2×d, J =10.0 Hz, 2H, CH); $^{13}$C-NMR (CDCl$_3$, ppm): 11.5, 11.6, 13.1 (5a-, 7a-, 8a-CH$_3$), 14.1 (CH$_3$), 19.6, 19.7 (CH$_3$), 20.4, 21.4 (CH$_2$), 22.6, 22.7 (CH$_3$), 24.4, 24.8 (CH$_2$), 25.8 (2a-CH$_3$), 27.9 (CH), 30.8 (3-CH$_2$), 32.7, 32.8 (CH), 37.2, 37.4, 39.4, 41.0 (CH$_2$), 60.3 (2-C), 117.6, 119.7, 122.3, 122.6, 128.9, 129.6 (aryl and vinyl C), 141.2, 148.4 (aryl C—O), 169.4 (CO); HRMS (CI, m/z): 471.375799 M+H$^+$, Calc. for C$_{31}$H$_{50}$O$_3$ 470.375996.

A solution of the chromene acetate (1.0 g, 2.13 mmol) in ethanol (20 mL) was treated with 2 N NaOH (20 mL) and stirred at 60° C. for 90 min. The reaction mixture was cooled, acidified with 5 N HCl, and the ethanol was removed in vacuo. The resulting aqueous solution was extracted with ether and concentrated to a light yellow oil that was purified by silica gel chromatography eluting with ethyl acetate (15%, v/v) in hexanes. This yielded the desired chromene-6-ol intermediate as a colorless oil (0.92 g, 98%). $^1$H-NMR (CDCl$_3$/TMS, ppm): 0.87 (m, 12H, 4a'-, 8a'-, 12a'-, 13'-CH$_3$), 1.0-1.6 (m, 24H, 4'-, 8'-, 12'-CH, 1'-, 2'-, 3'-, 5'-, 6'-, 7'-, 9'-, 10'-, 11'-CH$_2$, 2a-CH$_3$), 2.14, 2.18, 2.19 (3×s, 9H, 5a-, 7a-, 8a-CH$_3$), 5.63, 6.55 (2×d, J=10.0 Hz, 2H, CH); $^{13}$C-NMR (CDCl$_3$, ppm): 10.8, 11.6, 12.4 (5a-, 7a-, 8a-CH$_3$), 19.6, 19.7 (CH$_3$), 21.3 (CH$_2$), 22.6, 22.7 (CH$_3$), 24.4, 24.8 (CH$_2$), 25.2 (2a-CH$_3$), 27.9 (CH), 30.9 (3-CH$_2$), 32.7, 32.8 (CH), 37.2, 37.4, 37.5, 39.3, 40.5 (CH$_2$), 50.8 (2-C), 116.2, 117.8, 120.1, 122.3, 123.0, 130.0 (aryl and vinyl C), 144.6, 145.3 (aryl C—O), 169.4 (CO); HRMS (CI, m/z): 428.365275 M+H$^+$, Calc. for C$_{29}$H$_{48}$O$_2$ 428.365431.

A solution of the chromene-6-ol intermediate (0.9 g, 2.1 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with H$_2$O (3×30 ml) and brine (1×30 ml), and then dried with Na$_2$SO$_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with H$_2$O (3×20 mL) and brine (1×20 mL), and then dried with Na$_2$SO$_4$. The resulting solution was concentrated to a light yellow oil and dried in vacuo for 48 h. This yielded 19 as a colorless (0.90 g, 88%). $^1$H-NMR (CDCl$_3$/TMS, ppm): 0.87 (m, 12H, 4a'-, 8a'-, 12a'-, 13'-CH$_3$), 1.0-1.6 (m, 24H, 4'-, 8'-, 12'-CH, 1'-, 2'-, 3'-, 5'-, 6'-, 7'-, 9'-, 10'-, 11'-CH$_2$, 2a-CH$_3$), 2.07, 2.10, 2.19 (3×s, 9H, 5a-, 7a-, 8a-CH$_3$), 4.37 (s, 2H, OCH$_2$), 5.62, 6.50 (2×d, J=10.0 Hz, 2H, CH); $^{13}$C-NMR (CDCl$_3$, ppm): 11.3, 11.5, 12.9 (5a-, 7a-, 8a-CH$_3$), 19.6, 19.7 (CH$_3$), 21.3 (CH$_2$), 22.6, 22.7 (CH$_3$), 24.4, 24.8 (CH$_2$), 25.6 (2a-CH$_3$), 27.9 (CH), 30.9 (3-CH$_2$), 32.7, 32.8 (CH), 37.2, 37.4, 37.5, 39.3, 40.9 (CH$_2$), 60.5 (OCH$_2$), 69.1 (2-C), 118.0, 119.8, 122.8, 122.9, 129.6, 19.8 (aryl and vinyl C), 147.5, 147.8 (aryl C—O), 173.4 (CO); HRMS (CI, m/z): 487.378731 M+H$^+$, Calc. for C$_{31}$H$_{51}$O$_4$ 487.378736.

2-(2,5,7,9-tetramethyl-(2R-(4R,8,12-trimethyltridecyl)chroman-6-yloxy)triethylammonium sulfate (21)

A solution of 2-(2,5,7,8-tetramethyl-(2R-(4R,8R,12-trimethyltridecyl)chroman-6-yloxy))ethan-1-ol (13) (0.1 g, 0.21 mmol) in anhydrous DMF (2 mL) and pyridine (0.6 mL) was treated sulfur trioxide-N,N-dimethylformamide complex (0.16 g, 1.0 mmol), and the resulting solution was stirred for 24 h. The reaction mixture was quenched with 1 N HCl and then extracted with $CH_2Cl_2$ (5×5 mL). Gaseous ammonia was bubbled through the $CH_2Cl_2$ solution for 10 min. The resulting solution was concentrated to a yellow paste and purified by silica gel chromatography eluting with MeOH (10%, v/v) and triethyl amine (2%) in $CHCl_3$. This yielded 21 as a yellow semi-solid (92 mg, 77%) $^1$H-NMR ($CDCl_3$/TMS, ppm): 0.87 (m, 12H, 4a'-, 8a'-, 12a'-, 13'-$CH_3$), 1.0-1.6 (m, 33H, 4'-, 8'-, 12'-CH, 1'-, 2'-, 3'-, 5'-, 6'-, 7'-, 9'-, 10'-, 11'-$CH_2$, 2a-$CH_3$), 1.81 (m, 2H, 3-$CH_2$), 1.95 2.01, 2.05 (3×s, 9H, 5a-, 7a-, 8a-$CH_3$), 2.45 (t, J=6.6 Hz, 2H, 4-$CH_2$), 3.05 (m, 6H, $NCH_2$), 3.79 (m, 2H, $OCH_2$), 4.21 (m, 2H, $OCH_2$); $^{13}$C-NMR ($CDCl_3$, ppm): 9.46 ($CH_3$), 12.4, 12.6, 13.5 (5a-, 7a-, 8a-$CH_3$), 20.3, 20.4 ($CH_3$), 21.3, 21.7 ($CH_2$), 23.3, 23.4 ($CH_3$), 24.5 (2a-$CH_3$), 25.1, 25.5 ($CH_2$), 28.6 (CH), 31.9 (3-$CH_2$), 33.3, 33.4 (CH), 37.9, 38.1, 40.0, 40.8 ($CH_2$), 46.9 ($NCH_2$), 67.4, 71.9 ($OCH_2$), 75.5 (2-C), 118.3, 123.5, 126.5, 128.3 (aryl C), 148.5 (aryl C—O); HRMS (CI, m/z): 554.364102 M–$NH_3$, Calc. for $C_{31}H_{54}O_6S$ 554.364119.

6-(2,5,7,8-tetramethyl-(2R-(4R,8,12-trimethyltridecyl)chroman)acetic acid (22)

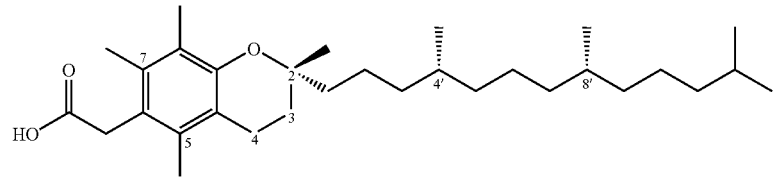

A solution of R,R,R-α-tocopherol (1.0 g, 2.3 mmol) in anhydrous $CH_2Cl_2$ (25 mL) was cooled to 0° C. Diisopropylethyl amine (2 mL, 11.6 mmol) was added followed by the dropwise addition of trifluoromethylsulfonic anhydride (5.0 g, 17.7 mmol). The solution turned to a dark immediately and was allowed to warm to room temperature while stirring for 24 h. The reaction was quenched with $H_2O$ and then was extracted with diethyl ether (2×100 mL). The combined ether layers were washed with 1 N HCl (50 mL), $H_2O$ (50 mL), brine (50 mL), and then dried with $MgSO_4$. The ether solution was concentrated to a yellow oil and purified by silica gel chromatography eluting with ethyl acetate (3%, v/v) in hexane. This yielded the desired triflate intermediate as a yellow oil (1.3 g, quantitative). $^1$H-NMR ($CDCl_3$/TMS, ppm): 0.87 (m, 12H, 4a'-, 8a'-, 12a'-, 13'-$CH_3$), 1.0-1.6 (m, 24H, 4'-, 8'-, 12'-CH, 1'-, 2'-, 3'-, 5'-, 6'-, 7'-, 9'-, 10'-, 11'-$CH_2$, 2a-$CH_3$), 1.81 (m, 2H, 3-$CH_2$), 2.07, 2.13, 2.21 (3×s, 9H, 5a-, 7a-, 8a-$CH_3$), 2.62 (t, J=6.6 Hz, 2H, 4-$CH_2$); $^{13}$C-NMR ($CDCl_3$, ppm): 11.9, 13.2, 14.0 (5a-, 7a-, 8a-$CH_3$), 19.6, 19.7 ($CH_3$), 20.6, 21.0 ($CH_2$), 22.6, 22.7 ($CH_3$), 23.8 (2a-$CH_3$), 24.4, 24.8 ($CH_2$), 28.0 (CH), 31.2 (3-$CH_2$), 32.7, 32.8 (CH), 37.3, 37.4, 37.5, 39.4, 40.0 ($CH_2$), 75.6 (2-C), 118.4, 124.4, 126.7, 128.1 (aryl C), 139.6, 150.9 (aryl C—O); $^{19}$F-NMR ($CDCl_3$, ppm): –73.52; HRMS (CI, m/z): 563.337803 (M+H$^+$, Calc. for $C_{30}H_{50}O_4F_3S$ 563.338192).

A solution of the triflate (1.3 g, 2.31 mmol) in anhydrous DMF (23 mL) was treated with LiCl (0.98 g, 4.62 mmol), triphenylphosphine (0.37 g, 1.4 mmol), 2,6-di-tert-butyl-4-methylphenol (2-3 crystals), tributyl(vinyl)tin (0.73 g, 2.31 mmol), and dichlorobis(triphenylphosphine)-palladium(II) (0.24 g, 0.35 mmol). This mixture was heated to 120° C. and stirred. After 2 h, additional tributyl(vinyl)tin (0.73 g, 2.31 mmol). After 8 h, the reaction was cooled to room temperature and added to a mixture of $H_2O$ (50 mL) and diethyl ether (50 mL). The ether layer was washed with 1 N HCl (6×30 mL) and a saturated solution of KF (6×30 mL). The ether solution was dried with $Na_2SO_4$ and then concentrated to a dark oil. This material was purified by silica gel chromatography eluting with ethyl acetate (3%, v/v) in hexane yielding the 6-vinylchroman intermediate as a clear oil (0.38 g, 38%). $^1$H-NMR ($CDCl_3$/TMS, ppm): 0.87 (m, 12H, 4a'-, 8a'-, 12a'-, 13'-$CH_3$), 1.0-1.6 (m, 24H, 4'-, 8'-, 12'-CH, 1'-, 2'-, 3'-, 5'-, 6'-, 7'-, 9'-, 10'-, 11'-$CH_2$, 2a-$CH_3$), 1.86 (m, 2H, 3-$CH_2$), 2.20, 2.24, 2.28 (3×s, 9H, 5a-, 7a-, 8a-$CH_3$), 2.62 (t, J=6.8 Hz, 2H, 4-$CH_2$), 5.18, 5.56 (2×dd, $J_{gem}$=2.3 Hz, $J_{cis}$=11.2 Hz, $J_{trans}$=18.7 Hz, 2H, =$CH_2$), 6.77 (dd, J=18.7, 11.2 Hz, 1H, CH); $^{13}$C-NMR ($CDCl_3$, ppm): 11.9, 16.3, 17.2 (5a-, 7a-, 8a-$CH_3$), 19.7, 19.8 ($CH_3$), 20.8, 21.1 ($CH_2$), 22.6, 22.7 ($CH_3$), 23.9 (2a-$CH_3$), 24.5, 24.8 ($CH_2$), 28.0 (CH), 31.2 (3-$CH_2$), 32.7, 32.8 (CH), 37.3, 37.5, 37.5, 39.4, 40.1 ($CH_2$), 74.9 (2-C), 116.7, 119.0, 122.0, 129.8, 131.2, 132.8, 136.8 (aryl/vinyl C), 150.9 (aryl C—O); HRMS (CI, m/z): 440.401602 (M+H$^+$, Calc. for $C_{31}H_{52}O$ 440.401812).

A solution of the 6-vinylchroman intermediate (0.12 g, 0.27 mmol) in anhydrous THF (1 mL) was cooled to 0° C. and treated with 9-BBN (0.60 mL, 0.5 M in THF, 0.3 mmol). The reaction mixture was heated to reflux for 8 h. The reaction was quenched with water (1.5 mL) and treated with $NaBO_3.4H_2O$ and the resulting slurry was stirred overnight. Diethyl ether (4 mL) and the reaction mixture were extracted with $CH_2Cl_2$ (2×20 mL). The organic layers were concentrated to a clear oil that was purified by silica gel chromatography eluting with ethyl acetate (50%, v/v) in hexane. This yielded the desired 6-(2-hydroxyethyl)chroman intermediate as a colorless oil (30 mg, 24%). $^1$H-NMR ($CDCl_3$/TMS, ppm): 0.87 (m, 12H, 4a'-, 8a'-, 12a'-, 13'-$CH_3$), 1.0-1.6 (m, 24H, 4'-, 8'-, 12'-CH, 1'-, 2'-, 3'-, 5'-, 6'-, 7'-, 9'-, 10'-, 11'-$CH_2$, 2a-$CH_3$), 1.81 (m, 2H, 3-$CH_2$), 2.17, 2.24, 2.28 (3×s, 9H, 5a-, 7a-, 8a-$CH_3$), 2.68 (t, J=6.8 Hz, 2H, 4-$CH_2$), 3.01 (t, J=7.5 Hz, 2H, Ar—$CH_2$), 3.74 (t, J=7.5 Hz, 2H, $OCH_2$); $^{13}$C-NMR ($CDCl_3$, ppm): 12.0, 15.1, 16.0 (5a-, 7a-, 8a-$CH_3$), 19.6, 19.7 ($CH_3$), 20.6, 21.0 ($CH_2$), 22.6, 22.7 ($CH_3$), 23.8 (2a-$CH_3$), 24.4, 24.8 ($CH_2$), 28.0 (CH), 31.2 (3-$CH_2$), 32.7, 32.8 (CH), 37.3, 37.4, 37.5, 39.4, 40.0 ($CH_2$), 62.2 ($OCH_2$), 72.6 (2-C), 116.8, 122.3, 124.9, 132.4, 133.9 (aryl C), 150.1 (aryl C—O); HRMS (CI, m/z): 458.412154 (M+H$^+$, Calc. for $C_{31}H_{54}O_2$ 458.412384).

A solution of pyridinium chlorochromate (32 mg, 0.1 mmol) in anhydrous $CH_2Cl_2$ (0.5 mL) was treated with a solution of the 6-(2-hydroxyethyl)chroman intermediate (32 mg, 0.07 mmol) in CH$_2$Cl$_2$ (0.5 mL). The reaction was stirred for 2 h at which time no starting material was visible by thin layer chromatography. Diethyl ether (2 mL) was added and the resulting solution was filtered through a thin pad of celite. The filtrate as concentrated and yielded a yellow oil (20 mg). This oil was dissolved in t-BuOH (0.5 mL) and treated with phosphate buffer (0.5 mL, 1 N, pH=4.0), 2-methyl-2-butene (0.1 mL) and NaClO$_2$ (5.4 mg, 0.05 mmol). After stirring for 40 min, the reaction mixture was extracted with CHCl$_3$ (6×10 mL) and the combined organic layers were dried with Na$_2$SO$_4$. The CHCl$_3$ solution was concentrated to a yellow oil that was purified by preparative thin layer chromatography eluting with ethyl acetate (30%, v/v) and acetic acid (1%) in hexanes. This yielded 22 as colorless oil (20 mg, 63%).

$^1$H-NMR (CDCl$_3$/TMS, ppm): 0.87 (m, 12H, 4a'-, 8a'-, 12a'-, 13'-CH$_3$), 1.0-1.6 (m, 24H, 4'-, 8', 12'-CH, 1'-, 2'-, 3'-, 5'-, 6'-, 7'-, 9'-, 10'-, 11'-CH$_2$, 2a-CH$_3$), 1.81 (m, 2H, 3-CH$_2$), 2.17, 2.24, 2.28 (3×s, 9H, 5a-, 7a-, 8a-CH$_3$), 2.66 (t, J=6.8 Hz, 2H, 4-CH$_2$), 3.71 (s, 2H, CH$_2$COOH); $^{13}$C-NMR (CDCl$_3$, ppm): 12.0, 15.3, 16.2 (5a-, 7a-, 8a-CH$_3$), 19.6, 19.7 (CH$_3$), 20.6, 21.0 (CH$_2$), 22.6, 22.7 (CH$_3$), 23.8 (2a-CH$_3$), 24.4, 24.8 (CH$_2$), 28.0 (CH), 28.9, 31.2 (3-CH$_2$), 32.7, 32.8 (CH), 37.3, 37.4, 37.5, 39.4, 40.0 (CH$_2$), 72.6 (2-C), 117.1, 122.2, 124.9, 132.4, 132.7 (aryl C), 150.2 (aryl C—O), 179.2 (COOH); HRMS (CI, m/z): 472.391583 (M+H$^+$, Calc. for C$_{31}$H$_{52}$O$_3$ 472.391644).

2,5,7,8-tetramethyl-(2R-(heptyl)chroman-6-yloxy) acetic acid (23)

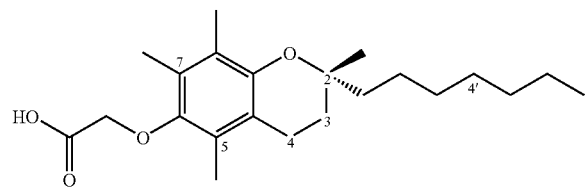

A solution of hexyltriphenyphosphonium bromide (0.880 g, 2.05 mmol) in 11.2 ml of anhydrous DME was stirred at room temperature while 0.86 ml (2.06 mmol) of 2.4 M n-butyllithium in hexane was added. The resulting red solution was stirred for 2 h at room temperature, then a solution of [(+)S-6-Benzyloxy-2,5,7,8-tetramethylchroman-2-carbaldehyde (306 mg, 0.944 mmol) in 3 ml of anhydrous DME was added and stirring was continued for 3 h at 65-75° C. After cooling, the reaction mixture was poured into cold dilute H$_2$SO$_4$ and work up ether was carried out in the usual manner. The ether was concentrated in vacuo to afford the oily material. Product was isolated using column chromatography and eluted with chloroform to yield 46% of the product. The mixture of cis and trans alkene was dissolved in 30 ml of ethyl acetate and 50 mg of 5% palladium on carbon was added, and the mixture was shaken under 40 psi of H2 for 10 hrs and then filtered through Celilte and rinsed well with ethyl acetate. The filtrate was concentrated and purified by silica gel chromatography eluting with EtOAc in hexane (1:9) to give (2R) 2,5,7,8-tetramethyl-2-(heptyl)-6-chromanol (60% yield) $^1$H-NMR (CDCl$_3$/TMS, ppm):0.89 (s, 3H), 1.3-1.5 (m, 15H), 1.89 (m, 2H), 2.2 (s, 3H), 2.08 (s, 3H), 2.23 (s, 3H), and 2.48 (t, J=6.5 Hz, 2H); MS (CI, m/z):305.35 M+H$^+$, Calc. for C$_{20}$H$_{32}$O$_2$ 304.4746).

A solution of 2,5,7,8-tetramethyl-2-(heptyl)chromanol (0.353 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with H$_2$O (3×30 ml) and brine (1×30 ml), and then dried with Na$_2$SO$_4$. The ether solution was concentrated to a yellow oil that was purified by silica gel chromatography eluting with 19% (v/v) EtOAc and 2% acetic acid in hexanes. The resulting liquid was dissolved in diethyl ether (30 ml), washed with H$_2$O (3×20 mL) and brine (1×20 mL), and then dried with Na$_2$SO$_4$. The resulting solution was concentrated and dried in vacuo for 48 h. This yielded compound 23 in 36% yield. $^1$H-NMR (CDCl$_3$/TMS, ppm): $^1$H-NMR (CDCl$_3$/TMS, ppm): 0.88 (s, 3H), 1.2-1.5 (m, 15H), 1.88 (m, 2H), 2.1 (s, 3H), 2.18 (s, 3H), 2.2 (s, 3H), 2.55 (t, J=6.5 Hz, 2H) and 4.78 (s, 2H); HRMS (CI, m/z):363.2535 (M+H$^+$, Calc. for C$_{22}$H$_{35}$O$_4$ 363.2541).

2,5,7,8-tetramethyl-(2R-(tridecyl)chroman-6-yloxy) acetic acid (24)

The compounds 24 and 25 were synthesized in manner identical to the synthesis of 23 using appropriate phosphonium bromide.

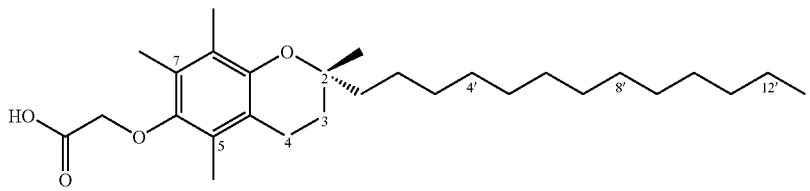

$^1$H-NMR (CDCl$_3$TMS, ppm): 0.83 (s, 3H), 1.25-1.57 (m, 27H), 1.88 (m, 2H), 2.1 (s, 3H), 2.18 (s, 3H), 2.20 (s, 3H), 2.55 (t, J=6.6 Hz, 2H) and 4.48 (s, 2H); MS (CI, m/z): 447.14 M+H$^+$, Calc. For C$_{28}$H$_{46}$O$_4$ 446.6732.

2,5,7,8-tetramethyl-(2R-(heptadecyl)chroman-6-yloxy)acetic acid (25)

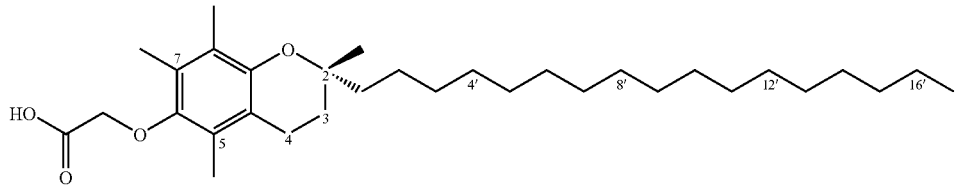

$^1$H-NMR (CDCl$_3$/TMS, ppm): 0.86 (s, 3H), 1.15-1.67 (m, 35H), 1.88 (m, 2H), 2.16 (s, 3H), 2.20 (s, 3H), 2.23 (s, 3H), 2.55 (t, J 10=6.4 Hz, 2H) and 4.78 (s, 2H); MS (CI, m/z): 503.45 M+H$^+$, Calc. For C$_{32}$H$_{54}$O$_4$ 502.781.

2,5,7,8-tetramethyl-2R-(4,8,-dimethyl-1,3,7 E.Z, nonotrien)chroman-6-yloxy)acetic acid (26)

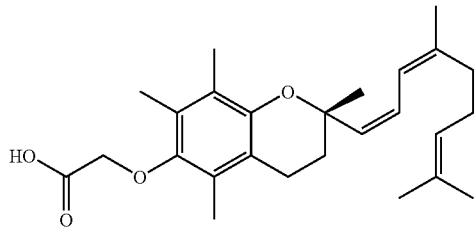

Compound 26 was synthesized in a manner identical to the synthesis of compound 18 using nerol instead of pseudoionol. $^1$H-NMR (CDCl$_3$/TMS, ppm): 1.24 (s, 3H, 2aCH$_3$), 1.63 (m, 1H), 1.68 (s, 3H), 1.74 (s, 6H), 1.92 (m, 6H), 2.18 (s, 3H), 2.29 (S, 6H), 2.43 (t, J=6.6 Hz, 2H, 4-CH$_2$), 4.68 (s, 2H, OCH$_2$), 5.64 (m, 2H) and 5.27 (m, 1H); MS (CI, m/z): 413.24 M+H$^+$, Calc. for C$_{26}$H$_{36}$O$_4$ 412.0115.

E.Z, RS, RS, RS-(phytyltrimethylbenzenethiol-6-yloxy)acetic acid (27)

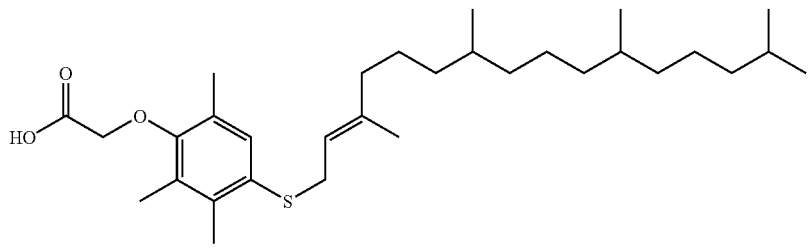

2,3,6-trimethylphenol (1.6 g, 11.8 mmol) was dissolved in 50 mL of anhydrous methanol which had been deoxygenated by bubbling with nitrogen. Ammonium thiocyanate (2.2 g, 28.9 mmol) was added to this solution which was then cooled to 0° C. and bubbled with chlorine gas. The initially colorless homogeneous solution becomes pink and then green with the formation of a white precipitate. The solution was stirred for 1 h at 0° C. and then for a further hour at 20° C. The dissolved chlorine was removed by bubbling with nitrogen and the precipitate removed by filtration. Evaporation of the filtrate under reduced pressure followed by drying under high vacuum (0.1 torr) yielded 2.20 g (97%) of 2,3,5-Trimethyl-4-hydroxyphenylthiocyanate in a form pure enough for the next step in the synthesis. An analytical sample was recrystallized from hexanes white crystals, mp 100.3° C. $^1$H NMR (CDCl$_3$) δ 7.2 (s, 1 H), 5.0 (s, 1 H) 2.4 (s, 3 H), 2.2 (s, 6 H).

2,3,5-Trimethyl-4-hydroxyphenylthiocyanate (2 g, 10.35 mmol) was dissolved in 100 mL of anhydrous ether containing 25 mL of anhydrous tetrahydrofuran. This solution was added dropwise over 1 h to 100 mL of anhydrous ether containing LiAlH$_4$ (0.9 g, 24 mmol) at room temperature. After a further hour at 20, C, the unreacted LiAlH$_4$ was destroyed by cooling the heterogeneous mixture to 0° C. and adding moist ether (50 mL), H$_2$O (50 mL), and 1 N HCl (50 mL). A further 50 mL of water was added and the organic phase was separated and washed with water (2×50 mL), NaHCO$_3$ solution (2×50 mL), water (2×50 mL), and saturated NaCl (50 mL). The organic phase was dried over anhydrous MgSO$_4$ and filtered and the solvent removed under reduced pressure. Silica gel column chromatography with 5% ethyl acetate in hexane gave 1.8 g (90%) of 2,3,5-trimethyl-4-hydroxybenzenethiol as a white powder, mp 86° C. [Lit.[1] mp 86° C.].

Solution of 2,3,5-trimethyl-4-hydroxybenzenethiol (3 g, 17.83 mmol), isophytol (4.8 g, 16.19 mmol), anhydrous zinc chloride (1.2 g, 8.8 mmol) and 0.2 mL of glacial acetic acid in 30 mL of absolute ether was refluxed for 1 h. The solvent was then removed in vacuo at 50° C. and the red oil obtained was dissolved in a mixture of 50 mL of petroleum ether and 20 mL of 70% aqueous methanol. The ether layer was dried (Na$_2$SO$_4$) and evaporated in vacuo to give a red oil, which was purified by silica gel chromatography eluting with hexans: ether (9:1) to give 3 g (38%) E.Z, RS, RS, RS-Phytyltrimethylhydroxybenzenethiol as yellow oil. $^1$H NMR (CDCl$_3$)

δ 7.11 (s, 1 H, Ar—H), 5.23 (t, 1 H, vinylic-H), 4.62 (s, 1 H, OH), 3.34 (d, 2 H, Ar—S—CH$_2$—), 2.41 (s, 3 H, Ar—CH$_3$), 2.19 (s, 3 H, Ar—CH$_3$), 2.18 (s, 3 H, Ar—CH$_3$), 0.83-1.92 (m, 39 H, Phytol chain).

A solution of phytyltrimethylhydroxybenzenethiol (3 g, 6.7 mmol) in N,N-dimethyl-formamide (80 mL) was treated with methyl bromoacetate (7.4 g, 48.3 mmol) and an excess of powdered NaOH (7 g, 175 mmol). The resulting pink oil was stirred at RT for 24 h. The reaction mixture was acidified with 5 NHCl and extracted with ether (3×150 mL). The combined ether layers were washed with H$_2$O (3×150 mL) and brine (1×150 mL), and then dried (Na$_2$SO$_4$). The ether solution was concentrated to a yellow oil that was purified by silica gel chromatography eluting with 20% EtOAc in hexane to give 3 g (88%) of E.Z, RS, RS, RS — (phytyltrimethylbenzenethiol-6-yloxy)acetic acid as a yellow oil. $^1$H NMR (CDCl$_3$) δ 10.90 (s, 1 H, COOH), 8.08 (s, 1 H, Ar—H), 5.30 (t, 1 H, vinylic-H), 4.35 (s, 2 H, CH$_2$COOH), 3.42 (d, 2 H, Ar—S—CH$_2$—), 2.34 (s, 3 H, Ar—CH$_3$), 2.25 (s, 3 H, Ar—CH$_3$), 2.22 (s, 3 H, Ar—CH$_3$), 0.83-1.94 (m, 39 H, Phytyl chain). HRMS (CI, m/z): 504.362821 (M+H$^+$, Calc. for C$_{31}$H$_{53}$O$_3$S 504.363718).

(R)-2-[(2,5,7,8-tetramethyl-2-(3 propene methyl ester) chroman-6-yloxy]acetic acid (28)

To a slurry of (carbomethoxymethyl)triphenyl phosphonium bromide (1.8 gm, 4.32 mmol) in 12 ml of THF at ° C. was added 1.66 ml of n-BuLi (2.5M in hexane) dropwise. The resulting solution was removed to room temperature for 2 h, and then a solution of (+)S-6-[dimethyl(1,1-dimethylethyl)silyl]-2,5,7,8-tetramethyl chroman-2-carbaldehyde (1.31 g, 3.76 mmol) in 7 ml THF was added via cannula. The solution was stirred at room temperature for 44 hr and then 10 ml of 1N aq. HCl was added. The layer were separated and then aq. phase was extracted with ether (3×15 ml). The combined organic layer were washed with brine, dried over Na$_2$SO$_4$ and filtered. After concentration of the filtrate, the crude alkene was purified by flash chromatography eluting with dichloromethane to give mixture of the cis and trans alkene in 93% yield. The silyl ether mixture of cis and trans alkene (3.76 mmol) was dissolved in THF and tetra-n-butylammoniumfluoride (0.041 mole) was added. After being stirred at 23° C. for 1.5 h, the mixture was poured into water and extracted into ether. The ether extract was dried concentrated and purified by silica gel chromatography eluting with EtOAc in hexane (3:7) and both the cis and trans isomer of 2,5,7,8-tetramethyl-2R-(3'propenemethyl ester)-6-chromanol were isolated and characterized (68% yield) $^1$H-NMR (CDCl$_3$/TMS, ppm): 1.65 (s, 3H, 2a CH$_3$), 2.12 (m, 2H, 3CH$_2$), 2.39 (s, 9H, CH$_3$), 2.48 (m, 2H, 4 CH$_2$), 3.78 (s, 3H, OCH$_3$), 6.11 (d, 1H, CH=) and 7.13 (d, 1H, CH=).

A solution of 2,5,7,8-tetramethyl-2R-(3'propene methyl ester)6-chromanol (0.353 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with H$_2$O (3 ×30 ml) and brine (1×30 ml), and then dried with Na$_2$SO$_4$. The ether solution was concentrated to a yellow oil that was purified by silica gel chromatography eluting with 19% (v/v) EtOAc and 2% acetic acid in hexanes. The resulting liquid was dissolved in diethyl ether (30 ml), washed with H$_2$O (3×20 mL) and brine (1×20 mL), and then dried with Na$_2$SO$_4$. The resulting solution was concentrated and dried in vacuo for 48 h. This yielded compound 28 in 40% yield. $^1$H-NMR (CDCl$_3$/TMS, ppm): 1.68 (s, 3H, 2a CH$_3$), 2.11 (m, 2H, 3CH$_2$), 2.36 (s, 9H, CH$_3$), 2.56 (m, 2H, 4 CH$_2$), 3.70 (s, 3H, OCH$_3$), 4.78 (s, 2H, OCH$_2$), 6.03 (d, 1H, CH=) and 7.03 (d, 1H, CH=); MS (CI, m/z):337.24 M+H$^+$, Calc. for C$_{18}$H$_{24}$O$_6$ 336.3867.

2,5,7,8-tetramethyl-(2R-(methyl propionate)chroman-6-yloxy) acetic acid (29)

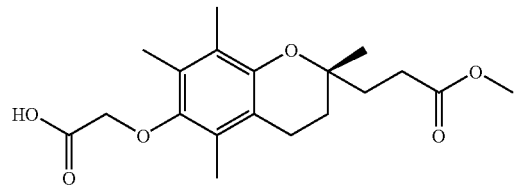

The mixture of cis and trans alkene 2,5,7,8-tetramethyl-2R-(3 propene methylester)-6-chromanol was dissolved in 30 ml of ethyl acetate and 50 mg of 5% palladium on carbon was added, and the mixture was shaken under 40 psi of H2 for 24 hrs and then filtered through Celilte and rinsed well with ethyl acetate. The filtrate was concentrated and purified by silica gel chromatography eluting with EtOAc in hexane (1:9) to give compound # 29. $^1$H-NMR (CDCl$_3$/TMS, ppm): 1.62 (s, 3H, 2a CH$_3$), 2.0-2.3 (m, 6H, CH$_2$), 2.41 (s, 9H, CH$_3$), 2.53 (m, 2H, 4 CH$_2$), 3.67 (s, 3H, OCH$_3$) and 4.88 (s, 2H, OCH$_2$); MS (CI, m/z): 339.34 M+H$^+$, Calc. for C$_{18}$H$_{26}$O$_6$ 338.4025.

EXAMPLE 3

Synthesis of all-racemic 1-aza-α-tocopherol analogs; Phytyltrimethylhydroquinone (31)

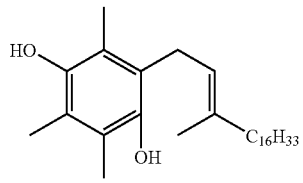

The solution of trimethylhydroquinone (30, 7.5 g, 49.28 mmol), isophytol (12 g, 40.47 mmol), anhydrous zinc chloride (3 g. 22.01 mmol) and 0.4 mL of glacial acetic acid in 60 mL of absolute ether was refluxed for 1 h. The solvent was then removed in vacuo at 50° C. and the slurry obtained was dissolved in a mixture of 50 mL of petroleum ether and 20 mL of 70% aqueous methanol. The emulsion formed was destroyed by the addition of 20 mL of ether. The ether layer was dried (Na$_2$SO$_4$) and evaporated in vacuo to give a red solid paste that was triturated vigorously with 70 mL of petroleum ether. After cooling to −78° C., the suspension was centrifuged and the supernatant petroleum ether was decanted. Cold petroleum ether (10 mL) was added to the crystalline mass, and the operation was twice repeated to give 10 g (47%) of sticky white solid, which was used in the next step without further purification.

Phytyltrimethylhydroquinone diacetate (32)

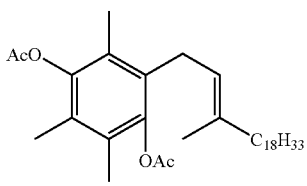

The crude phytyltrimethylhydroquinone (31, 9 g, 20.1 mmol) was dissolved in dry pyridine (90 g) and acetic anhydride (90 g). After storage for 10 h at room temperature, the mixture was poured onto ice (200 mL) and extracted with ether (2×100 mL). The ether solution was washed with 3N sulfuric acid (2×100 mL), 10% sodium bicarbonate solution (2×100 mL), and again water (2×100 mL), dried ($Na_2SO_4$), and evaporated to yield 10.2 g (95%) of diacetate (32) as a light yellow oil. The oil was used in the next step without further purification.

Trimethyl(3,7,11,15-tetramethyl-3-benzamidohexadecyl)hydroquinone diacetate (33)

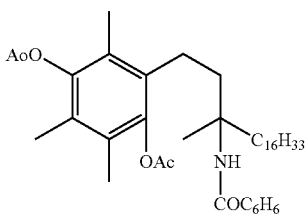

To a mixture of benzonitrile (10 g, 96.97 mmol), concentrated sulfuric acid (10 g) and glacial acetic acid (40 mL) was added, with stirring at 0° C., the diacetate (32, 10 g, 19.43 mmol). The solution was stored for 10 h at room temperature, then poured onto ice (150 mL) and extracted with ether (3×100 mL). The ether extracts were washed neutral with water (3×100 mL), and saturated sodium bicarbonate solution, dried ($Na_2SO_4$) and evaporated in vacuo. The crude product (21 g) was chromatographed on silica gel eluting with petroleum ether:ether (9:1). The unchanged benzonitrile was first removed. Elution with ether then afforded 11 g (88%) of product which was crystallized from petroleum ether to give analytical sample (33) m.p. 90-92° C. (lit.1 94-95° C.).

2,5,7,8-Tetramethyl-2(4,8,12-trimethyltridecyl)3,4-dihydroquinolin-6(2H)-one (37)

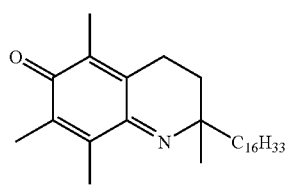

To a solution of the diacetate (33, 13 g, 20.4 mmol) in 60 mL of methanol, solid potassium hydroxide (11 g) was added and the mixture was refluxed under argon for 45 min. After cooling, the solution was diluted with ice-water (100 mL), and extracted under carbon dioxide with ether (3×100 mL) yielding 10 g (88%) of crude hydroquinone (34).

A solution of this product (34, 10 g, 18.1 mmol) in absolute ether (110 mL) was added dropwise with stirring during 20 min. to a suspension of lithium aluminum hydride (20 g, 527 mmol) in absolute ether (110 mL). The mixture was refluxed for 14 h and then hydrolyzed under carbon dioxide by the dropwise addition of methanol (10 mL) followed by 3N hydrochloric acid (30 mL). After extraction with ether (3×200 mL), the crude solid benzylamino derivative (35, 8.4 g, 86%) was obtained.

This material (35, 8.4 g, 15.6 mmol) was dissolved in glacial acetic acid (120 mL) and hydrogenated at 50° C. and atmospheric pressure in the presence of 2 g of palladium on charcoal (5%) at room temperature for 22 h (or until the hydrogen absorption ceased). After cooling, the catalyst was filtered off, and the solution was diluted with water (50 mL), extracted with ether (3×80 mL) and dried ($Na_2SO_4$).

To this dry and neutral ether solution of 36 was added fresh silver oxide (2.1 g, 8.93 mmol), and the suspension was stirred for 14 h. After filtration under argon and evaporation, 4 g of the crude iminoquinone (37) was obtained, which was chromatographed on silica gel eluting with hexanes:ether (200:1) to yield 2.4 g (63%) of pure yellow oil. HMRS (cl, m/z): 428.389883 (M+H$^+$, Calc. For $C_{29}H_{49}NO$ 428.389241).

1-Aza-α-tocopherol (38)

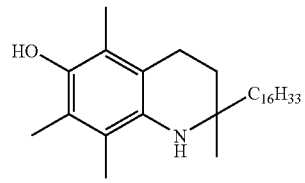

The iminoquinone (37, 1.34 g, 3.133 mmol) in 10 mL of ether was hydrogenated at room temperature and atmospheric pressure in the presence of 190 mg of Lindlar's catalyst. After 20 h, the catalyst was filtered off under argon and the filtrate was evaporated in vacuo to give 810 mg (60%) of crude red oil, which was used in the next step without further purification.

1-Aza-α-tocopherol-6-yloxyl-acetic acid (39) and
1-Aza-α-tocopherol-6-yloxyl-methyl acetate (40)

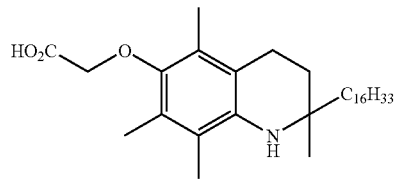

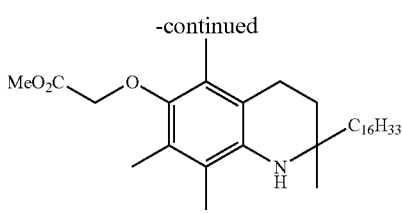

A solution of 1-Aza-α-tocopherol (38, 800 mg, 1.86 mmol) in DMF (30 mL) was treated with methyl bromoacetate (2.1 g, 13.4 mmol) and an excess of powdered NaOH (1.9 g, 48.4 mmol). The resulting yellow suspension was stirred vigorously for 24 h at room temperature. The reaction mixture was acidified with 5N HCl to pH6, and extracted with diethyl ether (3×30 mL). The combined ether layers were washed with water (3×40 mL), brine (1×40 mL), and then dried (Na2SO4). The ether solution was concentrated to a yellow oil that was purified by silica gel chromatography eluting with $CH_2Cl_2$:MeOH:Hac (97:2:1) to give 300 mg (33%) of sticky yellow solid (39). $^1$H-NMR (CDCl$_3$, ppm) 4.30 (s, 2H, OCH$_2$), 3.30 (s, 1H, NH), 2.59 (t, 2H, Ar—CH$_2$), 2.18 (s, 3H, Ar—CH$_3$), 2.12 (s, 3H, Ar—CH$_3$), 2.00 (s, 3H, Ar—CH$_3$), 1.80-0.84 (m, 38H, Ar—CH$_2$CH$_2$, NCCH$_3$ and phytyl chain); $^{13}$C-NMR (CDCl$_3$, ppm): 12.01, 12.77, 12.96, 19.60, 19.67, 19.72, 21.09, 22.60, 22.71, 24.42, 24.79, 26.56, 27.95, 32.11, 32.74, 37.26, 37.37, 37.42, 37.55, 37.65 39.34, 41.36, 50.92, 69.50 (aliphitic C), 117.69, 118.55, 125.99, 126.39, 138.07, 146.05 (Ar—C), 173.18 (COOH); (HRMS (CI, m/z): 488.411055 (M+H$^+$, Calc for $C_{31}H_{53}NO_3$ 488.410370) and 150 mg (17%) of yellow oil (40). $^1$H-NMR (CDCl$_3$/TMS, ppm) 4.31 (s, 2H, OCH$_2$), 3.85 (S, 3H, CO$_2$CH$_3$), 3.32 (S, 1H, NH), 2.61 (T, 2H, Ar—CH$_2$), 2.23 (S, 3H, Ar—CH$_3$), 2.17 (S, 3H, Ar—CH$_3$), 2.01 (S, 3H, Ar—CH$_3$), 1.81-0.86 (M, 38H, Ar—CH$_2$CH$_2$, NCCH$_3$ and phytyl chain); $^{13}$C-NMR (CDCl$_3$, ppm) 11.96, 12.67, 12.90, 19.57, 19.63, 19.69, 21.06, 21.95, 22.57, 22.68, 24.38, 24.74, 26.49, 27.91, 32.25, 32.67, 32.70, 37.21, 37.33, 37.53, 39.31, 41.68, 50.43, 51.87, 69.97, (aliphitic C), 116.98, 117.72, 126.01, 126.36, 138.43, 146.18 (Aryl C), 169.83 (C=O); HRMS (CI, m/z): 502.425330 (M+H$^+$, Calc. for $C_{32}H_{55}NO_3$ 502.426020).

1-Aza-N-methyl-α-tocopherol-6-yloxyl-methyl acetate (41)

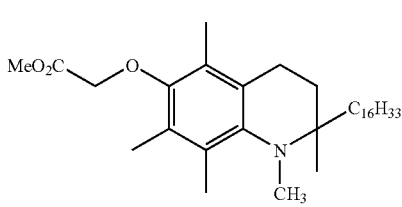

Following the literature procedure 2, a mixture of powdered KOH (500 mg, 7.77 mmol) in DMSO (30 mL) was stirred at 0° C. for 5 min. The methyl acetate (40, 1.3 g, 23.32 mmol) was added, followed immediately by the addition of CH$_3$I (3.3 g, 23.32 mmol). Stirring was continued for 0.5 h (0° C.) after which the mixture was poured into water. Extracts (CH2Cl2, 3×40 mL) of the final mixture were combined, washed with water (40 mL), brine (40 mL), dried (MgSO4) and then evaporated. The resulting yellow oil was chromatographed over silica gel eluting with 5% ETOAC in hexane to give 810 mg (60%) of light yellow oil. $^1$H-NMR (CDCl$_3$/TMS, ppm) 4.34 (s, 2H, OCH$_2$), 3.84 (s, 3H, CO$_2$CH$_3$), 2.55 (t, 2H, Ar—CH$_2$), 2.49 (s, 3H, NCH$_3$), 2.24 (s, 3H, Ar—CH$_3$), 2.20 (s, 3H, Ar—CH$_3$), 2.13 (s, 3H, Ar—CH$_3$), 1.82-0.82 (m, 38H, Ar—CH$_2$CH$_2$, NCCH$_3$ and phytyl chain); $^{13}$C-NMR (CDCl$_3$, ppm) 11.72, 13.12, 14.27, 19.55, 19.68, 20.93, 22.57, 22.66, 22.88, 24.35, 24.74, 25.33, 25.37, 27.90, 32.59, 32.71, 37.23, 37.33, 37.51, 37.63, 38.49, 39.06, 39.29, 51.14, 69.57 (aliphitic C), 125.34, 126.36, 127.42, 130.32, 143.89, 150.33 (Ar—C), 169.73 (C=O). The compound 41 was used in the next step without further purification.

1-Aza-N-methyl-α-tocopherol-6-yloxyl-acetic acid (42)

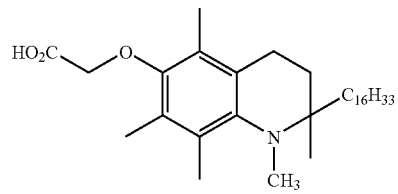

To the mixture of the ester (41, 740 mg, 14.34 mmol) in ethanol (34 mL) was added dropwise 2N NaOH (9 mL, 10 eq. 14.34 mmol). After stirring the light yellow solution at room temperature for 4 h, the reaction mixture was acidified with 2N HCl to pH6, and then extracted with EtOAc (3×100 mL) and the combined organic layers were washed with water (2×100 mL), brine (1×100 mL), dried (MgSO4), and evaporated to give a light yellow oil. The oil was chromatographed over silica gel eluting with 1% HOAc, 30% EtOAc in hexans to give 650 mg (90%) of the product (42) as a colorless oil.

$^1$H-NMR (CDCl$_3$/TMS, ppm) 10.43 (s, 1H, CO$_2$H), 4.37 (s, 1H, OCH$_2$), 2.51 (t, 2H, Ar—CH$_2$), 2.43 (s, 3H, NCH$_3$), 2.22 (Ar—CH$_3$), 2.12 (s, 3H, Ar—CH$_3$), 1.81-0.80 (m, 38H, Ar—CH$_2$CH$_2$, NCCH$_3$ and phytyl chain); $^{13}$C-NMR (CDCl$_3$, ppm): 11.77, 13.18, 14.28, 19.68, 19.73, 20.80, 20.96, 22.62, 22.72, 23.00, 24.00, 24.41, 24.80, 25.37, 27.80, 32.77, 37.28, 37.30, 37.74, 38.00, 39.00, 39.35, 54.69, 69.17 (aliphitic C), 125.11, 126.55, 127.20, 130.63, 142.00, 149.60 (Ar—C), 173.62 (COOH); HRMS (CI, m/z): 502.426327 (M+H$^+$, Calc. For $C_{32}H_{55}NO_3$ 502.426020).

6-(2,4-Dinitrophenylazo(2,5,7,8-tetramethyl-2-(4,8, 12-trimethyl tridecyl)-1,2,3,4-tetrahydroquinoline (43)

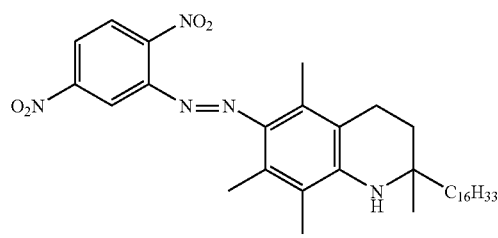

2,4-dinitrophenylhydrazine (1.95 g, 9.82 mmol) was dissolved in 34 mL of hot absolute ethanol and 3.4 mL of concentrated sulfuric acid was carefully added. The hot red solution was cooled to room temperature and the iminoquinone (37, 1.00 g, 2.34 mmol) in 12 mL of absolute ethanol was added with stirring. The mixture was allowed to stand at room temperature for 70 h, then diluted with 120 mL of water and extracted with ether (3×100 mL). The combined ether extracts were washed neutral with water (6×100 mL), dried (NaSO$_4$), and evaporated in vacuo to give 2.9 g of a partly crystalline dark violet mass. This product was chromatographed over silica gel eluting with 5% ether in petroleum ether to yield 1.35 g (95%) of violet crystals (43), m.p. 72-73° C. (lit.[1] 73-75). HRMS (CI, m/z): 608.417199 (M+H$^+$, Calc. For C35H53N5O4 608.417581).

EXAMPLE 3

Synthesis of 2,5,7,8-tetramethyl-2R-(4,8,12-trimethyl-3,7,11 E:E tridecatrien)chroman-6-yloxy)acetic acid (44)

the solvent removed under reduced pressure. The crude product was further purified by column chromatography on silica gel (CH$_2$Cl$_2$:ethyl acetate, 9:1) to yield 1.85 g (79%) of a white waxy solid. $^1$H-NMR (300 MHz)_5.15 (m, 3H, HC=C), 4.44 (s, 2H, COCH$_2$O), 2.61 (t, 2H, C-4 CH$_2$), J=7 Hz), 2.21 (s, 3H), 2.17 (s, 3H), 2.14 (s, 3H), 2.16-1.90 (m, 10H), 1.82 (m, 2H, C-3 CH$_2$), 1.70 (s, 3H, C-2 CH$_3$), 1.65 (overlapped multiplet, 2H), 1.62 (s, 9H, C=CCH$_3$), 1.28 (s, 3H, CH$_3$). $^{13}$C-NMR (75 MHz, CDCl$_3$) 174.2, 148.9, 147.5, 135.6, 135.4, 131.7, 127.8, 125.9, 124.8, 124.7, 124.6, 123.7, 118.2, 77.6, 75.2, 69.6, 40.1, 31.6, 27.1, 27.0, 26.1, 24.2, 22.6, 21.0, 18.1, 16.4, 16.3, 13.1, 12.3, 12,2. Only 30 of the potentially 31 distinct carbon atoms are apparent in the spectrum. Two peaks, likely in the aliphatic region, are not resolved at this field strength. EI-MS m/z 482 (M$^+$, 100), 263 (15), 261 (11), 224 (15), 223 (97), 222 (10), 203 (6), 165 (18), 137 (13), 95 (9), 81 (35), 69 (89)

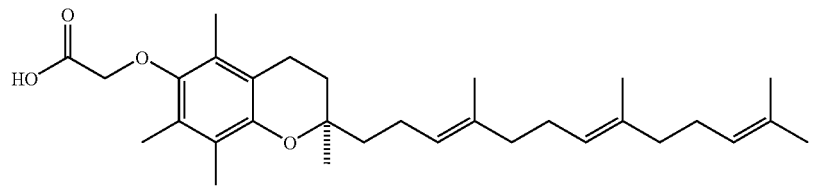

The starting material was 89% pure R,R,R,-alpha-tocotrienol obtained as a gift from Dr. Kai Baldenius, BASF Aktiengesellschaft, Ludwigshafen, Germany. The material was provided to Dr. Jeffrey Atkinson, Brock University, Ontario, Canada who prepared 44, also named 6-0-carboxymethyl alpha-tocotrienol or 6-0 CM-α-Toc, as a service. The starting material was subjected to column chromatography with a silica gel column (70-230 mesh, 60 Å) using a step gradient of hexane:dichloromethane (10:1, 5:1, 1:1). The recovered material was pure RRR-alpha-tocotrienol as determined by mass spectrometry, 1H- and $^{13}$C-NMR.

NaH (0.270 g of a 60% dispersion in mineral oil, 6.7 mmol) was suspended in dry THF (75 mL) under an argon atmosphere at 0° C. for 10 min, at which time alpha-tocotrienol (2.00 g, 4.71 mmol) dissolved in 25 mL of dry THF was added via cannula. This mixture was stirred at 0° C. for 15 min under argon, then ethyl bromoacetate (0.93 g, 5.59 mmol) was added via syringe. The reaction was monitored by TLC (hexane:ethyl acetate, 10:1, R$_f$=0.36) until it was judged complete after 3.5 hours. The reaction solution was diluted with 50 mL of CH$_2$Cl$_2$, washed with saturated NaCl solution (50 mL×3), dried over anhydrous Na$_2$SO$_4$ and the solvent removed under reduced pressure. The crude product was purified by column chromatography on silica gel (70-200 mesh) using hexane:ethyl acetate, 30:1) to yield 1.64 g (68%) of a clear oil.

The ester, ethyl 6-O-carboxymethyl-α-tocotrienol, (2.49 g, 4.87 mmol) was dissolved in 50 mL of dry THF, then 11.5 mL of 10% KOH was added and the mixture stirred at room temperature for 6 hrs. The reaction progress was monitored by TLC (CHCl$_3$:MeOH:CH$_3$CO$_2$H, 97:2.5:0.5, R$_f$=0.16). The resulting solution was adjusted to pH 3 using 1N HCl and the product extracted with CH$_2$Cl$_2$ (50 mL×3), washed with saturated NaCl solution, dried over anhydrous Na$_2$SO$_4$, and

EXAMPLE 4

Cell Culture Conditions

All test cell lines were cultured at 37° C. in 5% CO$_2$ in standard media supplemented with fetal calf serum, using established standard conditions. Plastic adherent cells were disassociated with trypsin, washed, counted, and used directly in experiments. All cells were examined routinely to verify no mycoplasma contamination.

EXAMPLE 5

Solubility and Dilution of Tocopherol and Tocotrienol Compounds

All compounds were handled as if they were light sensitive (photodegradable). All compounds were initially dissolved in absolute ethanol and subsequently diluted to a final concentration of 0.5% ethanol with the appropriate media.

EXAMPLE 6

Determination of Effective Concentration (EC$_{50}$) of Naturally Occurring Tocopherols and Tocotrienols Table 1 provides tumor growth inhibitory properties of naturally occurring vitamin E compounds against the breast tumor cell line MDA-MB-435. The naturally occurring α-, γ-, δ-tocotrienols exhibit tumor growth inhibitory properties with EC$_{50}$ of 40, 10, and 5 μM for DNA synthesis arrest, and 50, 10, and 5 μM for apoptosis, respectively. The naturally occurring α, γ, and δ tocopherols were relatively ineffective as anticancer agents, with EC$_{50}$ for DNA synthesis arrest of >400, >400, and 150 μM, respectively, and EC$_{50}$ for apoptosis of >400, 300, and 100 μM, respectively (Table 1).

TABLE 1

EC$_{50}$ for DNA Synthesis Arrest and
Apoptosis (μM) in MDA-MB-435

|   | DNA Synthesis Arrest | Apoptosis |
|---|---|---|
| Tocopherol | | |
| α | >400 | >400 |
| γ | >400 | 300 |
| δ | 150 | 100 |
| Tocotrienol | | |
| α | 40 | 50 |
| γ | 10 | 10 |
| δ | 5 | 5 |

EXAMPLE 7

Determination of Effective Concentration (EC$_{50}$) of Tocopherol Derivatives and Analogs to Induce Apoptosis Whereas the parental non-structurally modified forms of tocopherols do not exhibit effective apoptotic properties against a battery of tumor cells, fifteen out of twenty-nine RRR-α-tocopherol compounds and two out of five 1-aza-α-tocopherol analogs, structurally modified via ether linked moieties of different composition and size were extremely effective at inducing tumor cells to undergo apoptosis while having no apoptotic inducing properties on normal cells. Compounds 1, 2, 3, 7, 8, 9, 12, 15, 17, 19, 20, 21, 22, 25, 26, 27, 39, and 42 exhibit effective growth inhibitory (apoptotic inducing) properties specific for human cancer cells from a wide variety of cell lineages, including (i) breast (estrogen responsive Michigan Cancer Foundation human breast cancer cell line number 7, MCF-7 McGuire; non-estrogen responsive M.D. Anderson metastatic breast human cancer cell line, MDA-MB-435; and, estrogen non-responsive M.D. Anderson metastatic human breast cancer cell line, MDA-MB-231); (ii) prostate (androgen responsive human prostate cancer cell line, LnCaP and the androgen non-responsive human prostate cancer cell line, PC-3 and the DU-145 cell line); (iii) promyelocytic leukemia cells (human Promyelocytic Leukemia Cell Line, HL-60), lymphoid cell lines Jurkat and HL-60; (iv) cervical (human cervical cancer cell line, ME-180); (v) ovarian (human ovarian cancer cell line, C-170 cells); (vi) endometrial (human endometrial cancer cell line, RL-95-2 cells); (vii) colon cell lines DLD-1; and (viii) lung cell line A-549. Normal primary breast cells (normal primary early passage human mammary epithelial cells, HMEC) and immortalized, non-tumorigenic mammary cells (Michigan Cancer Foundation immortalized but non-tumorigenic human mammary number 10A cells, MCF-10A) do not undergo apoptosis when cultured with the above pharmacodynamically designed forms of tocopherol.

The apoptotic EC$_{50}$ for a battery of test cancer cells for the twenty-nine novel RRR-α-tocopherol compounds and two of the five 1-aza-α-tocopherol analogues of this invention are presented in Tables 2-1/2-2 and 3-1/3-2.

TABLE 2

| Cell Type | VES | 1 | 2 | 3 | 4 | 5 | 6 | 7 |
|---|---|---|---|---|---|---|---|---|
| Breast Cancer | | | | | | | | |
| HMEC | N | N | N | N | N | N | N | N |
| MCF-10A | N | N | N | N | N | N | N | N |
| MDA-MB-435 | 5-10 | 5-10 | 10-20 | 5-10 | N | N | N | 5-10 |
| MDA-MB-231 | 5-10 | 5-10 | 10-20 | 5-10 | N | N | N | 5-10 |
| MCF-7 | 10-20 | 5-10 | 20-30 | 20-30 | N | N | N | 10-20 |
| T47D | N | N | N | N | N | N | N | N |
| Cervical | | | | | | | | |
| ME-180 | 10-20 | 1-5 | 5-10 | 10-20 | N | N | N | 5-10 |
| Ovarian | | | | | | | | |
| C-170 | N | 10-20 | 10-20 | 10-20 | N | N | N | 10-20 |
| Endomerial | | | | | | | | |
| RL-95-2 | 10-20 | 10-20 | 10-209 | 10-20 | N | N | N | 5-10 |
| Prostate | | | | | | | | |
| PREC | N | N | NT | NT | NT | NT | NT | NT |
| LnCaP | 5-10 | 5-10 | 5-10 | 5-10 | N | N | N | 2.5-5 |
| PC-3 | 10-20 | 5-10 | 5-10 | 5-10 | N | N | N | 5-10 |
| DU-145 | 10-20 | 5-10 | NT | NT | NT | NT | NT | NT |
| Colon | | | | | | | | |
| HT-29 | 5-10 | 10-20 | NT | NT | NT | NT | NT | NT |
| DLD-1 | 10-20 | 10-20 | NT | NT | NT | NT | NT | NT |
| Lung | | | | | | | | |
| A-549 | 20-30 | 10-20 | NT | NT | NT | NT | NT | NT |
| Lymphoid Cells | | | | | | | | |
| Myeloma | 10-20 | NT | NT | NT | NT | NT | NT | NT |
| Raji | 10-20 | NT | NT | NT | NT | NT | NT | NT |
| Ramos | 10-20 | NT | NT | NT | NT | NT | NT | NT |
| Jurkat | 10-20 | 10-20 | NT | NT | NT | NT | NT | NT |
| HL-60 | 10-20 | 5-10 | 10-20 | 10-20 | N | N | N | 5-10 |
| Cell Type | 8 | 9 | 10 | 11 | 12 | 13 | 14 | 15 |
| Breast Cancer | | | | | | | | |
| HMEC | N | N | N | N | N | N | N | NT |
| MCF-10A | N | N | N | N | N | N | N | NT |
| MDA-MB-435 | 5-10 | 5-10 | N | N | 5-10 | N | N | 20-30 |
| MDA-MB-231 | 5-10 | 5-10 | N | N | 5-10 | N | N | 20-30 |
| MCF-7 | 10-20 | 10-20 | N | N | 5-10 | N | N | 20-30 |
| T47D | NT | NT | NT | NT | NT | NT | NT | NT |
| Cervical | | | | | | | | |
| ME-180 | 5-10 | 5-10 | N | N | 5-10 | N | N | N |
| Ovarian | | | | | | | | |
| C-170 | 10-20 | N | N | N | 10-20 | N | N | N |
| Endomerial | | | | | | | | |
| RL-95-2 | 1-5 | 5-10 | N | N | 5-10 | N | N | N |
| Prostate | | | | | | | | |
| PREC | NT | NT | NT | NT | NT | NT | NT | NT |
| LnCaP | 5-10 | 5-10 | N | N | >20-30 | NT | N | NT |
| PC-3 | 5-10 | 5-10 | NT | N | 10-20 | N | N | NT |
| DU-145 | NT | NT | NT | NT | NT | NT | NT | NT |
| Colon | | | | | | | | |
| HT-29 | NT | NT | NT | NT | NT | NT | NT | NT |
| DLD-1 | NT | NT | NT | NT | NT | NT | NT | NT |
| Lung | | | | | | | | |
| A-549 | NT | NT | NT | NT | NT | NT | NT | NT |
| Lymphoid Cells | | | | | | | | |
| Myeloma | NT | NT | NT | NT | NT | NT | NT | NT |
| Raji | NT | NT | NT | NT | NT | NT | NT | NT |
| Ramos | NT | NT | NT | NT | NT | NT | NT | NT |
| Jurkat | NT | NT | NT | NT | NT | NT | NT | NT |
| HL-60 | 10-20 | 10-20 | N | N | 20-30 | N | N | NT |

TABLE 3

| Cell Type | 16 | 17 | 18 | 19 | 20 | 21 | 22 | 23 |
|---|---|---|---|---|---|---|---|---|
| Breast Cancer | | | | | | | | |
| HMEC | NT | NT | NT | NT | NT | NT | NT | NT |
| MCF-10A | NT | N | NT | N | N | N | NT | N |
| MDA-MB-435 | N | NT | N | 10-20 | 10-20 | N | NT | N |
| MDA-MB-231 | N | NT | NT | NT | NT | NT | NT | NT |
| MCF-7 | N | 10-20 | N | 10-20 | 5-10 | N | 15-20 | N |
| T47D | NT | 10-20 | NT | N | 5-10 | NT | NT | NT |
| Cervical | | | | | | | | |
| ME-180 | NT | 20-30 | N | 1-5 | 1-5 | 1-5 | NT | NT |
| Ovarian | | | | | | | | |
| C-170 | NT | 20-30 | N | 1-5 | * | N | NT | NT |
| Endomerial | | | | | | | | |
| RL-95-2 | NT | NT | NT | NT | NT | N | NT | NT |
| Prostate | | | | | | | | |
| PREC | NT | NT | N | NT | NT | NT | NT | NT |
| LnCaP | NT | 10-20 | NT | 5-10 | 5-10* | N | NT | NT |
| PC-3 | NT | NT | NT | N | 5-10* | N | NT | N |
| DU-145 | NT | NT | NT | 5-10 | 5-10* | N | NT | N |
| Colon | | | | | | | | |
| HT-29 | NT | N | N | NT | NT | NT | NT | N |
| DLD-1 | NT | NT | NT | NT | NT | NT | NT | NT |
| Lung | | | | | | | | |
| A-549 | NT | N | N | 20-30 | 20-30 | NT | NT | NT |
| Lymphoid Cells | | | | | | | | |
| Myeloma | NT | NT | NT | NT | NT | NT | NT | NT |
| Raji | NT | NT | NT | NT | NT | NT | NT | NT |
| Ramos | NT | NT | NT | NT | NT | NT | NT | NT |
| Jurkat | NT | 10-20 | N | 10-20 | 10-20 | NT | NT | NT |
| HL-60 | NT | 10-20 | N | 10-20 | 10 | NT | NT | NT |

| Cell Type | 24 | 25 | 26 | 27 | 28 | 29 | 39 | 42 | 43 |
|---|---|---|---|---|---|---|---|---|---|
| Breast Cancer | | | | | | | | | |
| HMEC | NT | NT | NT | NT | NT | NT | NT | NT | NT |
| MCF-10A | NT | N | N | NT | NT | NT | NT | NT | NT |
| MDA-MB-435 | N | N | 20-40 | NT | NT | NT | 10-20 | 10-20 | PPT |
| MDA-MB-231 | NT | NT | NT | NT | NT | NT | NT | NT | NT |
| MCF-7 | N | N | N | 10-20 | NT | NT | NT | NT | NT |
| T47D | NT | NT | N | NT | NT | NT | NT | NT | NT |
| Cervical | | | | | | | | | |
| ME-180 | NT | N | * | NT | NT | NT | NT | NT | NT |
| Ovarian | | | | | | | | | |
| C-170 | NT | N | 20-30 | NT | NT | NT | NT | NT | NT |
| Endomerial | | | | | | | | | |
| RL-95-2 | NT | N | 20-30 | NT | NT | NT | NT | NT | NT |
| Prostate | | | | | | | | | |
| PREC | NT | NT | NT | NT | NT | NT | NT | NT | NT |
| LnCaP | N | N | 10-20 | 10-20 | NT | NT | NT | NT | NT |
| PC-3 | N | 20-30 | N | NT | NT | NT | NT | NT | NT |
| DU-145 | N | 20-30 | N | NT | NT | NT | NT | NT | NT |
| Colon | | | | | | | | | |
| HT-29 | NT | N | N | NT | NT | NT | NT | NT | NT |
| DLD-1 | N | N | 20-40 | NT | NT | NT | NT | NT | NT |
| Lung | | | | | | | | | |
| A-549 | NT | NT | N | NT | NT | NT | NT | NT | NT |
| Lymphoid Cells | | | | | | | | | |
| Myeloma | NT | NT | NT | NT | NT | NT | NT | NT | NT |

TABLE 3-continued

| Raji | NT | NT | NT | NT | NT | NT | NT | NT | NT |
|---|---|---|---|---|---|---|---|---|---|
| Ramos | NT | NT | NT | NT | NT | NT | NT | NT | NT |
| Jurkat | NT | NT | 20-30 | NT | NT | NT | NT | NT | NT |
| HL-60 | NT | NT | N | NT | NT | NT | NT | NT | NT |

EXAMPLE 8

Determination of Effective Concentration ($EC_{50}$) of 6-O-Carboxymethyl Alpha-Tocotrienol MDA-MB-435 and MCF-7 cells at $1.5 \times 10^5$/well in 12 well plates for apoptosis and $1.5 \times 10^4$/well in 96 well plates for DNA synthesis arrest were incubated overnight in culture media and treated with α-tocopherol, α-tocotrinel, compound 1,6-O-carboxymethyl alpha-tocotrienol (6-0-CM-α-T, 44), and vitamin E succinate (VES) at different concentrations in experimental media (2% serum for MDA-MB-435 cells and 5% serum for MCF-7 cells). DNA synthesis arrest was determined by $^3$H-uptake at one day treatment and apoptosis was detected by DAPI staining at three day treatment. $EC_{50}$ was calculated as the dosage of test compounds that gave 50% growth inhibition.

The compound, 6-0-carboxymethyl alpha-tocotrienol 44, has superior anti-tumor properties when compared to those of naturally occurring tocopherols and tocotrienols as well as vitamin E succinate or ether linked succinated tocopherol-based compounds. Comparison of DNA synthesis arrest properties and apoptotic inducing properties of RRR-α-tocopherol, alpha-tocotrienol, compound 1, and 6-0-carboxymethyl alpha-tocotrienol (6-0-CM-α-Toc, 44) are shown in Tables 4 and 5, respectively.

TABLE 4

$EC_{50}$ for DNA Synthesis Arrest (μM)

| | Tumor Cell Lines | |
|---|---|---|
| Compounds | MDA-MB-435 | MCF-7 |
| α-tocopherol | >100 | >100 |
| α-tocotrienol | 29 | 40 |
| Cmpd. 1 | 15 | 20 |
| 6-0 CM-α-Toc (44) | 2.5 | 5 |
| VES | 17 | 22 |

TABLE 5

$EC_{50}$ for Apoptosis (μM)

| | Tumor Cell Lines | |
|---|---|---|
| Compounds | MDA-MB-435 | MCF-7 |
| α-tocopherol | >100 | >100 |
| α-tocotrienol | 66 | 40 |
| Cmpd. 1 | 30 | 36 |
| 6-0-CM-α-Toc (44) | 5.6 | 10 |
| VES | 36 | 40 |

The pharmacodynamically designed 6-0-carboxymethyl alpha-tocotrienol 44 has an improved therapeutic index and is a potent inhibitor of cancer cell growth; i.e., 6-0-carboxy methyl alpha-tocotrienol 44 exhibits antitumor activity, as measured by DNA synthesis arrest, toward human MDA-MB-435 and MCF-7 breast cancer cells 8-12 fold higher than the parent material, alpha-tocotrienol, 4-7 fold higher than vitamin E succinate, and 4-6 fold higher than compound 1. Also, 6-0-carboxymethyl alpha-tocotrienol 44 is a potent apoptotic inducer when tested using human MDA-MB-435 and MCF-7 breast cancer cells. 6-0-carboxymethyl alpha-tocotrienol 44 induction of apoptosis for the two cell types was 4-12 fold higher than alpha tocotrienol, 4-6 fold higher than vitamin E succinate and 4-5 fold higher than compound 1.

EXAMPLE 9

Bioassay for Apoptosis

Cells were cultured at $1.5 \times 10^5$ cells/well in 12 well plates. Cells were allowed to adhere overnight, then incubated with novel test compounds at 0.01, 0.1, 1, 5, 10 & 20 μg/mL for 1, 2 and 3 days. After treatment, cells (floating+trypsin released adherent cells) were pelleted, washed and stained with 2 μg/ml DAPI (4',6-diamidine-2'-phenylindole dihydrochloride) in 100% methanol for 15 minutes at 37° C. and/or 3'-OH ends resulting from DNA fragmentation were detected with the TUNEL (terminal deoxynucleotidyl transferase-mediated dUTP-X 3' nick end-labeling) technique, and then viewed using a Zeiss ICM 405 microscope. Cells whose nucleus contained clearly condensed or fragmented chromatin or stained for fragmented DNA in the TUNEL assay were scored as apoptotic. Data are presented as percent cells undergoing apoptosis.

EXAMPLE 10

Bioassay for DNA Synthesis Arrest

To assay DNA synthesis, all cells were used at $2.5 \times 10^5$/ml. Cells were treated with each of the compounds at concentrations of 0.01, 0.1, 1, 5, 10 and 20 μg/mL and 200 μl of each treatment group were plated in quadruplicate in a 96 well culture plate (Corning, Corning N.Y.). Experiments were done in duplicate, one plate used for viability testing and the other plate for examination of $^3$H-TdR uptake to monitor DNA synthesis. Plates were cultured for 48 hours at 37° C., 5% $CO_2$. Eight hours prior to the end of incubation, $^3$H-TdR was added to one of the duplicate plates and incubation continued for 8 hours. The cells were then harvested (trypsinization was required to harvest adherent cells), and isotope uptake was determined as counts per minute (cpm). For viability studies, at the end of the incubation, the cells were removed from the wells and viability checked by the Trypan Blue Exclusion method. Percent viability and percent DNA synthesis in comparison to untreated or vehicle treated cells of each treatment group were calculated.

EXAMPLE 11

Bioassay for Cell Cycle Arrest

The cells were cultured with novel test agents for 2-3 days, fixed in 95% ethanol and stained with propidium iodide overnight. DNA content was determined using a Coulter Epics Elite Flow Cytometer with an argon laser setting of 488 nm.

Cell size was measured simultaneously, and data were analyzed as to percent cells in each cell cycle phase using the Coulter Multicycle Program.

EXAMPLE 12

Bioassay for Cellular Differentiation

To determine if the novel compounds were inducing cellular morphological features of differentiation, the cells were cultured on cover slips, then unstained cells were examined for cell shape and nuclear versus cytoplasmic volumes. Cells were also fixed with 4% paraformaldehyde and stained with Oil Red O for detection of milk lipids. Additionally, cells were examined by Western immunoblot analyses for presence of various biomarkers of differentiation including: Her-2/neu, p21 Waf2/Cip1, and cytokeratin 18, and examined by RT-PCR for presence of β-casein mRNA.

EXAMPLE 13

Mechanisms of Induction of Apoptosis

Without being limited by theory, the mechanism of induction of apoptosis by these compounds appears to involve three distinct apoptotic signaling pathways; namely, activation of latent transforming growth factor-beta (TGF-β), activation of the Fas/Fas ligand signaling pathways, and signaling by the stress kinase (c-Jun N-terminal Kinase) pathway.

TGF-βs are potent growth inhibitory molecules that are known to inhibit cell growth by inhibition of DNA synthesis arrest and by induction of apoptosis. TGF-βs are involved only in induction of the apoptotic pathway, i.e., there is no evidence currently that the TGF-βs effect DNA synthesis arrest; however, this possibility has not been completely ruled out. TGF-βs are made and secreted by cells in a latent non-active form. To be effective as tumor growth inhibitors, the latent TGF-βs must be activated by induction of cell surface proteins that provide a proper structure for processing and activating proteases that cut the latent protein and release the active TGF-β.

The compounds of the present invention are shown to activate proteases such as cathepsin D family proteases, and upregulate the mannose-6-phosphate receptor which binds inactive TGF-β and permits activation via proteases. Active TGF-β signals via cell membrane TGF-β receptors I and II to activate down stream kinases referred to as stress kinases or c-Jun N-terminal Kinases (JNK) which phosphorylate and activate transcription factors c-Jun, ATF-2 and Elk-1. Prolonged activation of transcription factor c-Jun causes tumor cells to undergo apoptosis. These transcription factors, acting as homodimers or heterodimers with a multitude of transcription factor partners activate proapoptotic genes and/or downregulate antiapoptotic genes leading to DNA fragmentation. The compounds of the present invention do not generate an anti-proliferative outcome to TGF-β signaling in normal non-tumor cells.

A second apoptotic inducing mechanism called the Fas/Fas ligand apoptotic signaling pathway is activated by the novel compounds of the present invention. Activated Fas/Fas ligand signaling may lead to rapid cell death by apoptosis. Thus, for tumor cells to escape death by Fas/Fas ligand, they must inactivate this most important apoptotic pathway. The mechanism for inactivation of the Fas/Fas ligand signaling pathway by tumor cells varies; however, many tumor cells down regulate the expression of Fas receptor and Fas ligand on their membranes.

Most important, R,R,R-2-(2,5,7,8-tetramethyl-2-(4,8,12-trimethyltridecyl)chroman-6-yloxy)acetic acid (1) has been shown to induce Fas/Fas ligand resistant tumor cells to become Fas/Fas ligand sensitive. Compound 1 also has the ability to enhance the expression of Fas ligand on the membrane of LNCaP prostate cells. Studies show that Fas signaling resistant human breast cancer cells retain the Fas receptor in their cytoplasm, but when cultured with compound 1, the Fas receptor is transported from the cytoplasm to the membrane; thereby rendering the cells Fas signaling sensitive. Furthermore, this compound is synergistic in anti-Fas triggered apoptosis in that greater amounts of cell killing is obtained with both human breast and prostate cancer cells when co-treated versus when treated separately. The ability of compound 1 to convert Fas signaling resistant tumor cells to Fas signaling sensitive tumor cells and to exhibit synergistic killing effects provides an extremely important mechanism for destruction of tumor cells both by the host immune surveillance system as well as by pharmaceutical intervention. The compounds of the present invention do not activate the Fas signaling pathway of normal non-tumor cells.

These compounds activate the JNK kinase signaling pathway, perhaps by TGF-β and Fas/Fas ligand signaling. Prolonged activation of JNK results in prolonged activation of c-Jun and ATF-2 transcription factors, which are postulated to play a role in expression or repression of proapoptotic and antiapoptotic genes, respectively.

EXAMPLE 14

Mechanism of Induction of DNA Synthesis Arrest, Cell Cycle Arrest and Cellular Differentiation The mechanisms of growth inhibition by DNA synthesis arrest, cell cycle arrest and by induction of cellular differentiation have not been characterized as fully as the mechanism of growth inhibition by apoptosis. Studies show that the compounds of the present invention have profound effects on the cell cycle, inducing DNA synthesis arrest of approximately 95% of the tumor cells within 24 hours of treatment. Tumor cells cultured with the compounds disclosed herein are growth inhibited in the G1 cell cycle phase, undergo morphological changes and express milk lipids, an indication that the cell cycle blocked cells have undergone differentiation. P21, a gene known to be an inhibitor of entrance of cells from the G1 cell cycle phase to the S phase of the cell cycle, and the mRNA, as well as the protein of P21 gene, is up-regulated by treatment of MDA-MB-435 human breast cancer cells with compound 1.

EXAMPLE 15

In Vivo Potential for Human Cancer Cells

The present invention has potential for use as therapeutic agents. In vivo studies of tumor growth and metastasis of human tumor cells either ectopically or orthotopically transplanted into immune compromised animals, such as nude mice, or in vivo studies employing well recognized animal models are conducted. Inhibition of growth of human tumor cells transplanted into immune compromised mice, provide pre-clinical data for clinical trials. In vivo studies include two human tumor cell models, the metastatic non-estrogen responsive MDA-MB-435 breast cancer model, the androgen non-responsive PC-3 prostate cancer model and a murine syngeneic 66c1.4-GFP mammary cancer model.

MDA-MB-435 Breast Cancer Model:

Pathogen free MDA-MB-435 human breast cancer cells stably transfected with a marker protein (fluorescent green protein) are grown as a solid tumor in immune compromised nude or SCID mice. $1\times10^6$ tumor cells are orthotopically injected into the mammary fat pad or ectopically injected near the 4th and 5th nipples of female nude mice. Tumor growth, metastasis, and death of the animals are determined. Tumor growth is measured by caliper evaluations of tumor size. At the time of sacrifice, tumors are removed, measured for size, and used for histochemical examination. Organs such as spleen, lymph nodes, lungs, and bone marrow, are examined for metastatic MDA-MB-435 cells by histochemical staining of tissue sections for expression of the marker fluorescent green protein.

PC-3 Prostate Cancer Model

Pathogen free PC-3 human prostate cancer cells stably transfected with a marker protein (fluorescent green protein) are grown as a solid tumor in nude mice. The tumors are removed, and 1 mm sections of equal size are ectopically transplanted into the hind flank of male nude mice. Tumor growth, metastasis, and death of the animals are determined. At the time of sacrifice, tumors are removed, measured for size, and used for histochemical examination. Organs such as spleen, lymph nodes, lungs, bone marrow, are examined for metastatic PC-3 cells by histochemical staining of tissues for expression of the marker fluorescent green protein.

Murine Syngeneic 66c1.4-GFP Mammary Cancer Model.

Pathogen free 66c1.4-GFP mammary cancer cells of Balb/c origin (100,000 to 200,000) are injected near the 4th and 5th nipples of female Balb/c mice. Tumor metastases to lungs occur in 100% of the mice. Tumor growth, metastasis, and death of the animals are determined. Tumor growth is measured by caliper evaluations of tumor size. At the time of sacrifice, tumors are removed, measured for volume, and used for histochemical examination. Organs such a s spleen, lymph nodes, lungs, and bone marrow, are examined for metastatic cells by histochemical staining of tissue sections for expression of the marker green fluorescence protein.

Skin Cancer Animal Model

Skin cancer is induced in SENCAR and SKH-1 hairless mice by ultraviolet irradiation and chemical (DMBA) treatments. In addition, mice specifically expressing the oncogene Her-2/neu in skin basal cells that spontaneously develop skin cancer are used. The compounds disclosed herein are topically applied to the skin daily, before and after skin cancer initiation, and development of skin papilloma formation is assessed. Control mice are treated identically except that they receive vehicle treatments topically applied to their skin. The efficacy of these compounds in treating papilloma's as well as their ability to affect malignant conversion when supplied prior to premalignant progression is monitored.

EXAMPLE 16

Supplementation with Novel Compounds

Prior to initiation of the in vivo experiments, the compounds of this invention that exhibit the greatest amount of tumor cell killing are administered to nude, SCID, transgene, and other mice at varying levels to establish the highest level of compound that can be administered safely without adverse effects. The compounds are administered in a model-appropriate manner; e.g., liposomal/aerosol/nasal/lungs, orally, injections, including injections directly into the target organ, or topically. After establishing the highest level of the compounds that can be tolerated and effective administration routes, the novel compounds are administered to the mice on a daily basis, and tumor growth and progression is determined as described above.

EXAMPLE 17

Establishing Maximum Tolerated Dose (MTD) of 2,5,7,8-tetramethyl-(2R-(4R,8R,12-trimethyltridecyl) chroman-6-yloxy)acetic acid (1)

Figure 7:
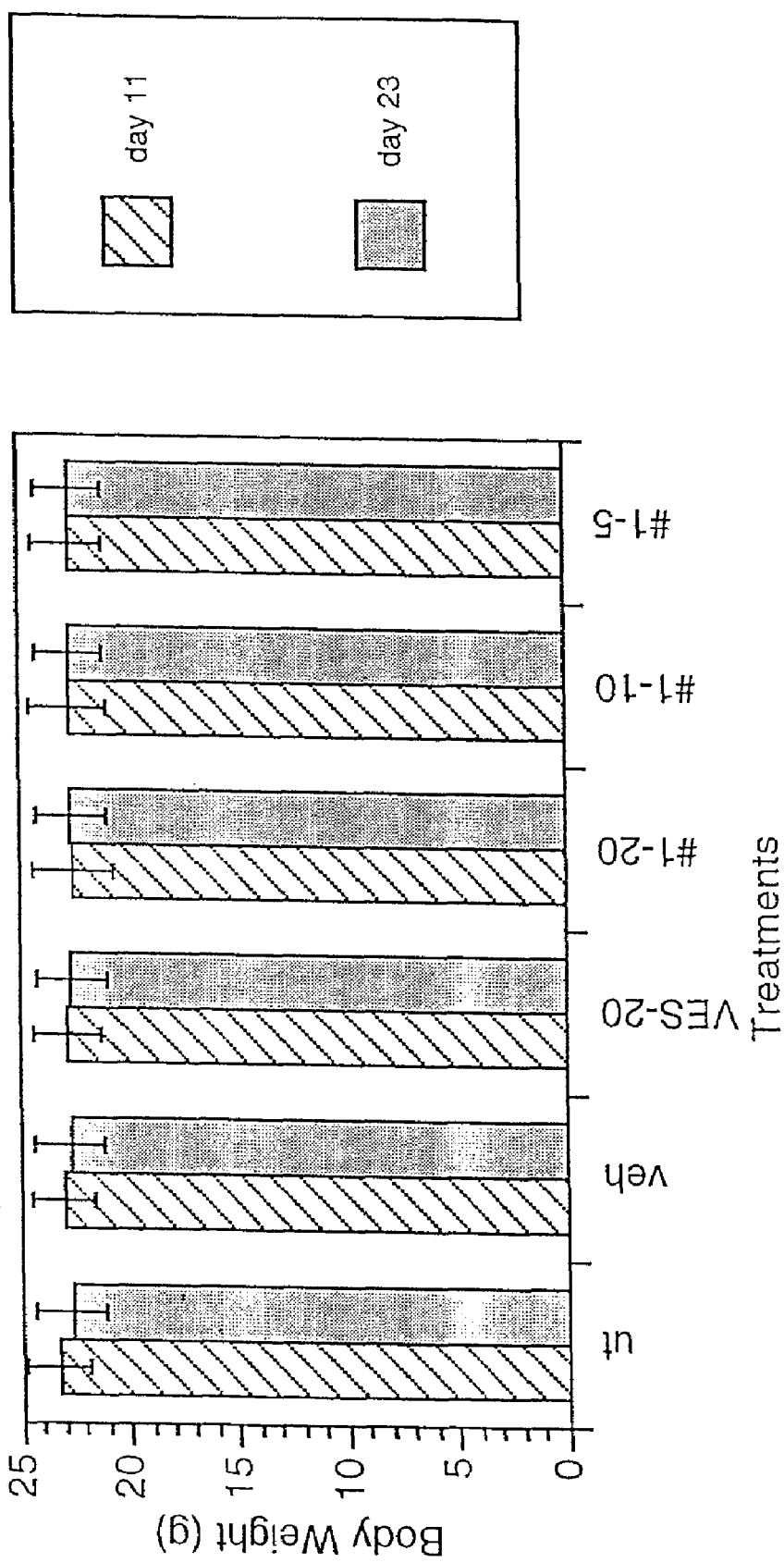
FIG. 7 shows the mean body weights of non-tumor Balb/c female mice at day 11 and day 23 of a maximum tolerated dose study.

Prior to conducting the preclinical chemotherapeutic studies, compound 1 is assayed in non-tumor Balb/c female mice in an effort to establish the maximum tolerated dose. Compound 1 is dissolved in 100% ethanol to establish a stock solution (2 grams of compound 1 in 5 mls of 100% ethanol) and diluted in peanut oil (non vitamin E supplemented) to yield 20, 10, and 5 mg/0.1 ml. RRR-$\alpha$-tocopherol succinate (VES; the succinate moiety is attached to RRR-$\alpha$-tocopherol via an ester linkage) was solubilized and diluted as described above to yield 20 mg/0.1 ml/gavage, serving as an additional control. A total of 30 Balb/c female mice were placed into 6 groups (5 mice/group) and supplemented by gavage with compound 1 daily for a total of 23 days. Group 1 mice were non treated and served as control; group 2 mice were the vehicle control group and received 0.1 ml of vehicle (ethanol+peanut oil equivalent to treatment groups)/mouse/day for a total of 23 days, group 3 mice received 20 mg/ml of VES daily for a total of 23 days. Treatment groups 3, 4 and 5 were gavaged daily for 23 days with 5, 10, and 20 mgs of compound 1. Compound 1 at 5, 10, and 20 mg/day, administered daily by gavage to mice in groups 3, 4, and 5, respectively, for 23 days is tolerated well by the mice. Weights are determined weekly and there is no significant difference in the weights of the mice receiving compound 1 at 5, 10, and 20 mg/day when compared with the weights of the VES treated, untreated and vehicle treated control mice (FIG. 7, data is for days 11 and 23 days treatment). Mice remained active and showed no signs of toxicity. At the completion of the MTD studies, mice were sacrificed and no evidence of toxicity was observed upon autopsy.

EXAMPLE 18

Chemotherapeutic effectiveness of 2,5,7,8-tetramethyl-(2R-(4R,8R,12-trimethyltridecyl)chroman-6-yloxy)acetic acid (1)

The maximum tolerated dose studies show that compound 1 administered at the highest level (20 mg/day/23 days) is not toxic; however, due to the non-toxic levels used, an maximum tolerated dose was not established. For the preclinical chemotherapeutic studies, in the absence of an maximum tolerated dose, the mice are supplemented with 30 and 20 mgs/0.1 ml by gavage daily for 21 days. Compound 1 is dissolved in 100% ethanol at 2 grams of compound ⅕ mls of ethanol, and diluted in peanut oil (nonsupplemented vitamin E) to yield 30 and 20 mgs of compound 1 per 0.1 ml. Vehicle control consisted of a mixture of ethanol and peanut oil equivalents. The preclinical chemotherapeutic studies are conducted with compound 1, utilizing human MDA-MB-435 human breast cancer cells, human DU-145 prostate cancer cells, and human HT-20 colon tumor cells transplanted into Balb/c immune compromised nude mice.

A total of 40 immune compromised nude mice are utilized for testing each test compound (two treatment groups at 20 and 30 mg/day) in each tumor cell type. Four experimental treatment groups of 10 mice each (vehicle/0.1 ml/gavage daily for 21 days, compound 1 at 30 mgs of compound #1/0.1 ml gavage/daily for 21 days, and compound 1 at 20 mgs/of compound 1/0.1 ml gavage daily for 21 days, for each tumor type are used. An established dosage of effective chemotherapeutic drugs is used in the xenograft studies. Taxol at 20/mg/kg, administered intraperitioneally daily for 5 days, is used for a positive control for human MDA-MB-435 breast cancer xenografts; Mitoxantrone at 1 mg/kg, administered daily intravenously for 5 days, is used as the positive control for human DU-145 prostate cancer cells; and 5 Fluorouracil (5 FU) at 30 mg/kg, administered daily for 5 days, is used for a positive control for human HT-29 colon cancer cells. Tumor cells are transplanted subcutaneously into the left flank and permitted to grow to approximately 70 mg in size, test compound treatments by daily gavage are initiated, and continue for a total of 21 days. Mice are monitored daily for tumor size by caliper measurements. Mice are treated for 21 days; however, the mice are sacrificed when the tumors of the vehicle control reached 500 mg in weight. At the completion of the protocol, tumors are excised and tumor size established by weight. At the time of sacrifice, serum, tumor, and heart muscle are taken from animals in the two compound 1 test groups in order to establish levels of compound 1 via HPLC analyses (data not included). The chemotherapeutic effectiveness of compound 1 administered daily at 30 and 20 mgs/day is determined by comparing the tumor size of the two treatment groups with the vehicle control group for each of the three tumor types, and by comparing the size of the tumor in the two treatment groups with the tumor group from the positive control. Treatment is for 21 days, experiments are continued until mean weight of tumor for vehicle control reaches 500 mgs.

Figure 8A:
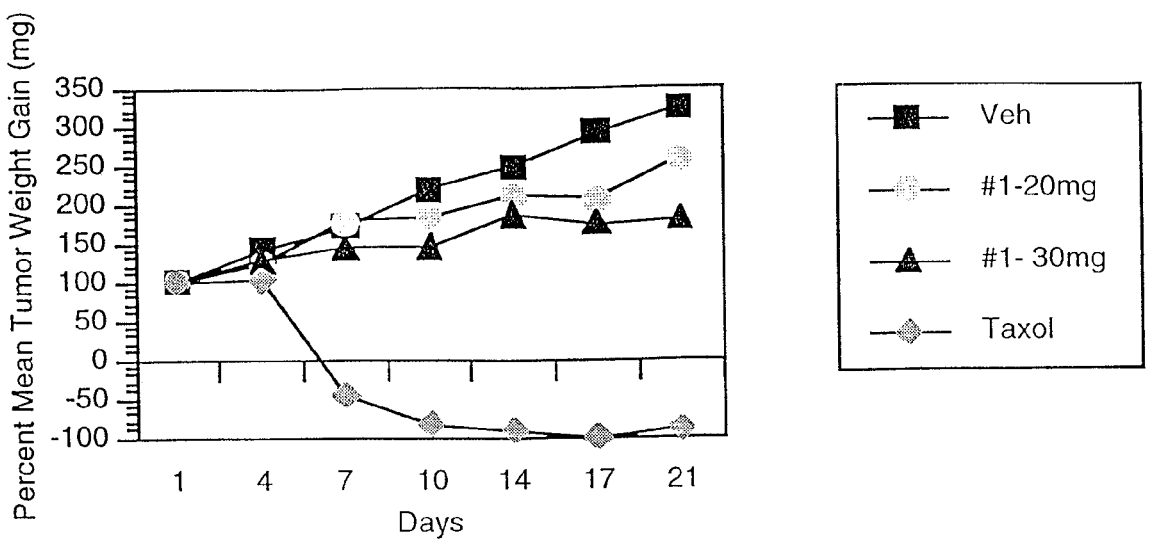
FIGS. 8A-8C shows the comparison of percent mean tumor weight following treatments in MDA MB-435 Human Breast Cancer Cells (FIG. 8A), DU-145 Human Prostate Cancer Cells (FIG. 8B) and HT-29 Human Colon Cancer Cells (FIG. 8C).
Figure 8B:
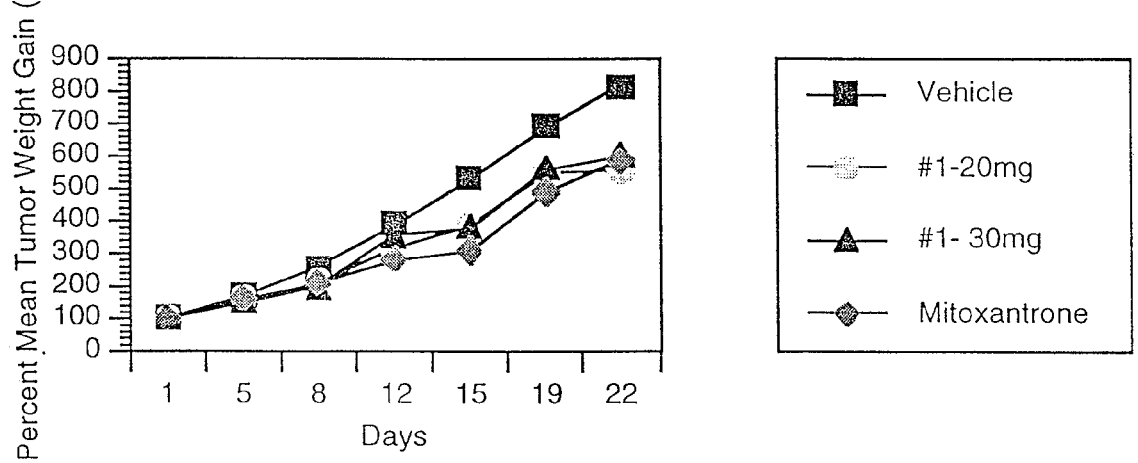
Figure 8C:
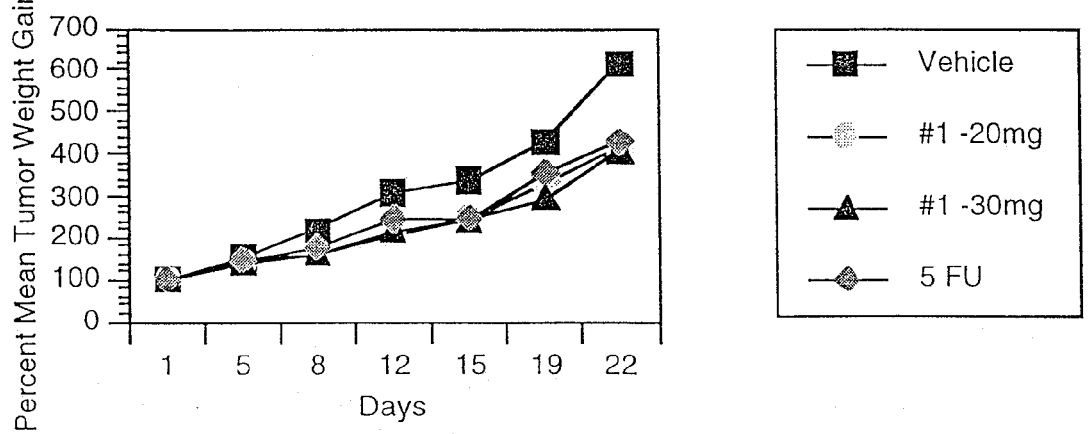

The in vivo preclinical chemotherapeutic data are depicted in Tables 3 and 4 and FIG. 8A-8C and are presented for 21-22 days of treatment. Treatment of nude mice transplanted with human MDA-MB-435 breast cancer cells with compound 1 for 21 days at 20 and 30 mg/day by gavage reduced the mean tumor weight (mg) of the transplanted tumor cells by 20.7 and 44.6%, respectively when compared to the mean tumor weight of the vehicle control group at day 21 after treatment. The positive control, Taxol, reduces the mean tumor growth, when compared to mean tumor growth of vehicle control group, by 90.3% (Table 6, 7 & FIG. 8A). Data are converted to percent mean tumor growth in relation to weight gain at the beginning of treatment (day 1) and are depicted in Table 7. Treatment of nude mice transplanted with human DU-145 prostate cancer cells with compound 1 for 21 days at 20 and 30 mg/day by gavage reduces the mean tumor weight (mg) of the transplanted tumor cells by 31.5 and 24.8%, respectively, when compared to the mean tumor weight of the vehicle control group at day 22 (Table 6, 7 & FIG. 8B). The positive control, mitoxantrone reduces the mean tumor growth, when compared to mean tumor growth of vehicle control group, by 27.9%. Treatment of immune compromised nude mice transplanted with human HT-29 human colon cancer cells with compound 1 for 21 days at 20 and 30 mg/day by gavage reduces the mean tumor weight (mg) of the transplanted tumor cells by 33.3 and 34.5%, respectively when compared to the mean tumor weight of the vehicle control group at day 22 (Table 6, 7 & FIG. 8C). The positive control, 5 Fluorouracil, reduces the mean tumor growth, when compared to mean tumor growth of vehicle control group, by 31.4%.

TABLE 6

MDA-MB-435 Human Breast Cancer Cells Transplanted into Nude Mice

| Treatments | Mean tumor Weights (mg) Following Treatments | | | | | | |
|---|---|---|---|---|---|---|---|
| | 1 | 4 | 7 | 10 | 14 | 17 | 21 |
| Vehicle | 70.1 | 98.2 | 119.5 | 153.2 | 172.8 | 203.7 | 226.1 |
| #1 (20 mg) | 70.1 | 85.8 | 123.9 | 127.9 | 147.2 | 143.8 | 179.4 |
| #1 (30 mg) | 68.1 | 85.7 | 97.3 | 98.4 | 126.6 | 118.7 | 125.2 |
| Taxol | 70.7 | 71.5 | 38.2 | 11.7 | 5.7 | 3.6 | 6.8 |

DU-145 Human Prostate Cancer Cells Transplanted into Nude Mice

| Treatments | Mean tumor Weights (mg) Following Treatments | | | | | | |
|---|---|---|---|---|---|---|---|
| | 1 | 5 | 8 | 12 | 15 | 19 | 22 |
| Vehicle | 66.5 | 111.4 | 167.1 | 258.5 | 351.1 | 458.3 | 540.9 |
| #1 (20 mg) | 66.5 | 103.5 | 137.9 | 208 | 254.8 | 362.2 | 370.5 |
| #1 (30 mg) | 67.8 | 102.5 | 131.3 | 241.2 | 256.8 | 379.9 | 407 |
| Mitoxantrone | 66.8 | 107.2 | 141.1 | 185.4 | 205.2 | 325.3 | 389.4 |

HT-29 Human Colon Cancer Cells Transplanted into Nude Mice

| Treatments | Mean tumor Weights (mg) Following Treatments | | | | | | |
|---|---|---|---|---|---|---|---|
| | 1 | 5 | 8 | 12 | 15 | 19 | 22 |
| Vehicle | 80.3 | 91.7 | 133.2 | 185.6 | 204.8 | 260.1 | 372.2 |
| #1 (20 mg) | 59.5 | 84.0 | 97.0 | 124.6 | 147.3 | 198.0 | 248.2 |
| #1 (30 mg) | 40.0 | 83.0 | 96.7 | 129.3 | 144.1 | 176.1 | 243.8 |
| 5-FU | 59.3 | 87.5 | 105.8 | 145.8 | 141.6 | 212.3 | 255.5 |

TABLE 7

Percent mean tumor weight gain (mg) following treatments[1]

MDA-MB-435 Human Breast Cancer Cells

| Treatments | 1 | 4 | 7 | 10 | 14 | 17 | 21 |
|---|---|---|---|---|---|---|---|
| Vehicle | 100 | 140.1 | 170.5 | 218.5 | 246.5 | 290.6 | 322.5 |
| #1 (20 mg) | 100 | 122.4 | 176.7 | 182.5 | 210.0 | 205.1 | 255.9 |
| #1 (30 mg) | 100 | 125.8 | 142.9 | 144.5 | 185.9 | 174.3 | 178.6 |
| Taxol | 100 | 101.1 | −46.0 | −83.7 | −91.8 | −99.5 | −90.3 |

DU-145 Human Prostate Cancer Cells

| Treatments | 1 | 5 | 8 | 12 | 15 | 19 | 22 |
|---|---|---|---|---|---|---|---|
| Vehicle | 100 | 167.5 | 251.3 | 388.7 | 528.0 | 458.3 | 689.2 |
| #1 (20 mg) | 100 | 155.6 | 207.4 | 312.8 | 383.2 | 362.2 | 544.7 |
| #1 (30 mg) | 100 | 151.2 | 193.7 | 355.8 | 378.8 | 379.9 | 560.3 |
| Mitoxantrone | 100 | 160.5 | 211.2 | 277.5 | 307.2 | 487.0 | 582.9 |

HT-29 Human Colon Cancer Cells

| Treatments | 1 | 5 | 8 | 12 | 15 | 19 | 22 |
|---|---|---|---|---|---|---|---|
| Vehicle | 100 | 152.1 | 220.9 | 307.8 | 339.6 | 431.3 | 617.2 |
| #1 (20 mg) | 100 | 141.2 | 163.0 | 209.4 | 247.6 | 332.8 | 417.1 |
| #1 (30 mg) | 100 | 139.5 | 162.5 | 217.3 | 242.2 | 296.0 | 409.7 |
| 5-FU | 100 | 147.6 | 178.4 | 245.9 | 247.2 | 358.0 | 430.0 |

[1]Percent Mean Tumor Weight Gain (mg) following treatment was determined by dividing the mean tumor weight at various time periods following treatment by the mean tumor weight at day 1 within the same treatment group and multiplying by 100.

EXAMPLE 19

Preparation of Stock Solution, Vehicle and 2,5,7,9-tetramethyl-(2R-(4R,8R,12-trimethyltridecyl)chroman-6-yloxy)acetic acid (1) Dilutions Compound 1 was prepared weekly, and stored at 4° C. The preparation procedures are as follows:

Stock Solution of Compound 1:

Dissolve 2 grams of compound 1 in 5 mls of 100% ethanol (ETOH) and vortex at 37° C. This is the maximum amount of compound 1 that will go into solution.

For the following dilutions, dry compound 1 is added to yield the appropriate levels of compound 1 while keeping the ethanol levels equal in the two experimental groups and the vehicle control group.

Compound 1 at 30 mg/0.1 ml gavage/mouse:

Combine 1 ml of compound 1 stock solution, 3 mls of vitamin E depleted peanut oil and 800 mg of compound #1 (dry) and vortex at 37° C.

Compound 1 at 20 mg/0.1 ml Gavage/Mouse:

Combine 1 ml of compound 1 stock solution, 3 mls of vitamin E depleted peanut oil and 400 mg of compound #1 (dry) and vortex at 37° C. approximate 2 h until in solution.

Compound 1 at 10 mg/0.1 ml Gavage/Mouse:

Combine 1 ml of compound 1 stock solution and 3 mls of vitamin E depleted peanut oil.

Vehicle:

Combine 1 ml ETOH and 3 mls of vitamin E depleted peanut oil.

EXAMPLE 20

Chemopreventive Properties of 2,5,7,8-tetramethyl-(2R-(4R,8R,12-trimethyltridecyl)chroman-6-yloxy) acetic acid (1) in an ACT Rat Cancer Model Compound 1 is used in vivo to treat transplanted human breast, prostate, and colon tumors transplanted in immune compromised nude mice. The chemopreventive effectiveness of compound 1 in vivo against human breast cancer is shown in an estrogen cancer initiated ACI rat breast cancer model. Approximately 90% of rats implanted with estrogen pellets develop breast cancer within 6 months after estrogen implantation.

Compound 1 is dissolved in 100% ethanol and is diluted to the appropriate dosage using vitamin E depleted peanut oil. The maximum tolerated dose (MTD, maximum dose of compound that can be administered without adverse affects) is determined as described in Examples 14 and 15. Compound 1 is administered at the maximum tolerated dose and 50% of the maximum tolerated dose. ACI rats at 4 weeks of age are subpannicularly implanted with estrogen pellets in the shoulder region. Compound 1 at maximum tolerated dose and 50% of the maximum tolerated dose is administered by gavage. Breast tumors are detected in the control group at approximately 100 days following estrogen implantation. Ninety percent of the control rats develop breast cancer within 6 months after estrogen implantation. Tumor bearing animals from control and treatment groups are sacrificed at various time intervals after treatment initiation, and mammary tissue is examined for obvious tumors, and further examined by histological analyses.

The following references are cited herein.

1. Colowisk, Sidney, P. and Kaplan, Nathan, O. *Methods in Enzymology*, Vol. XVIII, Vitamins and Coenzymes, Part C. Edited by Donald B. McCormick and Lemuel D. Wright. Section XII, PP. 335.

2. Dhar, A., Liu, S., Klucik, J., Berlin, K. D., Madler, M. M., Lu, S., Ivey, R. T., Zacheis, D., Brwon, C. W., Nelson, E. C., Birchbichler, P. J., Benbrook, D. M. Synthesis, Structure-Activity Relationships, and RARγ-Ligand Interactions of Nitrogen Heteroarotinoids. *J. Med. Chem.* 42, pp. 3602-3614 (1999).

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A compound of the formula:

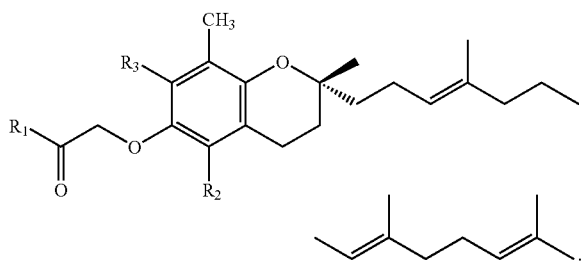

wherein:
$R_1$ is hydroxy or methoxy;
$R_2$ and $R_3$ are independently hydrogen or methyl.

2. The compound of claim 1, wherein $R_1$ is hydroxy.
3. The compound of claim 1, wherein $R_1$ is methoxy.
4. The compound of claim 1, wherein $R_2$ is hydrogen.
5. The compound of claim 1, wherein $R_2$ is methyl.
6. The compound of claim 1, wherein $R_3$ is hydrogen.
7. The compound of claim 1, wherein $R_3$ is methyl.
8. The compound of claim 1, wherein the compound is

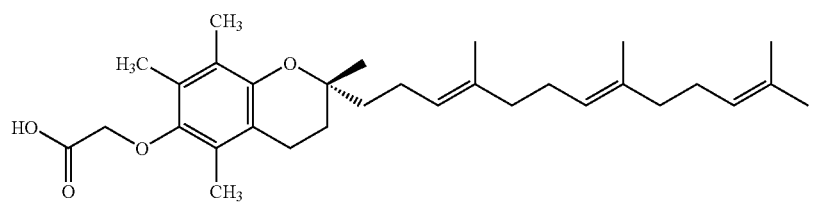

* * * * *

UNITED STATES PATENT AND TRADEMARK OFFICE
CERTIFICATE OF CORRECTION

PATENT NO. : 7,718,814 B2  Page 1 of 1
APPLICATION NO. : 11/928991
DATED : May 18, 2010
INVENTOR(S) : Bob G. Sanders et al.

It is certified that error appears in the above-identified patent and that said Letters Patent is hereby corrected as shown below:

In Title page, item (*) Notice, insert
--This patent is subject to a terminal disclaimer.--.

In Title page, item (57) Abstract, delete "and $R^1$ is alkenyl" and insert
--and $R^5$ is alkenyl-- therefor.

In claim 1, column 58, lines 34-44, delete chemical drawing and insert

-- 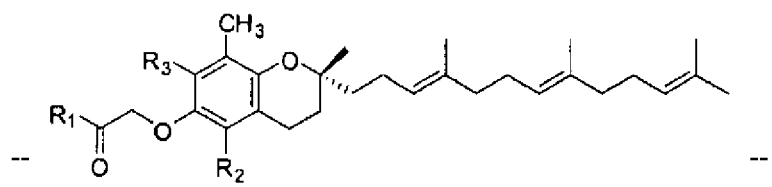 -- therefor.

Signed and Sealed this

Seventeenth Day of August, 2010

David J. Kappos
*Director of the United States Patent and Trademark Office*